(12) United States Patent
Fujii et al.

(10) Patent No.: US 11,339,151 B2
(45) Date of Patent: May 24, 2022

(54) ALIPHATIC ACID AMIDE DERIVATIVE

(71) Applicant: Sumitomo Dainippon Pharma Co., Ltd., Osaka (JP)

(72) Inventors: Yuki Fujii, Tokyo (JP); Masayuki Sakuma, Tokyo (JP); Yoshinori Aihara, Osaka (JP); Jeremy Besnard, United Kingdom (GB); Andrew Simon Bell, United Kingdom (GB)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

(21) Appl. No.: 17/528,743

(22) Filed: Nov. 17, 2021

(65) Prior Publication Data
US 2022/0073506 A1    Mar. 10, 2022

Related U.S. Application Data

(63) Continuation of application No. PCT/JP2020/048117, filed on Dec. 23, 2020.

(30) Foreign Application Priority Data

Dec. 24, 2019   (JP) .............................. JP2019-232927

(51) Int. Cl.
*C07D 413/14*   (2006.01)
*C07D 401/04*   (2006.01)
*C07D 413/04*   (2006.01)

(52) U.S. Cl.
CPC ......... *C07D 413/14* (2013.01); *C07D 401/04* (2013.01); *C07D 413/04* (2013.01)

(58) Field of Classification Search
CPC .................................................. C07D 413/14
USPC .................................................. 514/254.04
See application file for complete search history.

(56) References Cited

U.S. PATENT DOCUMENTS

| | | | |
|---|---|---|---|
| 4,880,930 A | 11/1989 | New | |
| 5,801,176 A | 9/1998 | Hrib et al. | |
| 5,880,121 A * | 3/1999 | Hrib | C07D 261/20 514/218 |
| 6,589,956 B2 * | 7/2003 | Lavielle | C07D 409/14 514/254.04 |
| 2004/0186108 A1 | 9/2004 | Cho et al. | |
| 2007/0004752 A1 | 1/2007 | Coughlin et al. | |
| 2008/0214539 A1 | 9/2008 | Coughlin et al. | |
| 2009/0163514 A1 | 6/2009 | Coughlin et al. | |
| 2015/0297586 A1 * | 10/2015 | Zhou | C07D 209/08 514/254.04 |

FOREIGN PATENT DOCUMENTS

| | | |
|---|---|---|
| JP | 1-168677 | 7/1989 |
| JP | 9-3060 | 1/1997 |
| JP | 2006-508101 | 3/2006 |
| JP | 2008-539268 | 11/2008 |

OTHER PUBLICATIONS

International Search Report dated Feb. 16, 2021 in International (PCT) Application No. PCT/JP2020/048117.
Norman, M.H., et al., "Synthesis and Evaluation of Heterocyclic Carboxamides as Potential Antipsychotic Agents", J. Med. Chem., 1996, vol. 39, pp. 4692-4703.
Seeman, P., "Atypical Antipsychotics: Mechanism of Action", W. Can. J. Psychiatry, vol. 4, No. 1, Feb. 2002, pp. 27-38.
Schmidt, C.J., et al., "The Role of 5-$HT_{2A}$ Receptors in Antipsychotic Activity", Life Sciences, vol. 56, No. 25, 1995, pp. 2209-2222.
Citrome, L., "Lurasidone for schizophrenia: a review of the efficacy and safety profile for this newly approved second-generation antipsychotic", The International Journal of Clinical Practice, vol. 65, No. 2, Feb. 2011, pp. 189-210.
Woo, Y.S., et al., "Lurasidone as a potential therapy for bipolar disorder", Neuropsychiatric Disease and Treatment, vol. 9, 2013, pp. 1521-1529.
Sanchez, C., et al., "Vortioxetine, a novel antidepressant with multimodal activity: Review of preclinical and clinical data", Pharmacology & Therapeutics, vol. 145, 2015, pp. 43-57.
Bonaventure, P., et al., "Selective Blockade of 5-Hydroxytryptamine (5-$HT)_7$ Receptors Enhances 5-HT Transmission, Antidepressant-Like Behavior, and Rapid Eye Movement Sleep Suppression Induced by Citalopram in Rodents", The Journal of Pharmacology and Experimental Therapeutics, vol. 321, No. 2, 2007, pp. 690-698.

(Continued)

*Primary Examiner* — Kahsay Habte
(74) *Attorney, Agent, or Firm* — Wenderoth, Lind & Ponack, L.L.P.

(57) ABSTRACT

The present invention relates to a compound represented by formula (1):

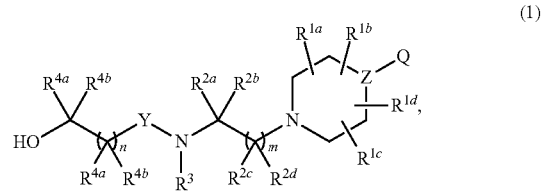

(1)

the compound having antagonist activity against serotonin 5-$HT_{2A}$ receptors and serotonin 5-$HT_7$ receptors; or a pharmaceutically acceptable salt of the compound. (In the formula, Z is a nitrogen atom and the like; Y is carbonyl and the like; m and n are 1 and the like; $R^{1a}$ through $R^{1d}$, $R^{2a}$ through $R^{2d}$, and $R^{4a}$ through $R^{4d}$ are a hydrogen atom and the like; $R^3$ is alkyl and the like; and Q is a specific bicyclic group.)

8 Claims, 2 Drawing Sheets

(56) References Cited

OTHER PUBLICATIONS

Horisawa, T., et al., "The effects of selective antagonists of serotonin $5\text{-}HT_7$ and $5\text{-}HT_{1A}$ receptors on MK-801-induced impairment of learning and memory in the passive avoidance and Morris water maze tests in rats: Mechanistic implications for the beneficial effects of the novel atypical antipsychotic lurasidone". Behavioural Brain Research, vol. 220, 2011, pp. 83-90.

Guscott, M., et al., "Genetic knockout and pharmacological blockade studies of the $5\text{-}HT_7$ receptor suggest therapeutic potential in depression", Neuropharmacology, vol. 48, 2005, pp. 492-502.

Lovenberg, T W., et al., "A Novel Adenylyl Cyclase-Activating Serotonin Receptor ($5\text{-}HT_7$) Implicated in the Regulation of Mammalian Circadian Rhythms", Neuron, vol. 11, Sep. 1993, pp. 449-458.

\* cited by examiner

[Fig. 1]
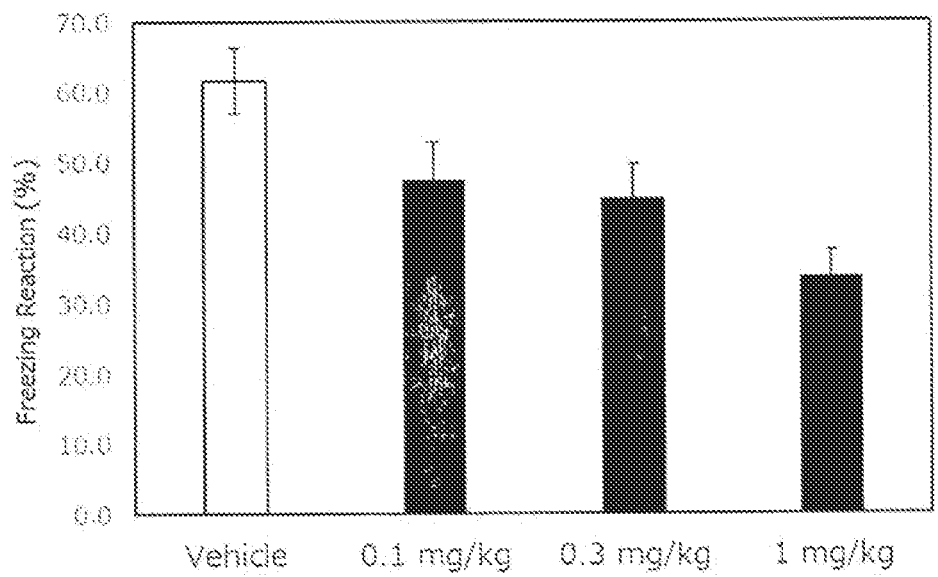
[Fig. 2]
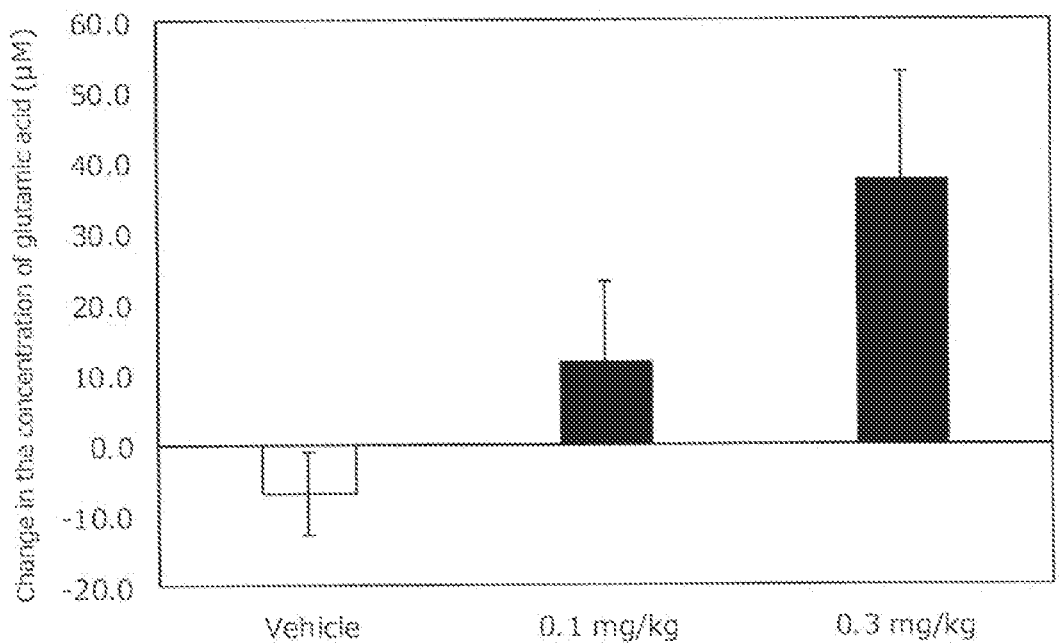

[Fig. 3]
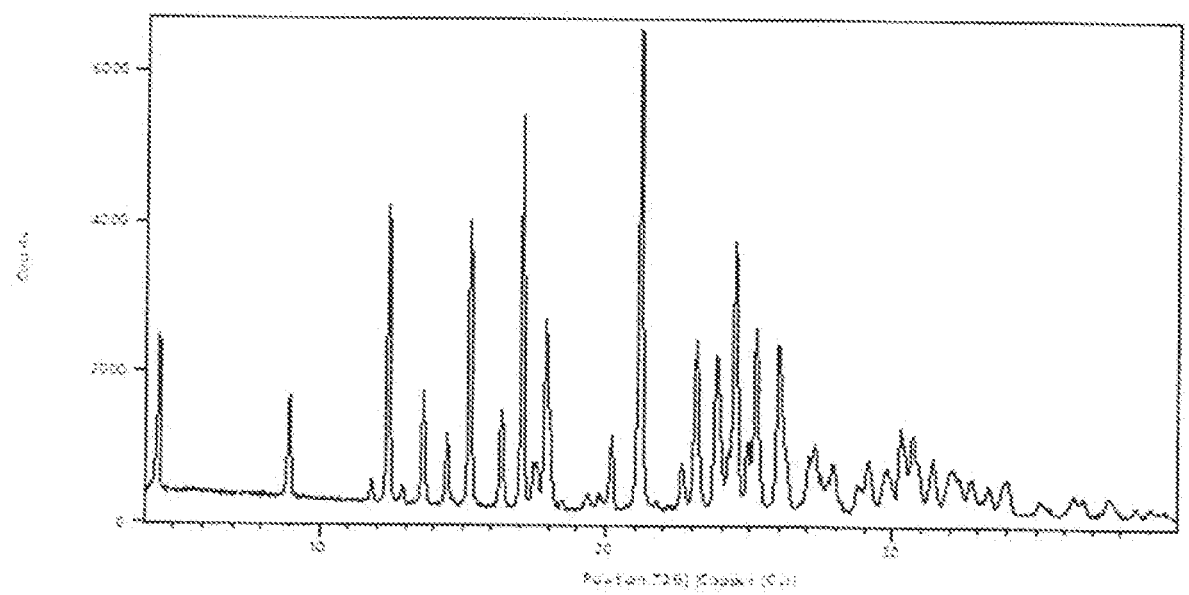

ALIPHATIC ACID AMIDE DERIVATIVE

TECHNICAL FIELD

The present invention relates to an aliphatic acid amide derivative having antagonist activity for the serotonin 5-HT$_{2A}$ receptor and the serotonin 5-HT$_7$ receptor, or a pharmaceutically acceptable salt thereof, and a medicament for treating a neuropsychiatric disease comprising the same as an active ingredient.

BACKGROUND ART

The serotonin (5-hydroxytryptamine; hereinafter, also referred to as "5-HT") is known as one of main neurotransmitters in central nervous system, and it is also known that serotonin is involved in various brain functions such as emotional reaction and cognitive function.

The 5-HT$_{2A}$ receptor which is one of 5-HT receptor subtypes is a Gq/11 protein-coupled receptor, and is highly expressed in, for example, cerebral cortex, hippocampus, and raphe nucleus. Drugs having antagonist activity for the 5-HT$_{2A}$ receptor include antidepressant drugs, mianserin and mirtazapine. Atypical antipsychotic drugs which have antagonist activity for the 5-HT$_{2A}$ receptor are used as a medicament for treating diseases such as schizophrenia, bipolar disorder, major depression, and autistic spectrum disorder (Non-Patent Literature 1, Non-Patent Literature 2).

The 5-HT$_7$ receptor is a Gs protein-coupled receptor, and is extensively expressed in, for example, hypothalamus, thalamus, hippocampus, and raphe nucleus (Non-patent Literature 9). Drugs having antagonist activity for the 5-HT$_7$ receptor include Lurasidone which is used as a medicament for treating schizophrenia and a bipolar disorder and Vortioxetine which is used for treating major depression. There is, however, no commercial drug having selective antagonist activity for the 5-HT$_7$ receptor. Lurasidone is used for treating schizophrenia and a bipolar disorder, and Vortioxetine is used for treating major depression (Non-patent Literature 3, Non-patent Literature 4, and Non-patent Literature 5). It is also known that in some animal models, antagonizing the 5-HT$_7$ receptor leads to antidepressant and anxiolytic effect, and improvement effect in cognition function (Non-patent Literature 6, Non-patent Literature 7). It is also known that 5-HT$_7$ receptor deficient mice exhibit antidepressant effect (Non-patent Literature 8).

As described above, it is shown that antagonists for the 5-HT$_{2A}$ receptor and the 5-HT$_7$ receptor are separately useful for many neuropsychiatric diseases, but no drugs having antagonist activity for the 5-HT$_{2A}$ receptor and the 5-HT$_7$ receptor in a selective and potent manner have been reported.

CITATION LIST

Non Patent Literature

[Non Patent Literature 1] P. Seeman, Can. J. Psychiatry. 4: 27-38, 2002
[Non Patent Literature 2] C. J. Schmidt, Life Science. 56(25): 2209-2222, 1995
[Non Patent Literature 3] L. Citrome, J. Clinical Practice. 65(2): 189-210, 2011
[Non Patent Literature 4] YS. Woo, Neuropsychiatric Disease and Treatment. 9: 1521-1529, 2013
[Non Patent Literature 5] C. Sanchez, Pharmacology & Therapeutics. 145: 43-57, 2015
[Non Patent Literature 6] Bonaventure P, J Pharmacol Exp Ther. 321: 690-8, 2007
[Non Patent Literature 7] Horisawa T, Behavioural Brain Research. 220: 83-90, 2011
[Non Patent Literature 8] M. Guscott, Neuropharmacology. 48: 492-502, 2005
[Non Patent Literature 9] T W. Lovenberg, Neuron. 11: 449-458, 1993

SUMMARY OF INVENTION

Problems to be Solved by the Invention

An object of the present invention is the provision of novel compounds which have antagonist activity for both of the serotonin 5-HT$_{2A}$ receptor and the 5-HT$_7$ receptor, and are useful as a medicament for treating neuropsychiatric diseases.

Means of Solving the Problems

The present inventors have extensively studied to accomplish the above object, and then found that a compound of Formula (1) as below, or a pharmaceutically acceptable salt thereof (hereinafter, also referred to as "the present compound") has antagonist activity for both of the serotonin 5-HT$_{2A}$ receptor and the 5-HT$_7$ receptor. Based upon these new findings, the present invention has been achieved.

The present invention is illustrated as follows.
[Item 1] A compound of Formula (1):

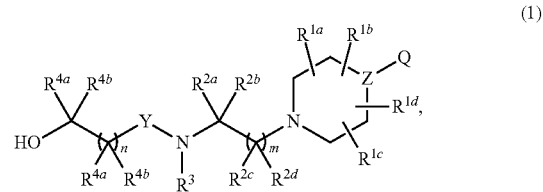

(1)

or a pharmaceutically acceptable salt thereof,
wherein
Z is a nitrogen atom or —CR$^4$—;
Y is carbonyl or sulfonyl;
m is 1, 2, 3, or 4;
n is 0, 1, 2, or 3;
provided that when Y is sulfonyl, n is not 0;
R$^4$ is hydrogen, hydroxy, C$_{1-6}$ alkyl, or C$_{1-6}$ alkoxy;
R$^{1a}$, R$^{1b}$, R$^{1c}$, and R$^{1d}$ are each independently hydrogen, hydroxy, halogen, or C$_{1-6}$ alkyl optionally-substituted with the same or different 1 to 3 halogen;
R$^{2a}$, R$^{2b}$, R$^{2c}$ and R$^{2d}$ are each independently, and each of R$^{2c}$s or each of R$^{2d}$s is independently when R$^{2c}$ or R$^{2d}$ exists plurally, hydrogen, halogen, or C$_{1-6}$ alkyl (wherein the alkyl may be optionally substituted with the same or different 1 to 5 substituents selected from the group consisting of halogen, hydroxy, C$_{3-8}$ cycloalkyl, and C$_{1-6}$ alkoxy), provided that when R$^{2a}$ and R$^{2b}$, or R$^{2c}$ and R$^{2d}$ which attach to the same carbon atom are each independently the said C$_{1-6}$ alkyl, they may be combined together with the carbon atom to which they attach to form a 3- to 6-membered saturated carbocycle;
R$^3$ is C$_{1-6}$ alkyl, wherein the alkyl may be optionally substituted with the same or different 1 to 5 substituents selected from the group consisting of halogen, hydroxy, cyano, C$_{3-8}$ cycloalkyl, and C$_{1-6}$ alkoxy;

$R^{4a}$, $R^{4b}$, $R^{4c}$, and $R^{4d}$ are each independently, and each of $R^{4c}$s or each of $R^{4d}$s is independently when $R^{4c}$ or $R^{4d}$ exists plurally, hydrogen, halogen, $C_{1-6}$ alkyl (wherein the alkyl may be optionally substituted with the same or different 1 to 5 substituents selected from the group consisting of halogen, hydroxy, cyano, $C_{3-8}$ cycloalkyl, $C_{1-6}$ alkoxy, $C_{3-6}$ alkyl ester, and amino optionally-substituted with the same or different 1 or 2 $C_{1-6}$ alkyl (wherein the alkyl may be optionally substituted with oxo)), $C_{2-6}$ alkynyl, or amino (wherein the amino may be optionally substituted with the same or different 1 or 2 $C_{1-6}$ alkyl); provided that when any two of $R^{4a}$, $R^{4b}$, $R^{4c}$, and $R^{4d}$ are each independently the said $C_{1-6}$ alkyl, they may be combined together with the carbon atom or the carbon atoms to which they attach to form a 3- to 6-membered saturated carbocycle or a 4- to 6-membered saturated heterocycle wherein when the said $C_{1-6}$ alkyl groups have a substituent, the substituent may be included as a ring member of the carbocycle or heterocycle;

provided that when Y is sulfonyl and n is 1, any one of $R^{4c}$ or $R^{4d}$ is hydrogen; and when Y is sulfonyl and n is 2 or 3, any one of $R^{4c}$ or $R^{4d}$ which binds to the carbon atom adjacent to Y is hydrogen; and Ring Q is a group of the following Formula (2a), (2b), (2c), (2d), (2e), or (2f):

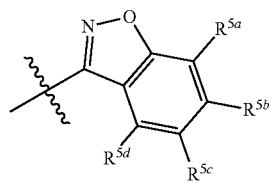

(2a)

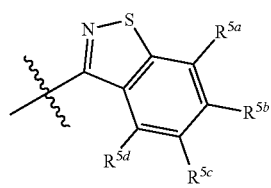

(2b)

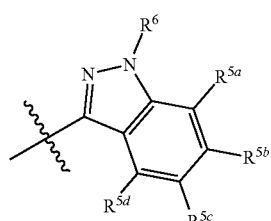

(2c)

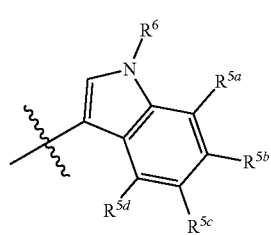

(2d)

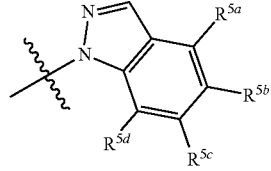

(2e)

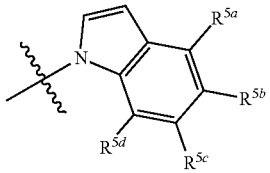

(2f)

wherein $R^{5a}$, $R^{5b}$, $R^{5c}$, and $R^{5d}$ are each independently hydrogen, halogen, cyano, $C_{1-6}$ alkyl, $C_{1-6}$ alkoxy (wherein the alkyl and the alkoxy may be each independently optionally substituted with the same or different 1 to 3 halogen), or amino optionally-substituted with the same or different 1 or 2 $C_{1-6}$ alkyl; and $R^6$ is hydrogen, $C_{1-6}$ alkyl, or $C_{3-8}$ cycloalkyl, wherein the alkyl and the cycloalkyl may be each independently optionally substituted with the same or different 1 to 3 halogen.

[Item 2] The compound of Item 1, or a pharmaceutically acceptable salt thereof, wherein $R^{1a}$, $R^{1b}$, $R^{1c}$, and $R^{1d}$ are hydrogen.

[Item 3] The compound of Item 1 or 2, or a pharmaceutically acceptable salt thereof, wherein $R^{2a}$, $R^{2b}$, $R^{2c}$, and $R^{2d}$ are hydrogen.

[Item 4] The compound of any one of Items 1 to 3, or a pharmaceutically acceptable salt thereof, wherein m is 1.

[Item 5] The compound of any one of Items 1 to 4, or a pharmaceutically acceptable salt thereof, wherein $R^3$ is $C_{1-6}$ alkyl.

[Item 6] The compound of any one of Items 1 to 5, or a pharmaceutically acceptable salt thereof, wherein Z is —$CR^A$—.

[Item 7] The compound of any one of Items 1 to 6, or a pharmaceutically acceptable salt thereof, wherein $R^A$ is hydrogen.

[Item 8] The compound of any one of Items 1 to 7, or a pharmaceutically acceptable salt thereof, wherein $R^{5a}$, $R^{5b}$, $R^{5c}$, and $R^{5d}$ are each independently hydrogen, halogen, or $C_{1-6}$ alkyl.

[Item 9] The compound of any one of Items 1 to 8, or a pharmaceutically acceptable salt thereof, wherein $R^{5a}$, $R^{5c}$, and $R^{5d}$ are hydrogen.

[Item 10] The compound of any one of Items 1 to 9, or a pharmaceutically acceptable salt thereof, wherein $R^{5b}$ is hydrogen, halogen, or $C_{1-6}$ alkyl.

[Item 11] The compound of any one of Items 1 to 10, or a pharmaceutically acceptable salt thereof, wherein $R^6$ is hydrogen.

[Item 12] The compound of any one of Items 1 to 11, or a pharmaceutically acceptable salt thereof, wherein $R^{4a}$, $R^{4b}$, $R^{4c}$, and $R^{4d}$ are each independently, and each of $R^{4c}$s or each of $R^{4d}$s is independently when $R^{4c}$ or $R^{4d}$ exists plurally, hydrogen, halogen, or $C_{1-6}$ alkyl, wherein the alkyl may be optionally substituted with the same or different 1 to 5 substituents selected from the group consisting of halogen, hydroxy, and $C_{1-6}$ alkoxy.

[Item 13] The compound of any one of Items 1 to 12, or a pharmaceutically acceptable salt thereof, wherein n is 0 or 1.

[Item 14] The compound of any one of Items 1 to 13, or a pharmaceutically acceptable salt thereof, wherein Y is carbonyl.

[Item 15] The compound of any one of Items 1 to 13, or a pharmaceutically acceptable salt thereof, wherein Y is sulfonyl.

[Item 16] The compound of Item 1, or a pharmaceutically acceptable salt thereof, wherein the compound is selected from the group consisting of:

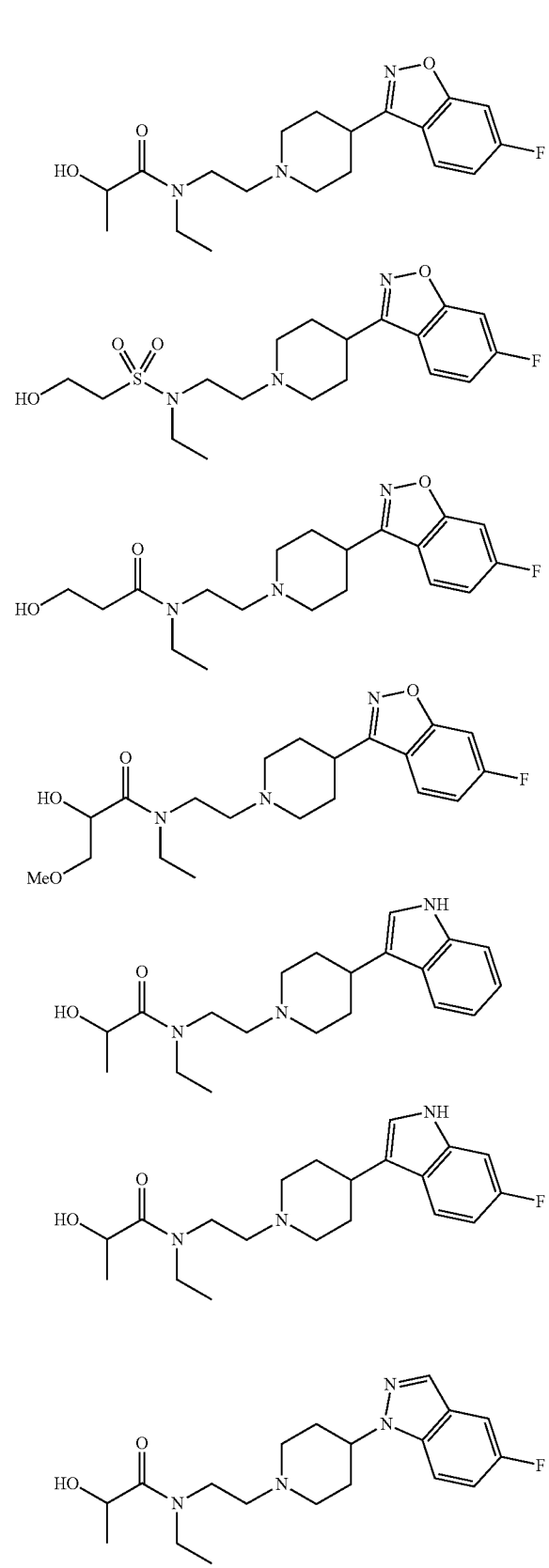

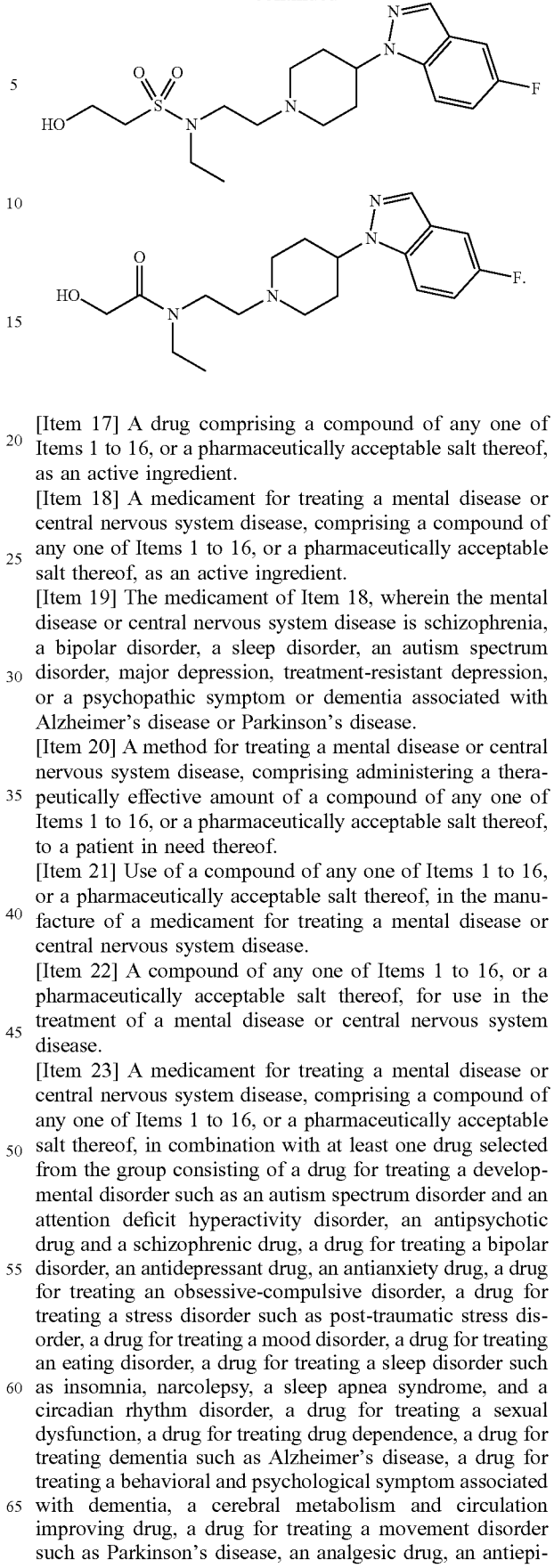

[Item 17] A drug comprising a compound of any one of Items 1 to 16, or a pharmaceutically acceptable salt thereof, as an active ingredient.

[Item 18] A medicament for treating a mental disease or central nervous system disease, comprising a compound of any one of Items 1 to 16, or a pharmaceutically acceptable salt thereof, as an active ingredient.

[Item 19] The medicament of Item 18, wherein the mental disease or central nervous system disease is schizophrenia, a bipolar disorder, a sleep disorder, an autism spectrum disorder, major depression, treatment-resistant depression, or a psychopathic symptom or dementia associated with Alzheimer's disease or Parkinson's disease.

[Item 20] A method for treating a mental disease or central nervous system disease, comprising administering a therapeutically effective amount of a compound of any one of Items 1 to 16, or a pharmaceutically acceptable salt thereof, to a patient in need thereof.

[Item 21] Use of a compound of any one of Items 1 to 16, or a pharmaceutically acceptable salt thereof, in the manufacture of a medicament for treating a mental disease or central nervous system disease.

[Item 22] A compound of any one of Items 1 to 16, or a pharmaceutically acceptable salt thereof, for use in the treatment of a mental disease or central nervous system disease.

[Item 23] A medicament for treating a mental disease or central nervous system disease, comprising a compound of any one of Items 1 to 16, or a pharmaceutically acceptable salt thereof, in combination with at least one drug selected from the group consisting of a drug for treating a developmental disorder such as an autism spectrum disorder and an attention deficit hyperactivity disorder, an antipsychotic drug and a schizophrenic drug, a drug for treating a bipolar disorder, an antidepressant drug, an antianxiety drug, a drug for treating an obsessive-compulsive disorder, a drug for treating a stress disorder such as post-traumatic stress disorder, a drug for treating a mood disorder, a drug for treating an eating disorder, a drug for treating a sleep disorder such as insomnia, narcolepsy, a sleep apnea syndrome, and a circadian rhythm disorder, a drug for treating a sexual dysfunction, a drug for treating drug dependence, a drug for treating dementia such as Alzheimer's disease, a drug for treating a behavioral and psychological symptom associated with dementia, a cerebral metabolism and circulation improving drug, a drug for treating a movement disorder such as Parkinson's disease, an analgesic drug, an antiepileptic drug, an anticonvulsant, a migraine drug, an anesthetic, and a central stimulant.

[Item 24] A medicament for treatment of a mental disease or central nervous system disease, comprising a compound of any one of Items 1 to 16, or a pharmaceutically acceptable salt thereof, as an active ingredient, wherein the medicament is used in the treatment concomitantly with at least one drug selected from the group consisting of a drug for treating a developmental disorder such as an autism spectrum disorder and an attention deficit hyperactivity disorder, an antipsychotic drug and a schizophrenic drug, a drug for treating a bipolar disorder, an antidepressant drug, an antianxiety drug, a drug for treating an obsessive-compulsive disorder, a drug for treating a stress disorder such as a post-traumatic stress disorder, a drug for treating a mood disorder, a drug for treating an eating disorder, a drug for treating a sleep disorder such as insomnia, narcolepsy, a sleep apnea syndrome, and a circadian rhythm disorder, a drug for treating a sexual dysfunction, a drug for treating drug dependence, a drug for treating dementia such as Alzheimer's disease, a drug for treating a behavioral and psychological symptom associated with dementia, a cerebral metabolism and circulation improving drug, a drug for treating a movement disorder such as Parkinson's disease, an analgesic drug, an antiepileptic drug, an anticonvulsant, a migraine drug, an anesthetic, and a central stimulant.

[Item 25] A crystal of a compound of any one of Examples 17, 77, 78, 79, and 80, characterized by powder XRD patterns comprising powder XRD peaks of 4 or more (preferably 10 or more) 2θ±0.2 values selected from those measured in each of the Examples.

Effect of the Invention

The present compound has antagonist activity for the 5-HT$_{2A}$ receptor and the 5-HT$_7$ receptor. The present compound is useful as a medicament for treating a neuropsychiatric disease and a central nervous system disease.

BRIEF DESCRIPTION OF DRAWINGS

FIG. 1 shows results of fear conditioning test using the compound of Example 17 (Test 6).

FIG. 2 shows results of measurement of the amount of released glutamic acid in rat brain using the compound of Example 17 (Test 7).

FIG. 3 shows a chart of powder XRD measurement of the compound of Example 78.

DESCRIPTION OF EMBODIMENTS

Hereinafter, the present invention is described in detail. In the description, the number of carbon atoms in a definition of "substituent" may be indicated as, for example, "$C_{1-6}$". Specifically, the term "$C_{1-6}$ alkyl" means an alkyl group having 1 to 6 carbon atoms.

The "halogen" used herein includes, for example, fluorine atom, chlorine atom, bromine atom, and iodine atom. Preferably, it includes fluorine atom and chlorine atom.

The "$C_{1-6}$ alkyl" used herein means a straight- or branched-chain saturated hydrocarbon group having 1 to 6 carbon atoms. Preferably, the "$C_{1-6}$ alkyl" includes "$C_{1-4}$ alkyl", and more preferably, it includes "$C_{1-3}$ alkyl". The "$C_{1-3}$ alkyl" includes, for example, methyl, ethyl, propyl, and 1-methylethyl. The "$C_{1-4}$ alkyl" includes, for example, butyl, 1,1-dimethylethyl, 1-methylpropyl, and 2-methylpropyl, besides the above-listed examples of the "$C_{1-3}$ alkyl".

The "$C_{1-6}$ alkyl" includes, for example, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, and hexyl, besides the above-listed examples of the "$C_{1-4}$ alkyl".

The phrase "alkyl is substituted with oxo" used herein means that a keto group (C=O) is formed with any one of carbon atoms of which the alkyl consists.

The "$C_{3-8}$ cycloalkyl" used herein means a cyclic saturated hydrocarbon group having 3 to 8 carbon atoms, and it includes those which have a partially-unsaturated bond or a bridged structure. The "$C_{3-8}$ cycloalkyl" preferably includes "$C_{3-6}$ cycloalkyl". The "$C_{3-6}$ cycloalkyl" includes, for example, cyclopropyl, cyclobutyl, cyclopentyl, and cyclohexyl. The "$C_{3-8}$ cycloalkyl" includes, for example, cycloheptyl and cyclooctyl, besides the above-listed examples of the "$C_{3-6}$ cycloalkyl".

The "$C_{1-6}$ alkoxy" is used interchangeably with "$C_{1-6}$ alkyloxy" herein, and the "$C_{1-6}$ alkyl" part is the same as the above "$C_{1-6}$ alkyl". The "$C_{1-6}$ alkoxy" preferably includes "$C_{1-4}$ alkoxy", and more preferably "$C_{1-3}$ alkoxy". The "$C_{1-3}$ alkoxy" includes, for example, methoxy, ethoxy, propoxy, and 1-methylethoxy. The "$C_{1-4}$ alkoxy" includes, for example, butoxy, 1,1-dimethylethoxy, 1-methylpropoxy, and 2-methylpropoxy, besides the above-listed examples of the "$C_{1-3}$ alkoxy". The "$C_{1-6}$ alkoxy" includes, for example, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, and hexyloxy, besides the above-listed examples of the "$C_{1-4}$ alkoxy".

The "$C_{1-6}$ alkyl ester" used herein means an ester (—COOR') of which R' part is the above "$C_{1-6}$ alkyl". The "$C_{1-6}$ alkyl ester" preferably includes "$C_{1-4}$ alkyl ester", and more preferably "$C_{1-3}$ alkyl ester". The "$C_{1-3}$ alkyl ester" includes, for example, methyl ester, ethyl ester, propyl ester, and 1-methylethyl ester. The "$C_{1-4}$ alkyl ester" includes, for example, butyl ester, 1,1-dimethylethyl ester, 1-methylpropyl ester, and 2-methylpropyl ester, besides the above-listed examples of the "$C_{1-3}$ alkyl ester". The "$C_{1-6}$ alkyl ester" includes, for example, pentyl ester, 1,1-dimethylpropyl ester, 1,2-dimethylpropyl ester, 1-methylbutyl ester, 2-methylbutyl ester, 4-methylpentyl ester, 3-methylpentyl ester, 2-methylpentyl ester, 1-methylpentyl ester, and hexyl ester, besides the above-listed examples of the "$C_{1-4}$ alkyl ester".

The "$C_{2-6}$ alkynyl" used herein means a straight- or branched-chain unsaturated hydrocarbon group having a triple bond and 2 to 6 carbon atoms. The "$C_{2-6}$ alkynyl" preferably includes "$C_{2-4}$ alkynyl", and more preferably "$C_{2-3}$ alkynyl". The "$C_{2-3}$ alkynyl" includes, for example, ethynyl and propynyl. The "$C_{2-4}$ alkynyl" includes, for example, butynyl, besides the above-listed examples of the "$C_{2-3}$ alkynyl". The "$C_{2-6}$ alkynyl" includes, for example, pentynyl and hexynyl, besides the above-listed examples of the "$C_{2-4}$ alkynyl".

The "3- to 6-membered saturated carbocycle" used herein means a cyclic saturated hydrocarbon group having 3 to 6 carbon atoms that includes those which have a partially-unsaturated bond or a bridged structure. The "3- to 6-membered saturated carbocycle" preferably includes "5- or 6-membered monocyclic saturated carbocycle". The "5- or 6-membered monocyclic saturated carbocycle" includes, for example, cyclopentane and cyclohexane. The "3- to 6-membered saturated carbocycle" includes, for example, cyclopropane and cyclobutane, besides the above-listed examples of the "5- or 6-membered monocyclic saturated carbocycle".

The "4- to 6-membered saturated heterocycle" group means a saturated ring composed of 4 to 6 atoms comprising 1 or 2 atoms independently selected from the group consisting of nitrogen atom, oxygen atom, and sulfur atom, besides carbon atoms. The "4- to 6-membered saturated heterocycle" group includes those which have a partially-unsaturated bond or a bridged structure. The "4- to 6-membered saturated heterocycle" group preferably includes "5- or 6-membered monocyclic saturated heterocycle" group. The "5- or 6-membered monocyclic saturated heterocycle" group includes, for example, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, oxoimidazolidinyl, dioxoimidazolidinyl, oxooxazolidinyl, dioxooxazolidinyl, dioxothiazolidinyl, tetrahydrofuranyl, tetrahydropyranyl. The "4- to 6-membered saturated heterocycle" group includes, for example, oxetanyl and azetidinyl, besides the above-listed examples of the "5- or 6-membered monocyclic saturated heterocycle" group.

In a compound of Formula (1), preferred examples of Z, Y, m, n, $R^4$, $R^{1a}$, $R^{1b}$, $R^{1c}$, $R^{1d}$, $R^{2a}$, $R^{2b}$, $R^{2c}$, $R^{2d}$, $R^3$, $R^{4a}$, $R^{4b}$, $R^{4c}$, $R^{4d}$, Q $R^{5a}$, $R^{5b}$, $R^{5c}$, $R^{5d}$, and $R^6$ are shown below, but the scope of the present invention is not limited to the scope of the following compounds.

One embodiment of Z includes —$CR^A$—. Another embodiment of Z includes a nitrogen atom.

One embodiment of Y includes carbonyl. Another embodiment of Y includes sulfonyl.

A preferred embodiment of m includes 1 and 2. A more preferred embodiment of m includes 1.

A preferred embodiment of n includes 0, 1, and 2. A more preferred embodiment of n includes 0 and 1. An especially preferred embodiment of n includes 1.

A preferred embodiment of $R^4$ includes hydrogen, hydroxy, and $C_{1-6}$ alkyl. A more preferred embodiment includes hydrogen and $C_{1-3}$ alkyl. A further preferred embodiment includes hydrogen, ethyl, and methyl. The most preferred embodiment includes hydrogen.

Preferred embodiments of $R^{1a}$, $R^{1b}$, $R^{1c}$, and $R^{1d}$ include, each independently, hydrogen, hydroxy, halogen, and $C_{1-6}$ alkyl. More preferred embodiments include hydrogen, halogen, and $C_{1-3}$ alkyl. Further preferred embodiments include hydrogen, fluorine atom, chlorine atom, ethyl, and methyl. Especially preferred embodiments include hydrogen, fluorine atom, and methyl. The most preferred embodiments include hydrogen.

Preferred embodiments of $R^{2a}$, $R^{2b}$, $R^{2c}$, and $R^{2d}$ include, each independently, hydrogen, halogen, and $C_{1-6}$ alkyl. More preferred embodiments include hydrogen, halogen, and $C_{1-3}$ alkyl. Further preferred embodiments include hydrogen, fluorine atom, chlorine atom, ethyl, and methyl. Especially preferred embodiments include hydrogen, fluorine atom, and methyl. The most preferred embodiments include hydrogen.

A preferred embodiment of $R^3$ includes $C_{1-6}$ alkyl. More preferred embodiment includes $C_{1-3}$ alkyl. A further preferred embodiment includes ethyl and methyl. An especially preferred embodiment includes ethyl.

Preferred embodiments of $R^{4a}$, $R^{4b}$, $R^{4c}$, and $R^{4d}$ include, each independently, hydrogen, halogen, $C_{1-6}$ alkyl, $C_{2-6}$ alkynyl, and amino optionally-substituted with the same or different 1 or 2 $C_{1-6}$ alkyl. More preferred embodiments include hydrogen, halogen, $C_{1-6}$ alkyl, and amino optionally-substituted with the same or different 1 or 2 $C_{1-6}$ alkyl. Further preferred embodiments include hydrogen, halogen, and $C_{1-6}$ alkyl. Especially preferred embodiments include hydrogen and $C_{1-6}$ alkyl. Especially preferred embodiments include hydrogen, methyl, and methoxymethyl. The most preferred embodiments include hydrogen.

A preferred embodiment of Q includes (2a), (2c), (2d), (2e), and (2f). A more preferred embodiment includes (2a), (2d), and (2e). An especially preferred embodiment includes (2a).

Preferred embodiments of $R^{5a}$, $R^{5b}$, $R^{5c}$, and $R^{5d}$ include, each independently, hydrogen, halogen, cyano, $C_{1-6}$ alkyl, $C_{1-6}$ alkoxy, and amino optionally-substituted with the same or different 1 or 2 $C_{1-6}$ alkyl. More preferred embodiments include hydrogen, halogen, cyano, $C_{1-6}$ alkyl, and $C_{1-6}$ alkoxy. Further preferred embodiments include hydrogen, fluorine atom, and chlorine atom. Especially preferred embodiments include hydrogen and fluorine atom.

A preferred embodiment of $R^6$ includes hydrogen, $C_{1-6}$ alkyl, and $C_{3-8}$ cycloalkyl. A more preferred embodiment includes hydrogen and $C_{1-6}$ alkyl. A further preferred embodiment includes hydrogen and $C_{1-3}$ alkyl. An especially preferred embodiment includes hydrogen.

One embodiment of a compound of Formula (1) includes the following embodiment (A):

(A) A compound, or a pharmaceutically acceptable salt thereof, wherein

Z is a nitrogen atom or —$CR^A$—;

Y is carbonyl or sulfonyl;

m is 1 or 2;

n is 0, 1, 2, or 3;

provided that when Y is sulfonyl, n is not 0;

$R^A$ is hydrogen or $C_{1-6}$ alkyl;

$R^{1a}$, $R^{1b}$, $R^{1c}$, and $R^{1d}$ are each independently hydrogen or $C_{1-6}$ alkyl;

$R^{2a}$, $R^{2b}$, $R^{2c}$, and $R^{2d}$ are each independently, and each of $R^{2c}$s or each of $R^{2d}$s is independently when $R^{2c}$ or $R^{2d}$ exists plurally, hydrogen or $C_{1-6}$ alkyl;

$R^3$ is $C_{1-6}$ alkyl;

$R^{4a}$, $R^{4b}$, $R^{4c}$, and $R^{4d}$ are each independently, and each of $R^{4c}$s or each of $R^{4d}$s is independently when $R^{4c}$ or $R^{4d}$ exists plurally, hydrogen, halogen, $C_{1-6}$ alkyl (wherein the alkyl may be optionally substituted with the same or different 1 to 5 substituents selected from the group consisting of halogen, hydroxy, $C_{1-6}$ alkoxy, $C_{1-6}$ alkyl ester, and amino optionally-substituted with the same or different 1 or 2 $C_{1-6}$ alkyl (wherein the alkyl may be optionally substituted with oxo)), $C_{2-6}$ alkynyl, or amino (wherein the amino may be optionally substituted with the same or different 1 or 2 $C_{1-6}$ alkyl); provided that when any two of $R^{4a}$, $R^{4b}$, $R^{4c}$, and $R^{4d}$ are each independently the above $C_{1-5}$ alkyl, they may be combined together with the carbon atom or the carbon atoms to which they attach to form a 3- to 6-membered saturated carbocycle or a 4- to 6-membered saturated heterocycle wherein when the $C_{1-6}$ alkyl groups have a substituent, the substituent may be included as a ring member of the carbocycle or heterocycle;

provided that when Y is sulfonyl and n is 1, either $R^{4c}$ or $R^{4d}$ is hydrogen; and when Y is sulfonyl and n is 2 or 3, either $R^{4c}$ or $R^{4d}$ that binds to the carbon atom adjacent to Y is hydrogen; and Ring Q is a group of the following Formula (2a), (2b), (2c), (2d), (2e), or (2f):

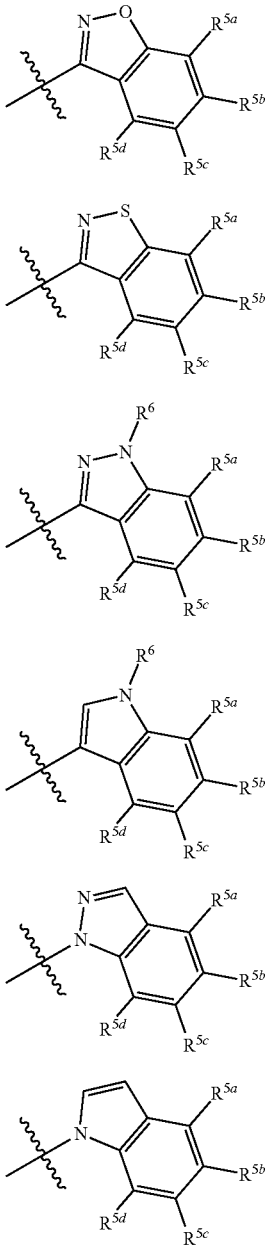

wherein $R^{5a}$, $R^{5b}$, $R^{5c}$, and $R^{5d}$ are each independently hydrogen, halogen, or $C_{1-6}$ alkyl; and $R^6$ is hydrogen or $C_{1-6}$ alkyl.

Another embodiment of a compound of Formula (1) includes the following embodiment (B):

(B) A compound, or a pharmaceutically acceptable salt thereof, wherein

Z is a nitrogen atom or —$CR^A$—;

Y is carbonyl;

m is 1 or 2;

n is 0, 1, 2, or 3;

$R^A$ is hydrogen or $C_{1-6}$ alkyl;

$R^{1a}$, $R^{1b}$, $R^{1c}$, and $R^{1d}$ are each independently hydrogen or $C_{1-6}$ alkyl;

$R^{2a}$, $R^{2b}$, $R^{2c}$, and $R^{2d}$ are each independently, and each of $R^{2c}$s or each of $R^{2d}$s is independently when $R^{2c}$ or $R^{2d}$ exists plurally, hydrogen or $C_{1-6}$ alkyl;

$R^3$ is $C_{1-6}$ alkyl;

$R^{4a}$, $R^{4b}$, $R^{4c}$, and $R^{4d}$ are each independently, and each of $R_{4c}$s or each of $R^{4d}$s is independently when $R^{4c}$ or $R^{4d}$ exists plurally, hydrogen, halogen, $C_{1-6}$ alkyl (wherein the alkyl may be optionally substituted with the same or different 1 to 5 substituents selected from the group consisting of halogen, hydroxy, $C_{1-6}$ alkoxy, $C_{1-6}$ alkyl ester, and amino optionally-substituted with the same or different 1 or 2 $C_{1-6}$ alkyl (wherein the alkyl may be optionally substituted with oxo)), $C_{2-6}$ alkynyl, or amino (wherein the amino may be optionally substituted with the same or different 1 or 2 $C_{1-6}$ alkyl); provided that when any two of $R^{4a}$, $R^{4b}$, $R^{4c}$, and $R^{4d}$ are each independently the above $C_{1-6}$ alkyl, they may be combined together with the carbon atom or the carbon atoms to which they attach to form a 3- to 6-membered saturated carbocycle or a 4- to 6-membered saturated heterocycle wherein when the $C_{1-6}$ alkyl groups have a substituent, the substituent may be included as a ring member of the carbocycle or heterocycle;

Ring Q is a group of the following Formula (2a), (2b), (2c), (2d), (2e), or (2f):

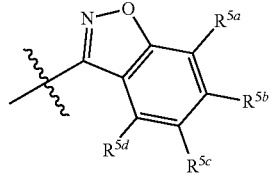

(2a)

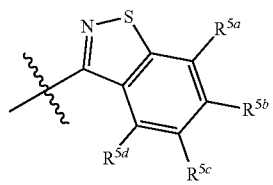

(2b)

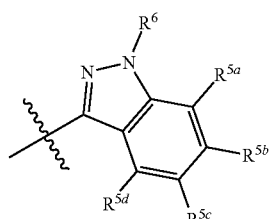

(2c)

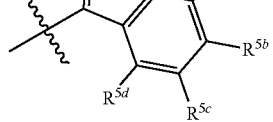

(2d)

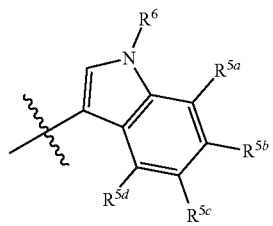

(2e)

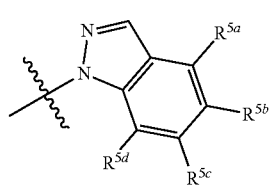

13

-continued (2f)

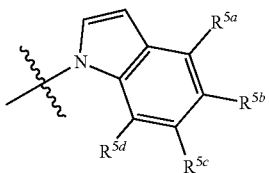

wherein $R^{5a}$, $R^{5b}$, $R^{5c}$, and $R^{5d}$ are each independently hydrogen, halogen, or $C_{1-6}$ alkyl; and $R^6$ is hydrogen or $C_{1-6}$ alkyl.

Another embodiment of a compound of Formula (1) includes the following embodiment (C):

(C) A compound, or a pharmaceutically acceptable salt thereof, wherein

Z is a nitrogen atom or —$CR^A$—;

Y is sulfonyl;

m is 1 or 2;

n is 1, 2, or 3;

$R^A$ is hydrogen or $C_{1-6}$ alkyl;

$R^{1a}$, $R^{1b}$, $R^{1c}$, and $R^{1d}$ are each independently hydrogen or $C_{1-6}$ alkyl;

$R^{2a}$, $R^{2b}$, $R^{2c}$, and $R^{2d}$ are each independently, and each of $R^{2c}$s or each of $R^{2d}$s is independently when $R^{2c}$ or $R^{2d}$ exists plurally, hydrogen or $C_{1-6}$ alkyl;

$R^3$ is $C_{1-6}$ alkyl;

$R^{4a}$, $R^{4b}$, $R^{4c}$, and $R^{4d}$ are each independently, and each of $R^{4c}$s or each of $R^{4d}$s is independently when $R^{4c}$ or $R^{4d}$ exists plurally, hydrogen, halogen, $C_{1-6}$ alkyl (wherein the alkyl may be optionally substituted with the same or different 1 to 5 substituents selected from the group consisting of halogen, hydroxy, $C_{1-6}$ alkoxy, $C_{1-6}$ alkyl ester, and amino optionally-substituted with the same or different 1 or 2 $C_{1-6}$ alkyl (wherein the alkyl may be optionally substituted with oxo)), $C_{2-6}$ alkynyl, or amino (wherein the amino may be optionally substituted with the same or different 1 or 2 $C_{1-6}$ alkyl); provided that when any two of $R^{4a}$, $R^{4b}$, $R^{4c}$, and $R^{4d}$ are each independently the above $C_{1-6}$ alkyl, they may be combined together with the carbon atom or the carbon atoms to which they attach to form a 3- to 6-membered saturated carbocycle or a 4- to 6-membered saturated heterocycle wherein when the $C_{1-6}$ alkyl groups have a substituent, the substituent may be included as a ring member of the carbocycle or heterocycle;

provided that when n is 1, either $R^{4c}$ or $R^{4d}$ is hydrogen; and when n is 2 or 3, either $R^{4c}$ or Rid that binds to the carbon atom adjacent to Y is hydrogen; and Ring Q is a group of the following Formula (2a), (2b), (2c), (2d), (2e), or (2f):

(2a)

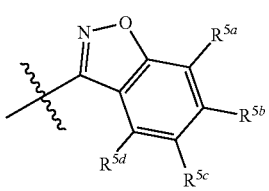

14

-continued (2b)

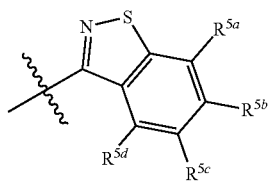

(2c)

(2d)

(2e)

(2f)

wherein $R^{5a}$, $R^{5b}$, $R^{5c}$, and $R^{5d}$ are each independently hydrogen, halogen, or $C_{1-6}$ alkyl; and $R^6$ is hydrogen or $C_{1-6}$ alkyl.

Another embodiment of a compound of Formula (1) includes the following embodiment (D):

(D) A compound, or a pharmaceutically acceptable salt thereof, wherein

Z is —$CR^A$—;

Y is carbonyl;

m is 1;

n is 0 or 1;

$R^A$ is hydrogen;

$R^{1a}$, $R^{1b}$, $R^{1c}$, and $R^{1d}$ are hydrogen;

$R^{2a}$, $R^{2b}$, $R^{2c}$, and $R^{2d}$ are hydrogen;

$R^3$ is $C_{1-6}$ alkyl;

$R^{4a}$, $R^{4b}$, $R^{4c}$, and $R^{4d}$ are each independently, and each of $R^{4c}$s or each of $R^{4d}$s is independently when $R^{4c}$ or $R^{4d}$ exists plurally, hydrogen, halogen, $C_{1-6}$ alkyl (wherein the alkyl may be optionally substituted with the same or different 1 to 5 substituents selected from the group consisting of halogen, hydroxy, $C_{1-6}$ alkoxy, $C_{1-6}$ alkyl ester, and amino optionally-substituted with the same or different 1 or 2 $C_{1-6}$ alkyl (wherein the alkyl may be optionally substituted with oxo)), $C_{2-6}$ alkynyl, or amino (wherein the amino may be optionally substituted with the same or different 1 or 2 $C_{1-6}$ alkyl); provided that when any two of $R^{4a}$, $R^{4b}$, $R^{4c}$, and $R^{4d}$ are each independently the above $C_{1-6}$ alkyl, they may be combined together with the carbon atom or the carbon atoms to which they attach to form a 3- to 6-membered saturated carbocycle or a 4- to 6-membered saturated heterocycle wherein when the $C_{1-6}$ alkyl groups have a substituent, the substituent may be included as a ring member of the carbocycle or heterocycle; and Ring Q is a group of formula (2a).

Another embodiment of a compound of Formula (1) includes the following embodiment (E):

(E) A compound, or a pharmaceutically acceptable salt thereof, wherein

Z is —$CR^A$—;
Y is carbonyl;
m is 1;
n is 0 or 1;
$R^A$ is hydrogen;
$R^{1a}$, $R^{1b}$, $R^{1c}$, and $R^{1d}$ are each independently hydrogen;
$R^{2a}$, $R^{2b}$, $R^{2c}$, and $R^{2d}$ are each independently hydrogen;
$R^3$ is $C_{1-6}$ alkyl;
$R^{4a}$, $R^{4b}$, $R^{4c}$, and $R^{4d}$ are each independently, and each of $R^{4c}$s or each of $R^{4d}$s is independently when $R^{4c}$ or $R^{4d}$ exists plurally, hydrogen, halogen, $C_{1-6}$ alkyl (wherein the alkyl may be optionally substituted with the same or different 1 to 5 substituents selected from the group consisting of halogen, hydroxy, $C_{1-6}$ alkoxy, $C_{1-6}$ alkyl ester, and amino optionally-substituted with the same or different 1 or 2 $C_{1-6}$ alkyl (wherein the alkyl may be optionally substituted with oxo)), $C_{2-6}$ alkynyl, or amino (wherein the amino may be optionally substituted with the same or different 1 or 2 $C_{1-6}$ alkyl); provided that when any two of $R^{4a}$, $R^{4b}$, $R^{4c}$, and $R^{4d}$ are each independently the above $C_{1-6}$ alkyl, they may be combined together with the carbon atom or the carbon atoms to which they attach to form a 3- to 6-membered saturated carbocycle or a 4- to 6-membered saturated heterocycle wherein when the $C_{1-6}$ alkyl groups have a substituent, the substituent may be included as a ring member of the carbocycle or heterocycle; and Ring Q is a group of formula (2d).

Another embodiment of a compound of Formula (1) includes the following embodiment (F):

(F) A compound, or a pharmaceutically acceptable salt thereof, wherein

Z is —$CR^A$—;
Y is carbonyl;
m is 1;
n is 0 or 1;
$R^A$ is hydrogen;
$R^{1a}$, $R^{1b}$, $R^{1c}$, and $R^{1d}$ are hydrogen;
$R^{2a}$, $R^{2b}$, $R^{2c}$, and $R^{2d}$ are hydrogen;
$R^3$ is $C_{1-6}$ alkyl;
$R^{4a}$, $R^{4b}$, $R^{4c}$, and $R^{4d}$ are each independently, and each of $R^{4c}$s or each of $R^{4d}$s is independently when $R^{4c}$ or $R^{4d}$ exists plurally, hydrogen, halogen, $C_{1-6}$ alkyl (wherein the alkyl may be optionally substituted with the same or different 1 to 5 substituents selected from the group consisting of halogen, hydroxy, $C_{1-6}$ alkoxy, $C_{1-6}$ alkyl ester, and amino optionally-substituted with the same or different 1 or 2 $C_{1-6}$ alkyl (wherein the alkyl may be optionally substituted with oxo)), $C_{2-6}$ alkynyl, or amino (wherein the amino may be optionally substituted with the same or different 1 or 2 $C_{1-6}$ alkyl); provided that when any two of $R^{4a}$, $R^{4b}$, $R^{4c}$, and $R^{4d}$ are each independently the above $C_{1-6}$ alkyl, they may be combined together with the carbon atom or the carbon atoms to which they attach to form a 3- to 6-membered saturated carbocycle or a 4- to 6-membered saturated heterocycle wherein when the $C_{1-6}$ alkyl groups have a substituent, the substituent may be included as a ring member of the carbocycle or heterocycle; and Ring Q is a group of formula (2e).

Another embodiment of a compound of Formula (1) includes the following embodiment (G):

(G) A compound, or a pharmaceutically acceptable salt thereof, wherein

Z is —$CR^A$—;
Y is sulfonyl;
m is 1;
n is 1;
$R^A$ is hydrogen;
$R^{1a}$, $R^{1b}$, $R^{1c}$, and $R^{1d}$ are hydrogen;
$R^{2a}$, $R^{2b}$, $R^{2c}$, and $R^{2d}$ are hydrogen;
$R^3$ is $C_{1-6}$ alkyl;
$R^{4a}$, $R^{4b}$, $R^{4c}$, and $R^{4d}$ are each independently, and each of $R^{4c}$s or each of $R^{4d}$s is independently when $R^{4c}$ or $R^{4d}$ exists plurally, hydrogen, halogen, $C_{1-6}$ alkyl (wherein the alkyl may be optionally substituted with the same or different 1 to 5 substituents selected from the group consisting of halogen, hydroxy, $C_{1-6}$ alkoxy, $C_{1-6}$ alkyl ester, and amino optionally-substituted with the same or different 1 or 2 $C_{1-6}$ alkyl (wherein the alkyl may be optionally substituted with oxo)), $C_{2-6}$ alkynyl, or amino (wherein the amino may be optionally substituted with the same or different 1 or 2 $C_{1-6}$ alkyl); provided that when any two of $R^{4a}$, $R^{4b}$, $R^{4c}$, and $R^{4d}$ are each independently the above $C_{1-6}$ alkyl, they may be combined together with the carbon atom or the carbon atoms to which they attach to form a 3- to 6-membered saturated carbocycle or a 4- to 6-membered saturated heterocycle wherein when the $C_{1-6}$ alkyl groups have a substituent, the substituent may be included as a ring member of the carbocycle or heterocycle;

provided that either $R^{4c}$ or $R^{4d}$ is hydrogen; and

Ring Q is a group of formula (2a).

Another embodiment of a compound of Formula (1) includes the following embodiment (H):

(H) A compound, or a pharmaceutically acceptable salt thereof, wherein

Z is —$CR^A$—;
Y is sulfonyl;
m is 1;
n is 1;
$R^A$ is hydrogen;
$R^{1a}$, $R^{1b}$, $R^{1c}$, and $R^{1d}$ are hydrogen;
$R^{2a}$, $R^{2b}$, $R^{2c}$, and $R^{2d}$ are hydrogen;
$R^3$ is $C_{1-6}$ alkyl;
$R^{4a}$, $R^{4b}$, $R^{4c}$, and $R^{4d}$ are each independently, and each of $R^{4c}$s or each of $R^{4d}$s is independently when $R^{4c}$ or $R^{4d}$ exists plurally, hydrogen, halogen, $C_{1-6}$ alkyl (wherein the alkyl may be optionally substituted with the same or different 1 to 5 substituents selected from the group consisting of halogen, hydroxy, $C_{1-6}$ alkoxy, $C_{1-6}$ alkyl ester, amino optionally-substituted with the same or different 1 or 2 $C_{1-6}$ alkyl (wherein the alkyl may be optionally substituted with oxo)), $C_{2-6}$ alkynyl, or amino (wherein the amino may be optionally substituted with the same or different 1 or 2 $C_{1-6}$ alkyl); provided that when any two of $R^{4a}$, $R^{4b}$, $R^{4c}$, and $R^{4d}$ are each independently the above $C_{1-6}$ alkyl, they may be combined together with the carbon atom or the carbon atoms to which they attach to form a 3- to 6-membered saturated carbocycle or a 4- to 6-membered saturated heterocycle wherein when the $C_{1-6}$ alkyl groups have a substituent, the substituent may be included as a ring member of the carbocycle or heterocycle;

provided that either $R^{4c}$ or $R^{4d}$ is hydrogen; and

Ring Q is a group of formula (2e).

A compound of Formula (1) may have at least one asymmetric carbon atom. The present compound, therefore, includes racemates of a compound of Formula (1), as well as optically-active isomers of a compound of Formula (1). When a compound of Formula (1) has two or more asymmetric carbon atoms, it may have stereoisomerism. The present compound, therefore, includes stereoisomers of a compound of Formula (1) and mixtures thereof.

Further, deuterated compounds in which any one, two, or more $^1H$ in a compound of Formula (1) are replaced with $^2H(D)$ are included in a compound of Formula (1).

A compound of Formula (1) or a pharmaceutically acceptable salt thereof may exist in the form of a hydrate and/or a solvate, and the hydrate and solvate such as an ethanol solvate are included in the present compound. Further, the present compound also includes those in crystalline forms of its all embodiments.

When a compound of Formula (1) has an acidic group, a pharmaceutically acceptable salt thereof includes, for example, an alkali metal salt such as a sodium salt and a potassium salt; an alkaline earth metal salt such as a calcium salt and a magnesium salt; an inorganic metal salt such as a zinc salt; and an organic basic salt such as triethylamine, triethanolamine, trihydroxymethylaminomethane, and an amino acid.

When a compound of Formula (1) has a basic group, a pharmaceutically acceptable salt thereof includes, for example, an inorganic acid salt such as hydrochloride, hydrobromide, sulfate, phosphate, and nitrate; an organic acid salt such as acetate, propionate, succinate, lactate, malate, tartrate, citrate, maleate, fumarate, methanesulfonate, p-toluenesulfonate, benzenesulfonate, ascorbate, and orotate.

Hereinafter, the processes to prepare the present compound are explained along with examples, but the present invention shall not be limited thereto.

Preparation Process

The present compound can be prepared by means of any of the preparation processes mentioned below and those combined with known processes.

Each compound appearing in the following schemes may also be in its salt form, and such salt may include, for example, a corresponding salt exemplified as a salt of a compound of Formula (1). The reactions mentioned below are just examples, and thus the present compound may be optionally prepared by other means based on the knowledge of a person skilled in organic synthesis.

If there is a functional group that needs to be protected in preparation processes mentioned below, the functional group may be protected as appropriate and then deprotected after completing a reaction or reaction sequences to obtain a desired compound, even though the use of any protecting group is not specifically indicated.

The protecting group used herein includes, for example, general protecting groups described in T. W. Greene and P. G. M. Wuts, "*Protective Groups in Organic Synthesis*", 3rd Ed., John Wiley and Sons, inc., New York (1999). In more detail, a protecting group for an amino group includes, for example, benzyloxycarbonyl, tert-butoxycarbonyl, acetyl, and benzyl. A protecting group for a hydroxy group includes, for example, trialkylsilyl, acetyl, and benzyl.

The protection and deprotection can be carried out by conventional means in organic synthetic chemistry (for example, means described in T. W. Greene and P. G. M. Wuts, "*Protective Groups in Organic Synthesis*", 3rd Ed., John Wiley and Sons, inc., New York (1999)), or similar means to them.

Preparation Process 1

The compound of Formula (1a), among compounds of Formula (1), can be prepared, for example, by the following process:

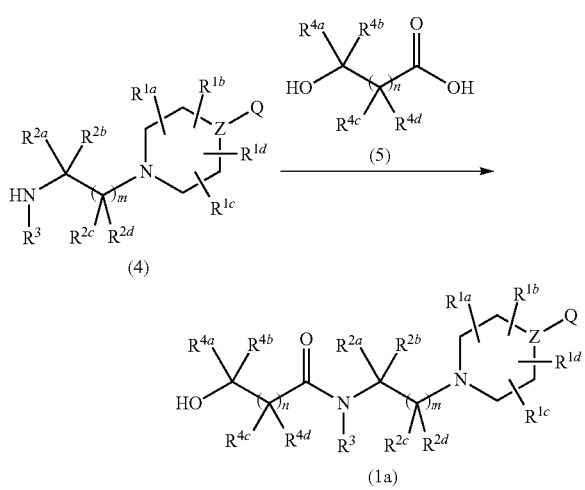

wherein Z, m, n, $R^{1a}$, $R^{1b}$, $R^{1c}$, $R^{1d}$, $R^{2a}$, $R^{2b}$, $R^{2c}$, $R^{2d}$, $R^3$, $R^{4a}$, $R^{4b}$, $R^{4c}$, $R^{4d}$, and Ring Q are as defined in the above Item [1].

Compound (1a) is prepared by reacting Compound (4) and carboxylic acid of Formula (5) in a suitable inert solvent in the presence of a suitable condensing agent. The reaction may be carried out in the presence of a suitable base. The reaction temperature generally ranges from about −20° C. to the boiling point of a solvent used herein. The reaction time depends on reaction conditions such as the reaction temperature, a condensing agent used herein, starting materials, and a solvent used herein, and generally ranges from 10 minutes to 48 hours.

Examples of condensing agents used herein include dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium hexafluorophosphate (BOP), diphenylphosphonyl amide (DPPA), N,N-carbonyldiimidazole (CDI), benzotriazol-1-yl-N,N,N',N'-tetramethyluronium hexafluorophosphate (HBTU), and O-(7-azabenzotriazol-1-yl)-N,N,N',N'-tetramethyluronium hexafluorophosphate (HATU).

As necessary, additives may be added, such as N-hydroxysuccinimide (HOSu), 1-hydroxybenzotriazole (HOBt), 3 hydroxy-4-oxo-3,4-dihydro-1,2,3-benzotriazine (HOOBt).

Examples of bases used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; and metal alkoxides such as sodium methoxide and potassium tert-butoxide.

Examples of inert solvents used herein include halogenated hydrocarbons such as chloroform and dichloromethane; aromatic hydrocarbons such as benzene and toluene; ether solvents such as diethyl ether, tetrahydrofuran (THF), and 1,4-dioxane; aprotic polar solvents such as acetonitrile, acetone, methylethyl ketone, dimethylformamide, N-methyl-2-pyrrolidinone, and dimethylsulfoxide; basic solvents such as pyridine; and mixture solvents thereof.

Preparation Process 2

Among compounds of Formula (4), the compound of Formula (4a) can be prepared, for example, by the following process.

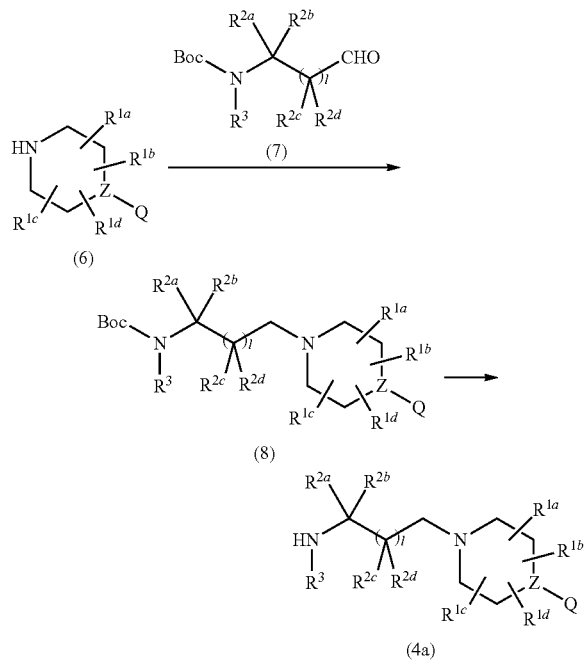

In the scheme, Z, $R^{1a}$, $R^{1b}$, $R^{1c}$, $R^{1d}$, $R^{2a}$, $R^{2b}$, $R^{2c}$, $R^{2d}$, $R^3$, and Ring Q are as defined in the above Item [1]; and l is 0, 1, 2, or 3.

Compound (8) can be prepared by reacting Compound (6) and an aldehyde of Formula (7) under reductive amination with a suitable reducing agent in a suitable inert solvent. The reaction may be carried out in the presence of a suitable base or acid, as necessary. The reaction temperature generally ranges from about –20° C. to the boiling point of a solvent used herein. The reaction time depends on reaction conditions such as the reaction temperature, a reducing agent used herein, starting materials, and a solvent used herein, and generally ranges from 10 minutes to 48 hours.

Examples of reducing agents used herein include complex hydride compounds such as sodium triacetoxyborohydride, lithium aluminum hydride, sodium borohydride, and sodium cyanoborohydride; and borane complexes such as borane-dimethyl sulfide complex and borane-tetrahydrofuran complex.

Examples of bases used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; and metal alkoxides such as sodium methoxide and potassium tert-butoxide.

Examples of acids used herein include organic acids such as acetic acid, trifluoroacetic acid, and methanesulfonic acid; and inorganic acids such as hydrochloric acid and sulfuric acid.

Examples of inert solvents used herein include water; acetonitrile; halogenated hydrocarbons such as chloroform and dichloromethane; aromatic hydrocarbons such as benzene and toluene; ether solvents such as 1,2-dimethoxyethane, tetrahydrofuran, and 1,4-dioxane; alcohol solvents such as methanol, ethanol, and 2-propanol; aprotic polar solvents such as dimethylformamide and N-methyl-2-pyrrolidinone; and mixture solvents thereof.

Compound (4a) can be prepared by treating Compound (8) with a suitable acid in a suitable inert solvent. The reaction temperature generally ranges from –20° C. to the boiling point of a solvent used used herein. The reaction time depends on reaction conditions such as the reaction temperature, an acid used herein, starting materials, and a solvent used herein, and generally ranges from 10 minutes to 48 hours.

Examples of acids used herein include organic acids such as trifluoroacetic acid; and inorganic acids such as hydrochloric acid and sulfuric acid.

Examples of inert solvents used herein include halogenated hydrocarbons such as chloroform and dichloromethane; aromatic hydrocarbons such as benzene and toluene; ether solvents such as diethyl ether, tetrahydrofuran, 1,4-dioxane, and 1,2-dimethoxyethane; lower alcohols such as methanol, ethanol, and 2-propanol; and aprotic polar solvents such as acetonitrile, dimethylformamide, N-methyl-2-pyrrolidinone, and dimethylsulfoxide; and mixture solvents thereof.

Preparation Process 3

The compound of Formula (8) can be prepared, for example, by the following process.

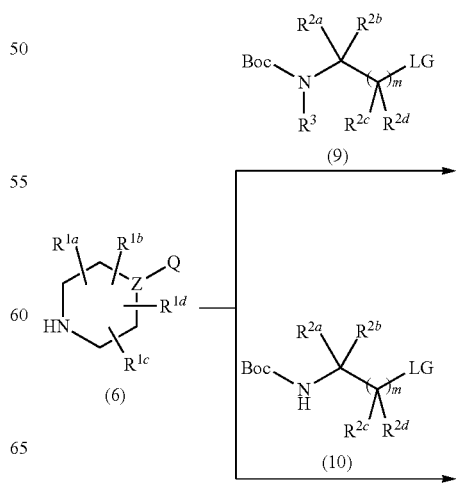

-continued

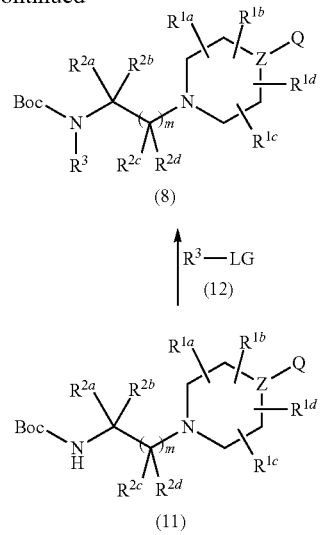

In the scheme, Z, m, $R^{1a}$, $R^{1b}$, $R^{1c}$, $R^{1d}$, $R^{2a}$, $R^{2b}$, $R^{2c}$, $R^{2d}$, $R^3$, and Ring Q are as defined in the above Item [1]; LG is a leaving group such as iodine, bromine, chlorine, substituted sulfonyl (e.g., methanesulfonyl and p-toluenesulfonyl).

Compound (8) can be prepared by reacting Compound (6) with the alkylating agent of Formula (9) in a suitable inert solvent. The reaction may be carried out in the presence of a suitable base, as necessary, and further in the presence of a suitable phase transfer catalyst. The reaction temperature generally ranges from about −20° C. to the boiling point of a solvent used herein. The reaction time depends on reaction conditions such as the reaction temperature, a base used herein, starting materials, and a solvent used herein, and generally ranges from 10 minutes to 48 hours.

Examples of bases used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; and metal alkoxides such as sodium methoxide and potassium tert-butoxide.

Examples of phase transfer catalysts used herein include tetrabutylammonium hydrogen sulfate.

Examples of inert solvents used herein include halogenated hydrocarbons such as chloroform and dichloromethane; aromatic hydrocarbons such as benzene and toluene; ether solvents such as diethyl ether, tetrahydrofuran (THF), and 1,4-dioxane; lower alcohols such as methanol, ethanol, and 2-propanol; aprotic polar solvents such as acetonitrile, acetone, methylethyl ketone, dimethylformamide, N-methyl-2-pyrrolidinone, and dimethylsulfoxide; and mixture solvent thereof.

Compound (11) can be prepared by reacting Compound (6) with the alkylating agent of Formula (10) in a suitable inert solvent. The reaction may be carried out in the presence of a suitable base as necessary, and further in the presence of a suitable phase transfer catalyst. The reaction temperature generally ranges from about −20° C. to the boiling point of a solvent used herein. The reaction time depends on reaction conditions such as the reaction temperature, a base used herein, starting materials, and a solvent used herein, and generally ranges from 10 minutes to 48 hours.

Examples of bases used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; and metal alkoxides such as sodium methoxide and potassium tert-butoxide.

Examples of phase transfer catalysts used herein include tetrabutylammonium hydrogen sulfate.

Examples of inert solvents used herein include halogenated hydrocarbons such as chloroform and dichloromethane; aromatic hydrocarbons such as benzene and toluene; ether solvents such as diethyl ether, tetrahydrofuran (THF), and 1,4-dioxane; lower alcohols such as methanol, ethanol, and 2-propanol; aprotic polar solvents such as acetonitrile, acetone, methylethyl ketone, dimethylformamide, N-methyl-2-pyrrolidinone, and dimethylsulfoxide; and mixture solvents thereof.

Compound (8) can be prepared by reacting Compound (11) with the alkylating agent of Formula (12) in a suitable inert solvent. The reaction may be carried out in the presence of a suitable base as necessary, and further in the presence of a suitable phase transfer catalyst. The reaction temperature generally ranges from about −20° C. to the boiling point of a solvent used herein. The reaction time depends on reaction conditions such as the reaction temperature, a base used herein, starting materials, and a solvent used herein, and generally ranges from 10 minutes to 48 hours.

Examples of bases used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; and metal alkoxides such as sodium methoxide and potassium tert-butoxide.

Examples of phase transfer catalysts used herein include tetrabutylammonium hydrogen sulfate.

Examples of inert solvents used herein include halogenated hydrocarbons such as chloroform and dichloromethane; aromatic hydrocarbons such as benzene and toluene; ether solvents such as diethyl ether, tetrahydrofuran (THF), and 1,4-dioxane; lower alcohols such as methanol, ethanol, and 2-propanol; aprotic polar solvents such as acetonitrile, acetone, methylethyl ketone, dimethylformamide, N-methyl-2-pyrrolidinone, and dimethylsulfoxide; and mixture solvents thereof.

Preparation Process 4

Among compounds of Formula (1), the compound of Formula (1f) can be prepared, for example, by the following process.

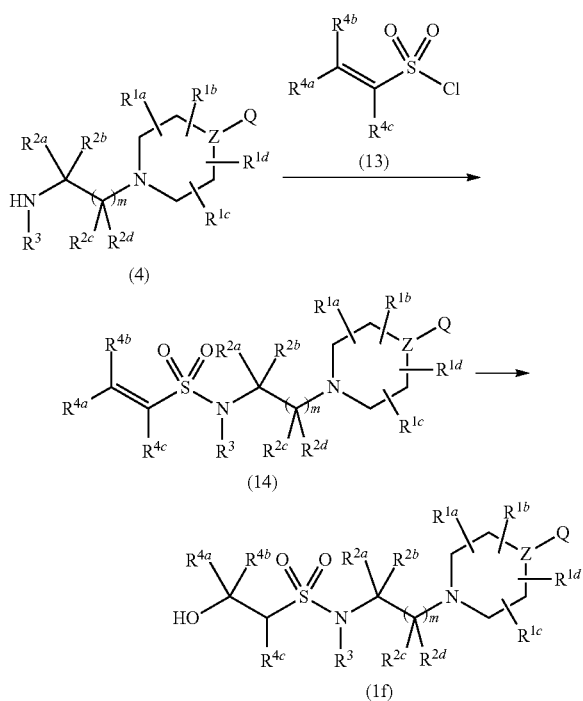

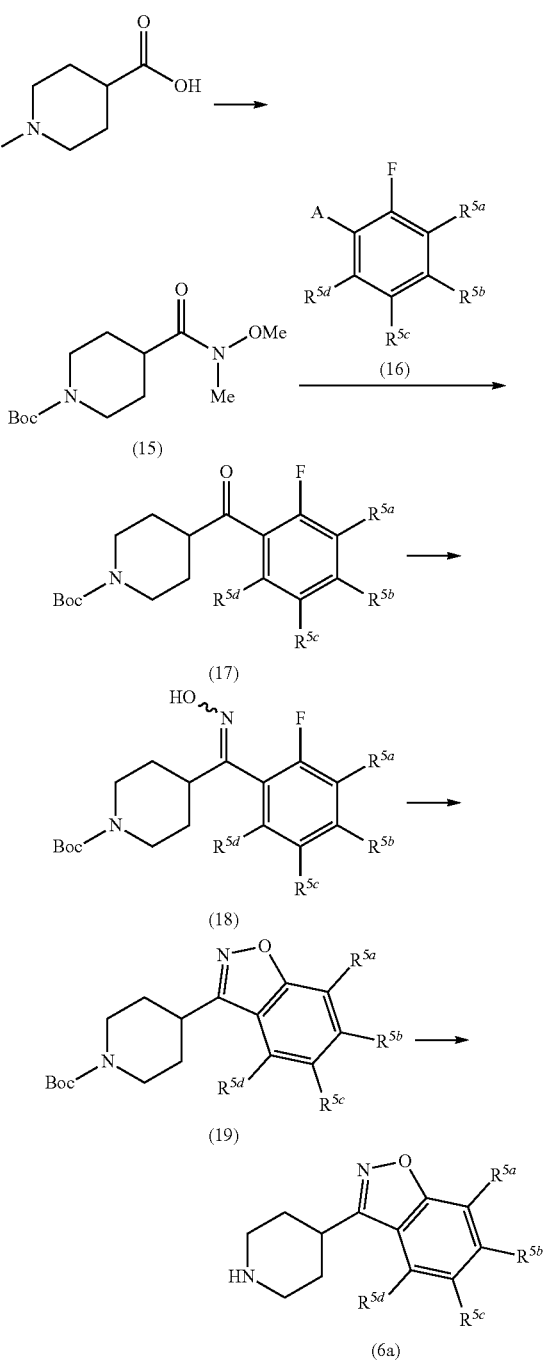

In the scheme, Z, m, $R^{1a}$, $R^{1b}$, $R^{1c}$, $R^{1d}$, $R^{2a}$, $R^{2b}$, $R^{2c}$, $R^{2d}$, $R^3$, $R^{4a}$, $R^{4b}$, $R^{4c}$, and Ring Q are as defined in the above Item [1].

Compound (14) can be prepared by reacting Compound (4) and sulfonyl chloride of Formula (13) in the presence of a suitable inert solvent. The reaction may be carried out in the presence of a suitable base. The reaction temperature generally ranges from about −20° C. to the boiling point of a solvent used herein. The reaction time depends on reaction conditions such as the reaction temperature, starting materials used herein, and a solvent, and generally ranges from 10 minutes to 48 hours.

Examples of bases used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; and metal alkoxides such as sodium methoxide and potassium tert-butoxide.

Examples of inert solvents used herein include halogenated hydrocarbons such as chloroform and dichloromethane; aromatic hydrocarbons such as benzene and toluene; ether solvents such as diethyl ether, tetrahydrofuran (THF), and 1,4-dioxane; aprotic polar solvents such as acetonitrile, acetone, methylethyl ketone, dimethylformamide, N-methyl-2-pyrrolidinone, and dimethylsulfoxide; basic solvents such as pyridine; and mixture solvents thereof.

Compound (1f) can be prepared by reacting Compound (14) with a hydroxide such as tetrabuthylammonium hydroxide and sodium hydroxide in a suitable inert solvent. The reaction temperature generally ranges from about −20° C. to the boiling point of a solvent used herein. The reaction time depends on reaction conditions such as the reaction temperature, starting materials used herein, and a solvent used herein, and generally ranges from 10 minutes to 48 hours.

Examples of inert solvents used herein include aromatic hydrocarbons such as benzene and toluene; ether solvents such as diethyl ether, tetrahydrofuran (THF), and 1,4-dioxane; aprotic polar solvents such as acetonitrile, acetone, methylethyl ketone, dimethylformamide, N-methyl-2-pyrrolidinone, and dimethylsulfoxide; and mixture solvents thereof.

Preparation Process 5

Among compounds of Formula (6), the compound of Formula (6a) can be prepared, for example, by the following process.

In the scheme, $R^{5a}$, $R^{5b}$, $R^{5c}$, and $R^{5d}$ are as defined in the above Item [1]; and A is iodine, bromine, or chlorine.

Compound (15) can be prepared by reacting 1-(tert-butoxycarbonyl)piperidine-4-carboxylic acid with N,O-dimethylhydroxylamine or its hydrochloride in the presence of a suitable condensing agent in a suitable inert solvent. The reaction may be carried out in the presence of a suitable base. The reaction temperature generally ranges from about −20° C. to the boiling point of a solvent used herein. The reaction time depends on reaction conditions such as the reaction temperature, a condensing agent used herein, starting materials, and a solvent used herein, and generally ranges from 10 minutes to 48 hours.

Compound (15) can also be prepared by reacting N,O-dimethylhydroxylamine or its salt with an acid halide or acid anhydride which is derived from 1-(tert-butoxycarbonyl)piperidine-4-carboxylic acid, in the presence of a suitable base, in a suitable inert solvent. The reaction temperature generally ranges from about −20° C. to the boiling point of a solvent used herein. The reaction time depends on reaction conditions such as the reaction temperature, a condensing agent used herein, starting materials, and a solvent used herein, and generally ranges from 10 minutes to 48 hours.

Examples of condensing agents used herein include dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium hexafluorophosphate (BOP), diphenylphosphonyl amide (DPPA), N,N-carbonyldiimidazole (CDI), and benzotriazol-1-yl-N,N,N',N'-tetramethyluronium hexafluorophosphate (HBTU). The reaction may be carried out with addition of an additive such as N-hydroxysuccinimide (HOSu), 1-hydroxybenzotriazole (HOBt), and 3-hydroxy-4-oxo-3,4-dihydro-1,2,3-benzotriazine (HOOBt), as necessary.

Examples of bases used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; and metal alkoxides such as sodium methoxide and potassium tert-butoxide.

Examples of inert solvents used herein include halogenated hydrocarbons such as chloroform and dichloromethane; aromatic hydrocarbons such as benzene and toluene; ether solvents such as diethyl ether, tetrahydrofuran (THF), and 1,4-dioxane; aprotic polar solvents such as acetonitrile, acetone, methylethyl ketone, dimethylformamide, N-methyl-2-pyrrolidinone, and dimethylsulfoxide; basic solvents such as pyridine; and mixture solvent thereof.

Compound (17) can be prepared by reacting Compound (15) with a lithiated compound which is produced by treating Compound (16) with an organolithium such as n-butyllithium in a suitable inert solvent. The reaction temperature generally ranges from about −78° C. to the boiling point of a solvent used herein. The reaction time depends on reaction conditions such as the reaction temperature, a reagent used herein, starting materials, and a solvent used herein, and generally ranges from 10 minutes to 48 hours.

Examples of inert solvents used herein include aromatic hydrocarbons such as benzene and toluene; ether solvents such as diethyl ether, tetrahydrofuran (THF), and 1,4-dioxane; and mixture solvents thereof.

Compound (18) can be prepared by reacting Compound (17) with hydroxylamine or a salt thereof in the presence of a suitable base as necessary. The reaction temperature generally ranges from about −20° C. to the boiling point of a solvent used herein. The reaction time depends on the reaction conditions such as the reaction temperature, a base used herein, starting materials, and a solvent used herein, and generally ranges from 10 minutes to 48 hours.

Examples of bases used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; metal alkoxides such as sodium methoxide and potassium tert-butoxide; and sodium acetate.

Examples of solvents used herein include aromatic hydrocarbons such as benzene and toluene; ether solvents such as diethyl ether, tetrahydrofuran (THF), and 1,4-dioxane; lower alcohols such as methanol, ethanol, and 2-propanol; aprotic polar solvents such as dimethylformamide and N-methyl-2-pyrrolidinon; water; and mixture solvents thereof.

Compound (19) can be prepared by treating Compound (18) with a suitable base in a suitable inert solvent. The reaction temperature generally ranges from about −20° C. to the boiling point of a solvent used herein. The reaction time depends on reaction conditions such as the reaction temperature, a base used herein, starting materials, and a solvent used herein, and generally ranges from 10 minutes to 48 hours.

Examples of bases used herein include organic bases such as triethylamine, diisopropylethylamine, and pyridine; inorganic bases such as potassium carbonate, sodium carbonate, cesium carbonate, potassium bicarbonate, sodium bicarbonate, potassium dihydrogenphosphate, dipotassium hydrogenphosphate, potassium phosphate, sodium dihydrogenphosphate, disodium hydrogenphosphate, sodium phosphate, potassium hydroxide, sodium hydroxide, and sodium hydride; and metal alkoxides such as sodium methoxide and potassium tert-butoxide.

Examples of inert solvents used herein include halogenated hydrocarbons such as chloroform and dichloromethane; aromatic hydrocarbons such as benzene and toluene; ether solvents such as diethyl ether, tetrahydrofuran (THF), and 1,4-dioxane; lower alcohols such as methanol, ethanol, and 2-propanol; aprotic polar solvents such as acetonitrile, acetone, methylethyl ketone, dimethylformamide, N-methyl-2-pyrrolidinone, and dimethylsulfoxide; and mixture solvents thereof.

Compound (6a) can be prepared by processing Compound (19) with a suitable acid in a suitable inert solvent. The reaction temperature generally ranges from −20° C. to the boiling point of a solvent used herein. The reaction time depends on reaction conditions such as the reaction temperature, an acid used herein, starting materials, and a solvent used herein, and generally ranges from 10 minutes to 48 hours.

Examples of inert solvents used herein include halogenated hydrocarbons such as chloroform and dichloromethane; aromatic hydrocarbons such as benzene and toluene; ether solvents such as diethyl ether, tetrahydrofuran, 1,4-dioxane, and 1,2-dimethoxyethane; lower alcohols such as methanol, ethanol, and 2-propanol; aprotic polar solvents such as acetonitrile, dimethylformamide, N-methyl-2-pyrrolidinone, and dimethylsulfoxide; and mixture solvents thereof.

Examples of acids used herein include inorganic acids such as hydrochloric acid and sulfuric acid; and organic acids such as trifluoroacetic acid.

The present compound which has a desired functional group at a desired position can be prepared by suitably combining the above preparation processes. The isolation and purification of each intermediate or product in the above preparation processes can be carried out by conventional methods in organic synthesis, for example, by suitably combining filtration, extraction, washing, drying, concentration, crystallization, and various chromatography. Some intermediates may be used in the next step without purification.

Some starting compounds or intermediates in the above preparation processes can exist in a salt form such as hydrochloride depending on reaction conditions, but can be used as it is or in a free form thereof. When a starting compound or an intermediate is obtained in a salt form and it needs to be used or obtained as a free form thereof, it can be transformed to a free form thereof by dissolving or suspending it in a suitable solvent and neutralizing the resulted solution or suspension with a base such as aqueous sodium bicarbonate.

Some compounds of Formula (1) or pharmaceutically acceptable salts thereof can exist as isomers such as tautomer (for example, keto-enol form), regioisomer, geometrical isomer, and optical isomer. The present invention encompasses every possible isomer including the above, and mixtures thereof which have various mixture proportions.

Optical isomers can be resolved by a known isolation method such as a method with an optically-active column and fractional crystallization at a suitable step in the above-mentioned preparation processes. In addition, an optically-active starting material can also be used for starting materials.

In order to obtain a compound of Formula (1) as a salt thereof, when the product is a salt of a compound of Formula (1), the product should be directly purified; or when the product is in a free form of a compound of Formula (1), the product should be dissolved or suspended in an appropriate solvent and then an acid or a base should be added thereto to form a salt thereof.

The present compound has antagonist activity for the $5\text{-HT}_{2A}$ receptor and antagonist activity for the $5\text{-HT}_7$ receptor, and has different mechanism from other existing medicaments for treating mental diseases. The present compound can provide a new option in medication for various mental diseases. Specifically, the present compound is beneficial for the treatment of mental diseases. The present compound is also beneficial for the treatment of central nervous system diseases.

The mental diseases or central nervous system diseases which are expected to be treated effectively include, for example, F00-F09: organic, including symptomatic, mental disorders, F10-F19:

mental and behavioural disorders due to use of psychoactive substance, F20-F29: schizophrenia, schizotypal disorders, and delusional disorders, F30-F39: mood [affective] disorders, F40-F48: neurotic disorders, stress-related disorders, and somatoform disorders, F51: nonorganic sleep disorders, F52: sexual dysfunction, not caused by organic disorder or disease, F84: pervasive developmental disorders, F90-F98: behavioural and emotional disorders with onset usually in childhood and adolescence, G20-G26: extrapyramidal and movement disorders, G30-G32: other degenerative diseases of nervous system, and G47: sleep disorders in International Classification of Diseases, 10th edition (ICD-10).

F00-F09: Organic, including symptomatic, mental disorders include, for example, Alzheimer's disease, vascular dementia, dementia with Lewy bodies, dementia in Parkinson's disease, mental disorders due to other diseases such as brain damage, and other mental disorders due to brain dysfunction and to physical disease.

F10-F19: Mental and behavioural disorders due to use of psychoactive substance include delirium tremens, psychotic disorder, and amnestic syndrome, due to use of various substance.

F20-F29: Schizophrenia, schizotypal disorders, and delusional disorders include paranoid schizophrenia, simple schizophrenia, and delusional disorders.

F30-F39: Mood [affective] disorders include manic episode, bipolar affective disorder, and depressive episode.

F40-F48: Neurotic disorders, stress-related disorders, and somatoform disorders include phobic anxiety disorders, obsessive-compulsive disorder, and somatoform disorders.

F51: Nonorganic sleep disorders include nonorganic insomnia, sleepwalking, and nightmares.

F52: Sexual dysfunction, not caused by organic disorder or disease, includes lack or loss of sexual desire and unspecified sexual dysfunction.

F84: Pervasive developmental disorders include, for example, autism and overactive disorder associated with mental retardation and stereotyped movements.

F90-F98: Hyperkinetic disorders and behavioural and emotional disorders with onset usually in childhood and adolescence include hyperkinetic disorders, conduct disorders, and mixed disorders of conduct and emotions.

G20-G26: Extrapyramidal and movement disorders include Parkinson's disease and secondary Parkinsonism.

G30-G32: Other degenerative diseases of nervous system include Alzheimer's disease, frontotemporal dementia, frontotemporal lobar degeneration, dementia with Lewy bodies, and senile degeneration of brain.

G47: Sleep disorders include disorders of initiating and maintaining sleep [insomnias], disorders of the sleep-wake schedule, narcolepsy, and cataplexy.

The present compound is useful for treatment or prevention of relapse of various symptoms associated with these diseases such as psychopathic symptoms, sleep disorders, depressive symptoms, anxiety symptoms, and cognitive dysfunction.

Serotonin (5-hydroxytryptamine: 5-HT), one of main neurotransmitters in central nervous system, is known to be involved in various brain functions such as emotional reaction and cognitive function. The $5\text{-HT}_{2A}$ receptor, one of 5-HT receptor subtypes, is highly expressed in, for example, cerebral cortex, hippocampus, and raphe nucleus. The $5\text{-HT}_{2A}$ which is expressed in prefrontal cortex is also known to positively regulate a dopamine neural pathway in the ventral tegmental area (Non-Patent Literature 2). That is, inhibiting the $5\text{-HT}_{2A}$ receptor in prefrontal cortex is considered to lead to an inhibitory effect to psychotic symptoms.

The $5\text{-HT}_7$ receptor is extensively expressed in, for example, hypothalamus, thalamus, hippocampus, and raphe nucleus, and involves in a regulation of circadian rhythm in mammals (Non-Patent Literature 9). It is known that defect in circadian rhythm relates to various CNS disorders, especially for depression, seasonal affective disorder, a sleep disorder, shift work syndrome, and jet lag. Drugs having antagonist activity for the $5\text{-HT}_7$ receptor include Lurasidone which is used as a medicament for treating schizophrenia and a bipolar disorder and Vortioxetine which is used for treating major depression. There is, however, no drug having selective antagonist activity for the 5-HT$_7$ receptor.

It is also known that in some animal models, antagonizing the 5-HT$_7$ receptor leads to antidepressant and anxiolytic effect, and improvement effect in cognition function (Non-patent Literature 6, Non-patent Literature 7).

From the above pharmacological knowledge, it is expected that inhibiting the 5-HT$_{2A}$ receptor, along with inhibiting the 5-HT$_7$ receptor would be useful in various neuropsychiatric diseases such as depression, a sleep disorder, and a psychotic symptom. There is no report for a drug which have a selective and potent antagonist activity on both of the 5-HT$_{2A}$ receptor and the 5-HT$_7$ receptor.

The present compound has potent binding affinity to the 5-HT$_{2A}$ receptor and the 5-HT$_7$ receptor (Test 1), and it shows an antagonist activity on both of the 5-HT$_{2A}$ receptor and the 5-HT$_7$ receptor. In a preferred embodiment of the present invention, the present compound can exert a pharmacological effect based on antagonist ability for the 5-HT$_{2A}$ receptor and the 5-HT$_7$ receptor at the blood concentration which do not cause side effect such as extrapyramidal symptom and hyperprolactinemia due to D$_2$ antagonist activity because a binding affinity of the present compound to the 5-HT$_{2A}$ receptor and the 5-HT$_7$ receptor is 100 times higher more more than that to the D$_2$ receptor.

In another preferred embodiment of the present invention, the present compound is expected to have a small effect for cardiovascular system because there is a big difference between the inhibitory concentration of hERG channel which is an express indicator of arrhythmia in long QT, and the express concentration of the expected pharmacological effect (Test 5).

The disappearance half-life ("T$_{1/2}$") of a drug is a factor for determining the frequency of administration to retain its effect. It is thought that plural administrations of a drug per day having short T$_{1/2}$ can cause forgetting to take a medication or unfinishing taking a medication, and can lead to hindering a suitable medication. Furthermore, if the frequency of administration increases, it is concerned that the incidence rate of side effects can increase or the tolerability can decrease in association with high-dose administration. From the viewpoint mentioned above, if a drug having long T$_{1/2}$ is found out, the drug is expected to be a long-acting drug with little concern mentioned above, which can bring in liability relief of medicated patients.

In a preferred embodiment of the present compound, the estimated human disappearance half-life ("T$_{1/2}$") of the present compound is 8 hours or more (Test 4). Thus, it is expected that the drug efficacy can be retained for a long period in human body, the medication adherence of medicated patients can be improved, and a high tolerability can be exhibited at the administration.

The present compound can be orally or parenterally administered. In the case of oral administration, the compound can be administered in commonly-used dosage form. In the case of parenteral administration, the compound can be administered, for example, in a topical administration form, an injection form, a transdermal form, and a nasal form. The oral form or the rectal administration form include, for example, capsule, tablet, pill, powder, cachet, suppository, and liquid. The injection form includes, for example, aseptic solution and suspension. The topical administration form includes, for example, cream, ointment, lotion, and transdermal formulation (e.g., normal patch and matrix).

The above-mentioned dosage forms are prepared with a pharmaceutically acceptable excipient and an additive in a conventional manner. The pharmaceutically acceptable excipient and additive include carrier, binder, flavor, buffer, thickener, colorant, stabilizing agent, emulsifier, dispersant, suspending agent, and preservative.

The pharmaceutically acceptable carrier includes, for example, magnesium carbonate, magnesium stearate, talc, sugar, lactose, pectin, dextrin, starch, gelatin, tragacanth, methylcellulose, sodium carboxymethylcellulose, low-melting-point wax, and cocoa butter. The capsule form can be prepared by filling a capsule with the present compound and a pharmaceutically acceptable carrier. The present compound can be put into a capsule with or without a pharmaceutically acceptable excipient. The cachet can also be prepared in a similar manner.

The injectable liquid form includes solution, suspension, and emulsion, including, for example, water solution and water-propylene glycol solution. The liquid form may comprise water, and also it may be prepared in a solution of polyethylene glycol or/and propylene glycol. The liquid form suitable for oral administration may be prepared by adding the present compound to water and also adding colorant, flavor, stabilizing agent, sweetener, solubilizer, or thickener thereto, as appropriate. Alternatively, the liquid form suitable for oral administration may be prepared by adding the present compound and a dispersant to water and rendering the liquid sticky. The thickener used herein includes, for example, pharmaceutically acceptable natural or synthetic gum, resin, methylcellulose, sodium carboxymethylcellulose, and a known suspending agent.

The dose of each compound can depend on patient's disease, age, body weight, gender, symptom, and the administration route. In general, the present compound is administered to an adult (body weight: 50 kg) by 0.1 to 1000 mg/day, preferably 1 to 300 mg/day, once a day or in 2 to 3 divided doses per day. Or, it may be administered once in a few days to a few weeks.

In order to enhance the effect and/or reduce side effect thereof, the present compound may be used in combination with another drug. For example, the present compound may be used in combination with an antianxiety drug such as a selective serotonin reuptake inhibitor. Hereinafter, a drug with which the present compound may be used in combination is abbreviated as a "concomitant drug".

Examples of the concomitant drug used herein include a drug for treating a developmental disorder such as an autism spectrum disorder and an attention deficit hyperactivity disorder, an antipsychotic drug and a schizophrenic drug, a drug for treating a bipolar disorder, an antidepressant drug, an antianxiety drug, a drug for treating an obsessive-compulsive disorder, a drug for treating a stress disorder such as a post-traumatic stress disorder, a drug for treating a mood disorder, a drug for treating an eating disorder, a drug for treating a sleep disorder such as insomnia, narcolepsy, a sleep apnea syndrome, and a circadian rhythm disorder, a drug for treating a sexual dysfunction, a drug for treating drug dependence, a drug for treating dementia such as Alzheimer's disease, a drug for treating a behavioral and psychological symptom associated with dementia, a cerebral metabolism and circulation improving drug, a drug for treating a movement disorder such as Parkinson's disease, an analgesic drug, an antiepileptic drug, an anticonvulsant, a migraine drug, an anesthetic, and a central stimulant.

The administration interval between the present compound and its concomitant drug is not limited; i.e., the concomitant drug may be administered to a subject patient at the same time as the present compound or at a suitable interval. Or, the present compound and its concomitant drug can be formulated into a combination drug comprising these. The dose of the concomitant drug can be suitably determined based on the clinically-used dose thereof. The combination ratio of the present compound and its concomitant drug can be suitably determined based on its subject patient to be administered, administration route, disease, pathology, and combinations thereof. For example, when the subject patient is a human being, the concomitant drug may be used in 0.01 to 100 parts by weight per one part by weight of the present compound. For the purpose of reducing side effects, a concomitant drug such as an antiemetic drug, a sleep-inducing drug, and an anticonvulsant may be used in combination.

EXAMPLES

The present invention is explained in more detail in the following by referring to Reference examples, Examples, and Tests; however, the scope of the present invention is not limited thereto. Compound names used in Reference examples and Examples are not always based on IUPAC nomenclature system. Abbreviations may be used for brevity, and these abbreviations have same meanings as those described above.

Compounds were identified by proton nuclear magnetic resonance absorption spectroscopy ($^1$H-NMR) or LC-MS. Amino chromatography in Reference examples and Examples were conducted with an amino column from Yamazen Corporation. LC-MS was carried out with various conditions shown in the following table. Retention time (R.T.) denotes the time when a peak of a mass spectrum appears in LC-MS measurement.

| | |
|---|---|
| Analytical apparatus | Shimadzu LCMS-2020 |
| Column | Phenomenex Kinetex 1.7 μm C18 (50 mm × 2.10 mm) |
| Eluent | A: MeOH, B: 0.05% TFA/H$_2$O |
| Gradient condition | 0.0 min; A/B = 30:70<br>0.0 to 1.90 min; A/B = 99:1<br>1.91 to 3.00 min; A/B = 30:70 |
| Flow rate | 0.5 mL/min |
| Wavelength | (UV) 220 nm |
| Column temperature | 40° C. |

Powder x-ray diffraction (powder XRD) measurement was carried out with various conditions shown in the following table.

| | |
|---|---|
| Analytical apparatus | Empyrian (Spectris Co., Ltd.) |
| X ray | CuKα/45 kV/40 mA |
| Divergence slit | 1/4° |
| Solar slit | 0.04 rad |
| Anti-scattering slit | 5.5 mm |
| Step size | 0.013° |
| Scan range | 4 to 40° (2θ) |
| Cumulative time | 100 second/step |
| Measurement temperature | 23° C. (296 K) |

Differential scanning calorimetry (DSC) measurement was carried out with various conditions shown in the following table.

| | |
|---|---|
| Analytical apparatus | DSC2500 or DSCQ1000 (TA Instruments Inc.) |
| Measurement temperature range | 10 to 250° C. |
| Heating rate | 10° C./minutes |
| Container | TzeroPan or Aluminium hermetic pan (Pinhole) |
| Atmosphere gas flow rate | Dry nitrogen: about 50 mL/minutes |

The following abbreviations may be used in the specification.

In NMR data of Reference examples and Examples, the following abbreviation are used.

Me: Methyl

DMF: N,N-Dimethylformamide

THF: Tetrahydrofuran tert-: Tertiary

CDCl$_3$: Deuterated chloroform

DMSO-d$_6$: Deuterated dimethylsulfoxide

Proton nuclear magnetic resonance spectra were measured with FT-NMR spectrometer (300 MHz or 400 MHz, JEOL). The chemical shifts were shown in δ value (ppm). The signs used in NMR denote the following meanings; s is singlet, d is doublet, dd is double doublet, dt is double triplet, t is triplet, q is quartet, m is multiplet, br is broad, brs is broad singlet, and J is the coupling constant.

Example 1

(2R)—N-Ethyl-N-{2-[4-(6-fluoro-1,2-benzoisoxazol-3-yl)piperidin-1-yl]ethyl}-2-hydroxypropanamide

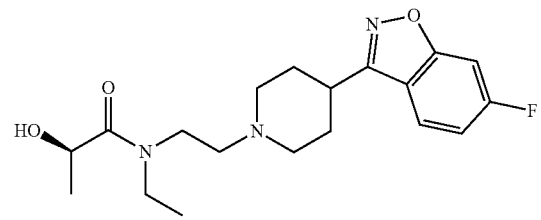 [SMILES: CCN(CCN1CCC(c2noc3cc(F)ccc23)CC1)C(=O)[C@@H](C)O]

To a solution of the compound of Reference example 1 (20.0 mg) in N,N-dimethylformamide (0.5 mL) were added D-lactic acid (6.18 mg), triethylamine (20.8 mg), and 2-(1H-benzo[d][1,2,3]triazol-1-yl)-1,1,3,3-tetramethylisouronium hexafluorophosphate (33.8 mg). The mixture was stirred at room temperature for 16 hours, and water (4.0 mL) was added thereto. The mixture was extracted with chloroform (10 mL×2), dried with anhydrous sodium sulfate, filtered, and concentrated. The concentrated residue was purified by high performance liquid chromatography (column; SEMI-PREPARATIVE C-18 column, separation condition; acetonitrile/trifluoroacetic acid:water/trifluoroacetic acid), and desalted with MP-Carbonate resin to obtain the titled compound (9.73 mg).

LC-MS: R.T.=1.433 min ObsMS=364 [M+1]

Example 2

N-Ethyl-N-{2-[4-(5-fluoro-1H-indazol-1-yl)piperidin-1-yl]ethyl}-3-hydroxypropanamide

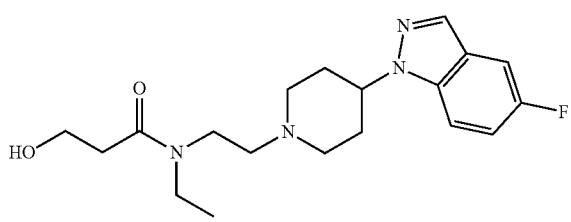 [SMILES: CCN(CCN1CCC(n2ncc3cc(F)ccc32)CC1)C(=O)CCO]

To a suspension of the compound of Reference example 2 (50.0 mg) in dichloromethane (1.0 mL) were added triethylamine (0.077 mL), 30% aqueous 3-hydroxypropionic acid (0.046 mL), and 2-(1H-benzo[d][1,2,3]triazol-1-yl)-1,1,3,3-tetramethylisouronium hexafluorophosphate (67.9 mg). The mixture was stirred at room temperature for 2 hours, and purified by silica gel column chromatography (chloroform/methanol) to obtain the titled compound (43.2 mg).

$^1$H-NMR (400 MHz, CDCl$_3$) δ: 7.89-7.86 (1H, m), 7.37-7.30 (1H, m), 7.29-7.24 (1H, m), 7.11-7.04 (1H, m), 4.44-4.27 (1H, m), 3.87-3.77 (2H, m), 3.72-3.57 (1H, m), 3.51-3.42 (1H, m), 3.42-3.27 (3H, m), 3.17-2.96 (2H, m), 2.59-2.47 (4H, m), 2.36-2.17 (4H, m), 2.05-1.89 (2H, m), 1.18-1.05 (3H, m).

Example 3

(2R)—N-Ethyl-N-{2-[4-(5-fluoro-1H-indazol-1-yl)piperidin-1-yl]ethyl}-2-hydroxypropanamide

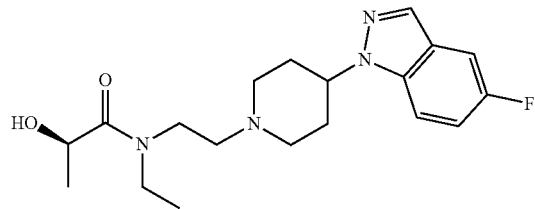 [SMILES: CCN(CCN1CCC(n2ncc3cc(F)ccc32)CC1)C(=O)[C@@H](C)O]

To a suspension of the compound of Reference example 2 (50.0 mg) in dichloromethane (1.0 mL) were added triethylamine (0.077 mL), D-lactic acid (14.9 mg), and 2-(1H-benzo[d][1,2,3]triazol-1-yl)-1,1,3,3-tetramethylisouronium hexafluorophosphate (67.9 mg). The mixture was stirred at room temperature for 4 hours, and purified by silica gel column chromatography (chloroform/methanol) to obtain the titled compound (13.9 mg).

$^1$H-NMR (400 MHz, CDCl$_3$) δ: 7.93 (1H, s), 7.42-7.28 (2H, m), 7.18-7.08 (1H, m), 4.50-4.20 (2H, m), 3.80-3.62 (1H, m), 3.59-2.88 (4H, m), 2.68-2.53 (1H, m), 2.44-2.20 (3H, m), 2.11-1.94 (1H, m), 1.67-1.44 (5H, m), 1.37-1.10 (6H, m).

Examples 4 to 15

According to the method of Example 3, the compounds of Examples 4 to 15 were prepared from the corresponding Reference example compounds.

| Example | Chemical structure | Instrumental analysis data |
|---|---|---|
| 4 | 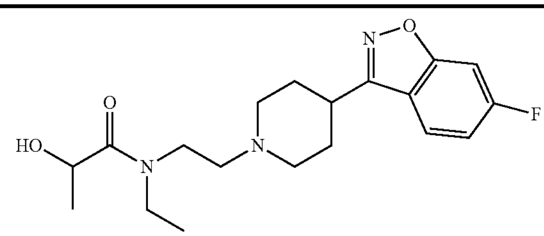 | LC-MS: R.T. = 1.417 min<br>ObsMS = 364 [M + 1] |
| 5 | 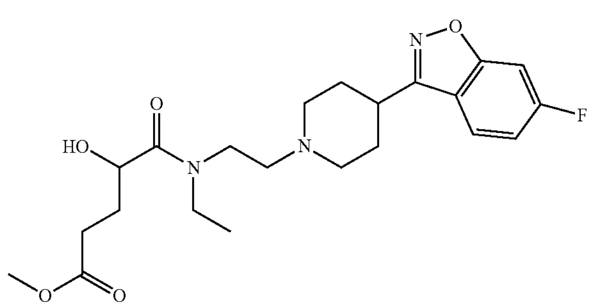 [SMILES: CCN(CCN1CCC(c2noc3cc(F)ccc23)CC1)C(=O)C(O)CCC(=O)OC] | LC-MS: R.T. = 1.517 min<br>ObsMS = 436 [M + 1] |
| 6 | 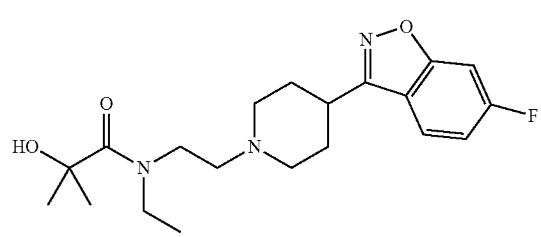 [SMILES: CCN(CCN1CCC(c2noc3cc(F)ccc23)CC1)C(=O)C(C)(C)O] | LC-MS: R.T. = 1.500 min<br>ObsMS = 378 [M + 1] |

-continued

| Example | Chemical structure | Instrumental analysis data |
|---|---|---|
| 7 | 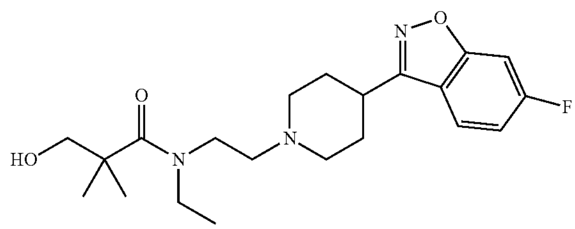 [SMILES: CCN(CCN1CCC(c2noc3cc(F)ccc23)CC1)C(=O)C(C)(C)CO] | LC-MS: R.T. = 1.517 min<br>ObsMS = 392 [M + 1] |
| 8 | 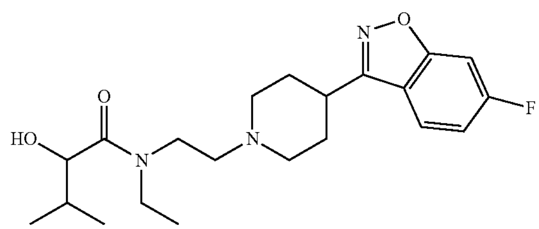 [SMILES: CCN(CCN1CCC(c2noc3cc(F)ccc23)CC1)C(=O)C(O)C(C)C] | LC-MS: R.T. = 1.567 min<br>ObsMS = 392 [M + 1] |
| 9 | 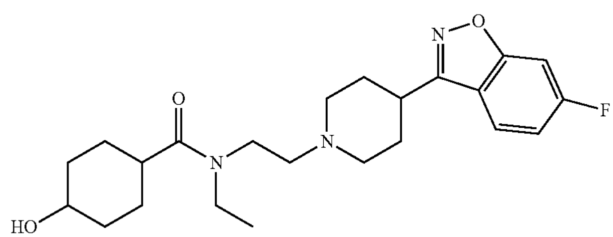 [SMILES: CCN(CCN1CCC(c2noc3cc(F)ccc23)CC1)C(=O)C1CCC(O)CC1] | LC-MS: R.T. = 1.258 min<br>ObsMS = 418 [M + 1] |
| 10 | 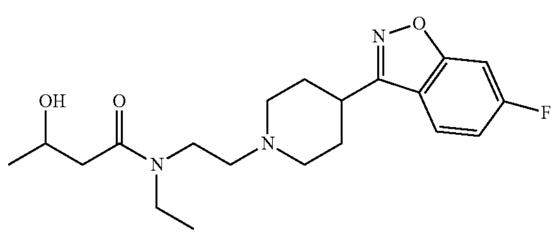 [SMILES: CCN(CCN1CCC(c2noc3cc(F)ccc23)CC1)C(=O)CC(C)O] | LC-MS: R.T. = 1.467 min<br>ObsMS = 378 [M + 1] |
| 11 | 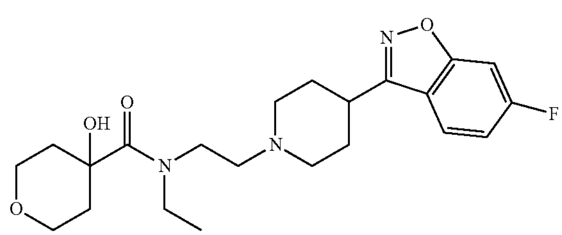 [SMILES: CCN(CCN1CCC(c2noc3cc(F)ccc23)CC1)C(=O)C1(O)CCOCC1] | LC-MS: R.T. = 1.483 min<br>ObsMS = 420 [M + 1] |
| 12 | 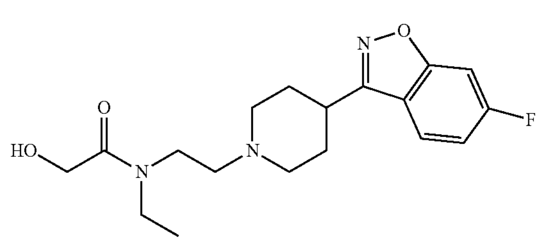 [SMILES: CCN(CCN1CCC(c2noc3cc(F)ccc23)CC1)C(=O)CO] | LC-MS: R.T. = 1.150 min<br>ObsMS = 350 [M + 1] |

| Example | Chemical structure | Instrumental analysis data |
|---|---|---|
| 13 | 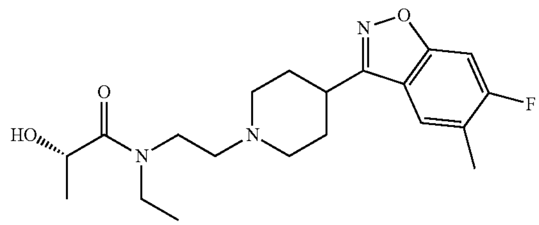 [SMILES: CCN(CCN1CCC(c2noc3cc(F)c(C)cc23)CC1)C(=O)[C@H](C)O] | $^1$H-NMR (400 MHz, CDCl$_3$) δ: 7.58-7.53 (1H, m), 7.16-7.11 (1H, m), 4.48-4.32 (1H, m), 3.75-3.59 (1H, m), 3.56-2.80 (5H, m), 2.65-2.43 (1H, m), 2.31 (3H, s), 2.29-1.85 (5H, m), 1.57-1.44 (4H, m), 1.32-1.27 (3H, m), 1.22-1.06 (3H, m). |
| 14 | 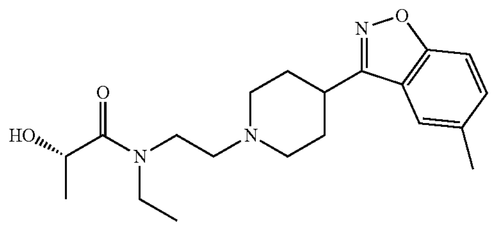 [SMILES: CCN(CCN1CCC(c2noc3ccc(C)cc23)CC1)C(=O)[C@H](C)O] | $^1$H-NMR (400 MHz, CDCl$_3$) δ: 7.52-7.40 (1H, m), 7.37 (1H, d, J = 8.5 Hz), 7.27 (1H, d, J = 8.5 Hz), 4.47-4.26 (1H, m), 3.75-3.57 (1H, m), 3.56-2.88 (6H, m), 2.62-2.45 (2H, m), 2.40 (3H, s), 2.34-1.93 (5H, m), 1.57-1.40 (2H, m), 1.33-1.25 (3H, m), 1.21-1.07 (3H, m). |
| 15 | 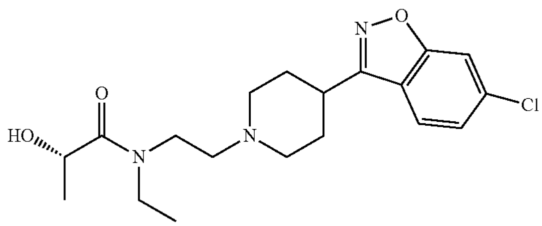 [SMILES: CCN(CCN1CCC(c2noc3cc(Cl)ccc23)CC1)C(=O)[C@H](C)O] | $^1$H-NMR (400 MHz, CDCl$_3$) δ: 7.71-7.60 (1H, m), 7.57-7.54 (1H, m), 7.29-7.25 (1H, m), 4.58-4.28 (1H, m), 3.79-3.62 (1H, m), 3.58-2.87 (6H, m), 2.72-2.49 (2H, m), 2.40-1.93 (5H, m), 1.61-1.43 (2H, m), 1.37-1.29 (3H, m), 1.26-1.08 (3H, m). |

Example 16

(2S)—N-Ethyl-N-{2-[4-(6-fluoro-1,2-benzoisoxazol-3-yl)piperidin-1-yl]ethyl}-2-hydroxypropanamide

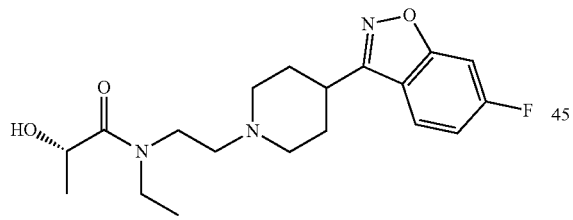

To a suspension of the compound of Reference example 1 (400 mg) in tetrahydrofuran (1.1 mL) were added triethylamine (0.763 mL), L-lactic acid (0.098 mL), and O-(7-azabenzotriazol-1-yl)-N,N,N',N'-tetramethyluronium hexafluorophosphate (0.501 mg). The mixture was stirred at room temperature for 4 hours. To the mixture were added methanol (6.0 mL), 2 mol/L aqueous sodium hydroxide (3.0 mL), and water (1.0 mL). The mixture was stirred at room temperature for 1 hour. Then, water (30 mL) was added thereto, and the mixture was extracted with chloroform (30 mL×2), dried over anhydrous sodium sulfate, filtered, and concentrated. The concentrated residue was purified by silica gel column chromatography (chloroform/methanol) to obtain the titled compound (279 mg).

$^1$H-NMR (400 MHz, CDCl$_3$) δ: 7.72-7.56 (1H, m), 7.17 (1H, dd, J=8.5, 1.8 Hz), 6.99 (1H, td, J=8.8, 1.8 Hz), 4.48-4.32 (1H, m), 3.75-3.59 (1H, m), 3.52-2.86 (7H, m), 2.58-2.44 (2H, m), 2.32-2.11 (2H, m), 2.09-1.87 (4H, m), 1.32-1.25 (3H, m), 1.17 (2H, t, J=7.0 Hz), 1.09 (1H, t, J=7.0 Hz).

Example 17

N-Ethyl-N-{2-[4-(6-fluoro-1,2-benzoisoxazol-3-yl)piperidin-1-yl]ethyl}-3-hydroxypropanamide

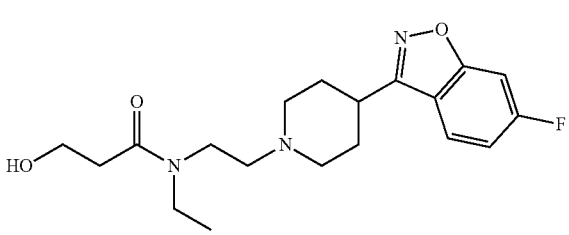 [SMILES: CCN(CCN1CCC(c2noc3cc(F)ccc23)CC1)C(=O)CCO]

To a suspension of the compound of Reference example 1 (3.97 g) in acetonitrile (50 mL) were added triethylamine (6.08 mL), 3-hydroxypropionic acid (4.91 g), and O-(7-azabenzotriazol-1-yl)-N,N,N',N'-tetramethyluronium hexafluorophosphate (6.22 g). The mixture was stirring at room temperature for 2 hours. To the mixture were added methanol (50 mL) and cesium carbonate (14.2 g). The mixture was stirred at 70° C. for 2 hours, and then filtered and concentrated. To the residue was added chloroform (50 mL), and insolubles were filtered out. The eluent was concentrated. The concentrated residue was purified by amino silica gel chromatography (hexane/ethyl acetate and chloroform/methanol), and further purified by silica gel column chromatography (chloroform/methanol) to obtain the titled compound (2.97 g).

¹H-NMR (400 MHz, CD₃OD) δ: 7.93-7.84 (1H, m), 7.42-7.33 (1H, m), 7.20-7.12 (1H, m), 3.88-3.79 (2H, m), 3.62-3.37 (4H, m), 3.23-3.04 (4H, m), 2.69-2.54 (4H, m), 2.42-2.26 (2H, m), 2.15-1.95 (4H, m), 1.29-1.07 (3H, m).
Powder XRD D(°, 2θ±0.2)
8.32, 9.72, 13.30, 13.62, 13.83, 14.24, 16.77, 17.81, 19.89, 19.95, 21.58, 22.02, 24.03, 26.77, 26.84 (Among them, the characteristic 10 peaks were 8.32, 9.72, 13.83, 14.24, 16.77, 19.89, 19.95, 21.58, 22.02, 24.03, and the more characteristic 4 peaks were 8.32, 9.72, 13.83, 16.77.)
DSC
Enthalpy (normalized): 71.71 J/g
Onset x: 67.55° C.

Example 18

N-Ethyl-N-{2-[4-(6-fluoro-1,2-benzoisoxazol-3-yl)piperidin-1-yl]ethyl}-2-hydroxy-3-methoxypropanamide

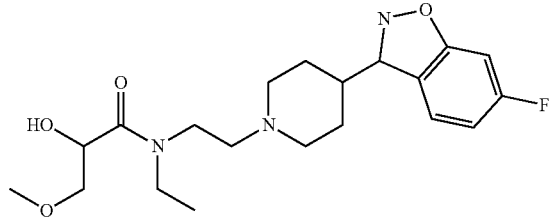

To a suspension of the compound of Reference 1 (70.0 mg) in tetrahydrofuran (1.9 mL) were added triethylamine (0.134 mL), 2-hydroxy-3-methoxypropionic acid (27.7 mg), and O-(7-azabenzotriazol-1-yl)-N,N,N',N'-tetramethyluronium hexafluorophosphate (88.0 mg). The reaction mixture was stirred at room temperature for 3 hours and concentrated. The residue was purified by silica gel column chromatography (chloroform/methanol) to obtain the titled compound (51.7 mg).
¹H-NMR (400 MHz, CDCl₃) δ: 7.78-7.62 (1H, m), 7.24-7.19 (1H, m), 7.03 (1H, td, J=8.9, 2.2 Hz), 4.58-4.47 (1H, m), 3.82-2.89 (13H, m), 2.64-2.48 (2H, m), 2.39-1.96 (6H, m), 1.26-1.08 (3H, m).

Example 19

N-Ethyl-N-{2-[4-(6-fluoro-1H-indazol-3-yl)piperidin-1-yl]ethyl}-2-hydroxypropanamide

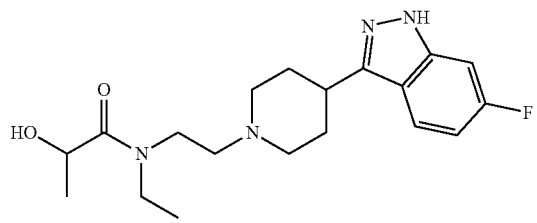

To a solution of the compound of Reference example 6 (400 mg) in N,N-dimethylformamide (4.0 mL) were added diisopropylethylamine 0.577 mL), DL-lactic acid (0.082 mL), and O-(7-azabenzotriazol-1-yl)-N,N,N',N'-tetramethyluronium hexafluorophosphate (628 mg). The mixture was stirred at room temperature for 1 hour. To the reaction mixture was added 2 mol/L aqueous sodium hydroxide (3.0 mL), and the mixture was stirred at room temperature for 1 hour. Then, water (10 mL) was added to the reaction mixture. The mixture was extracted with chloroform (5.0 mL×3), dried over anhydrous sodium sulfate, filtered, and concentrated. The concentrated residue was purified by silica gel column chromatography (chloroform/methanol) to obtain the titled compound (217 mg).
¹H-NMR (400 MHz, CDCl₃) δ: 10.01-9.79 (1H, m), 7.74-7.63 (1H, m), 7.06 (1H, dd, J=9.1, 1.8 Hz), 6.88 (1H, t, J=7.9 Hz), 4.52-4.37 (1H, m), 3.88-3.74 (2H, m), 3.74-3.59 (2H, m), 3.58-3.14 (3H, m), 3.11-2.93 (3H, m), 2.65-2.49 (2H, m), 2.36-1.95 (5H, m), 1.38-1.30 (3H, m), 1.26-1.10 (3H, m).

Example 20

(2S)—N-Ethyl-N-{2-[4-(6-fluoro-1H-indol-3-yl)piperidin-1-yl]ethyl}-2-hydroxypropanamide

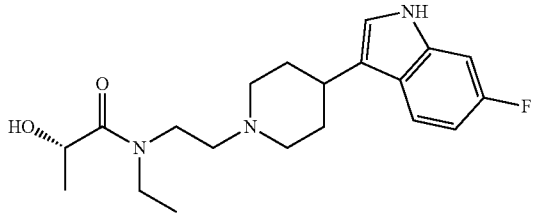 [SMILES: CCN(CCN1CCC(c2c[nH]c3cc(F)ccc23)CC1)C(=O)[C@H](C)O]

To a suspension of the compound of Reference example 7 (30.0 mg) in tetrahydrofuran (0.83 mL) were added triethylamine (0.0575 mL), L-lactic acid (8.95 mg), and O-(7-azabenzotriazol-1-yl)-N,N,N',N'-tetramethyluronium hexafluorophosphate (37.8 mg). The mixture was stirred at room temperature for 2 hours. To the reaction mixture were added methanol (0.8 mL) and 2 mol/L aqueous sodium hydroxide (0.4 mL). The mixture was stirred at room temperature for 30 minutes. The reaction mixture was concentrated, and chloroform (10 mL) was added thereto. The mixture was dried over anhydrous sodium sulfate, filtered, and concentrated. The concentrated residue was purified by silica gel column chromatography (chloroform/methanol) to obtain the titled compound (24.3 mg).
¹H-NMR (400 MHz, CDCl₃) δ: 8.01 (1H, s), 7.45 (1H, dd, J=8.5, 5.5 Hz), 6.97 (1H, dd, J=9.8, 2.4 Hz), 6.87 (1H, s), 6.82-6.77 (1H, m), 4.47-4.32 (1H, m), 3.77-2.87 (6H, m), 2.79-2.68 (1H, m), 2.60-2.44 (2H, m), 2.30-2.13 (2H, m), 2.06-1.67 (4H, m), 1.33-1.25 (3H, m), 1.22-1.06 (3H, m).

Example 21

(2S)—N-Ethyl-N-{2-[4-(5-fluoro-1H-indazol-1-yl)piperidin-1-yl]ethyl}-2-hydroxypropanamide

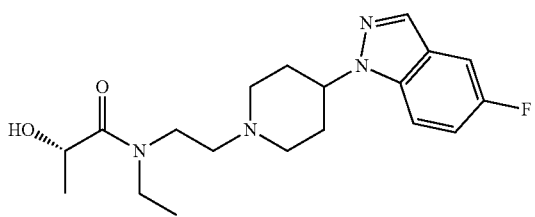 [SMILES: CCN(CCN1CCC(n2ncc3cc(F)ccc32)CC1)C(=O)[C@H](C)O]

To a suspension of the compound of Reference example 2 (400 mg) in tetrahydrofuran (4.0 mL) were added triethylamine (0.768 mL), L-lactic acid (161 mg), and O-(7-azabenzotriazol-1-yl)-N,N,N',N'-tetramethyluronium hexafluorophosphate (786 mg). The mixture was stirred at room temperature for 3 hours. To the reaction mixture was added 15% aqueous sodium hydroxide (4.0 mL), and the mixture was stirred at room temperature for 1 hour. Then, concentrated hydrochloric acid was added thereto until pH of the reaction mixture reached 7, and the mixture was concentrated. The concentrated residue was purified by silica gel column chromatography (chloroform/methanol) to obtain the titled compound (269 mg).

$^1$H-NMR (400 MHz, CDCl$_3$) δ: 7.88 (1H, s), 7.38-7.24 (2H, m), 7.12-7.04 (1H, m), 4.48-4.29 (2H, m), 3.77-3.56 (2H, m), 3.50-2.93 (5H, m), 2.72-2.48 (2H, m), 2.38-2.18 (3H, m), 2.12-1.88 (2H, m), 1.32-1.25 (3H, m), 1.23-1.06 (3H, m).

Example 22

N-Ethyl-2-hydroxy-N-{2-[4-(1H-indol-3-yl)piperidin-1-yl]ethyl}propanamide

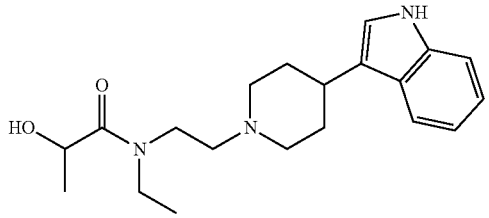 [SMILES: CCN(CCN1CCC(c2c[nH]c3ccccc23)CC1)C(=O)C(C)O]

To a suspension of the compound of Reference example 8 (300 mg) in tetrahydrofuran (8.7 mL) were added triethylamine (0.606 mL), DL-lactic acid (94.0 mg), and O-(7-azabenzotriazol-1-yl)-N,N,N',N'-tetramethyluronium hexafluorophosphate (398 mg). The mixture was stirred at room temperature for 3 hours, and methanol (6.0 mL) and 2 mol/L aqueous sodium hydroxide (3.0 mL) were added thereto. The mixture was stirred at room temperature for 1 hour. Then, the reaction mixture was concentrated, and chloroform (30 mL) was added to the residue. The mixture was dried over anhydrous sodium sulfate, filtered, and concentrated. The concentrated residue was purified by silica gel column chromatography (chloroform/methanol) to obtain the titled compound (258 mg).

$^1$H-NMR (400 MHz, CDCl$_3$) δ: 7.93-7.85 (1H, m), 7.57 (1H, d, J 7.9 Hz), 7.29 (1H, d, J=8.5 Hz), 7.12 (1H, t, J=7.3 Hz), 7.03 (1H, t, J=7.0 Hz), 6.91 (1H, s), 4.47-4.33 (1H, m), 3.80-3.08 (4H, m), 3.05-2.87 (2H, m), 2.83-2.73 (1H, m), 2.59-2.43 (2H, m), 2.30-2.13 (2H, m), 2.06-1.93 (2H, m), 1.83-1.66 (2H, m), 1.29 (3H, t, J=6.4 Hz), 1.21-1.06 (3H, m).

Example 23

(2S)—N-Ethyl-2-hydroxy-N-{2-[4-(1H-indol-3-yl)piperidin-1-yl]ethyl}propanamide

To a suspension of the compound of Reference example 8 (300 mg) in tetrahydrofuran (8.7 mL) were added triethylamine (0.606 mL), L-lactic acid (94.0 mg), and O-(7-azabenzotriazol-1-yl)-N,N,N',N'-tetramethyluronium hexafluorophosphate (398 mg). The mixture was stirred at room temperature for 3 hours, and methanol (6.0 mL) and 2 mol/L aqueous sodium hydroxide (3.0 mL) were added thereto. The mixture was stirred at room temperature for 1 hour. Then, the reaction mixture was concentrated, and chloroform (30 mL) was added to the residue. The mixture was dried over anhydrous sodium sulfate, filtered, and concentrated. The concentrated residue was purified by silica gel column chromatography (chloroform/methanol) to obtain the titled compound (258 mg).

$^1$H-NMR (400 MHz, CDCl$_3$) δ: 8.06-7.92 (1H, m), 7.61 (1H, d, J=7.9 Hz), 7.35 (1H, d, J=7.9 Hz), 7.17 (1H, t, J=7.3 Hz), 7.08 (1H, t, J=7.6 Hz), 6.99-6.94 (1H, m), 4.51-4.36 (1H, m), 3.82-1.74 (16H, m), 1.34 (3H, t, J=6.1 Hz), 1.26-1.11 (3H, m).

Examples 24 to 50

According to the method of Example 23, the compounds of Examples 24 to 50 were prepared from the corresponding Reference example compounds.

| Example | Chemical structure | Instrumental analysis data |
|---|---|---|
| 24 | 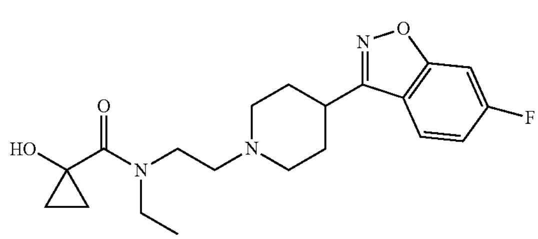 [SMILES: CCN(CCN1CCC(c2noc3cc(F)ccc23)CC1)C(=O)C1(O)CC1] | $^1$H-NMR (400 MHz, CDCl$_3$) δ: 7.74 (1H, dd, J = 8.8, 5.2 Hz), 7.21 (1H, dd, J = 8.5, 1.8 Hz), 7.05-7.00 (1H, m), 3.83-3.74 (2H, m), 3.45-3.31 (2H, m), 3.19-3.01 (3H, m), 2.68-2.59 (2H, m), 2.51-2.37 (2H, m), 2.25-2.09 (2H, m), 2.05-1.95 (2H, m), 1.19-1.06 (6H, m), 0.96-0.90 (2H, m). |

| Example | Chemical structure | Instrumental analysis data |
|---|---|---|
| 25 | 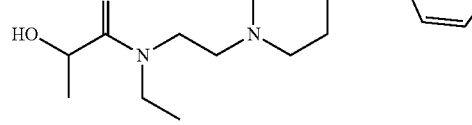 | LC-MS: R.T. = 1.142 min<br>ObsMS = 346 [M + 1] |
| 26 | 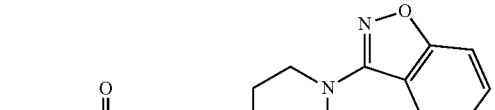 | ¹H-NMR (400 MHz, CDCl₃) δ: 7.65 (1H, d, J = 7.9 Hz), 7.49-7.42 (2H, m), 7.24-7.19 (1H, m), 4.43 (1H, td, J = 13.3, 6.5 Hz), 3.75-3.19 (8H, m), 2.78-2.57 (5H, m), 1.36-1.30 (3H, m), 1.25-1.11 (3H, m). |
| 27 | 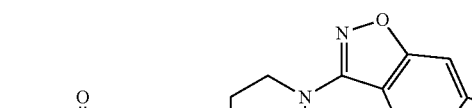 | LC-MS: R.T. = 1.167 min<br>ObsMS = 365 [M + 1] |
| 28 | 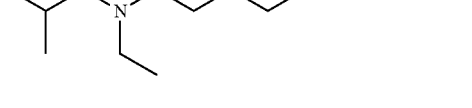 | LC-MS: R.T. = 1.450 min<br>ObsMS = 374 [M + 1] |
| 29 | 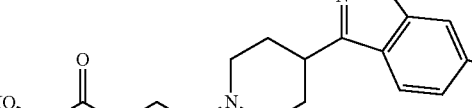 | LC-MS: R.T. = 1.258 min<br>ObsMS = 378 [M + 1] |
| 30 | 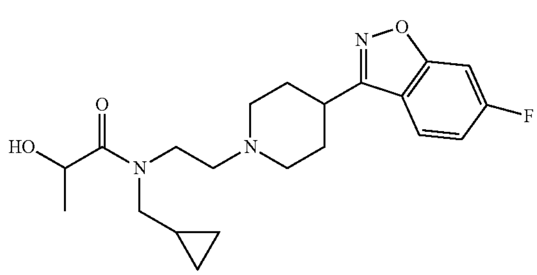 [SMILES: CC(O)C(=O)N(CCN1CCC(c2noc3cc(F)ccc23)CC1)CC1CC1] | LC-MS: R.T. = 1.467 min<br>ObsMS = 390 [M + 1] |

-continued

| Example | Chemical structure | Instrumental analysis data |
|---|---|---|
| 31 | 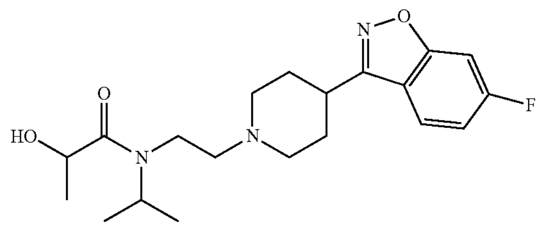 [SMILES: CC(O)C(=O)N(CCN1CCC(c2noc3cc(F)ccc23)CC1)C(C)C] | LC-MS: R.T. = 1.450 min<br>ObsMS = 378 [M + 1] |
| 32 | 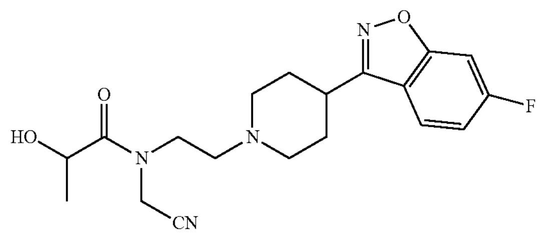 [SMILES: CC(O)C(=O)N(CC#N)CCN1CCC(c2noc3cc(F)ccc23)CC1] | LC-MS: R.T. = 1.314 min<br>ObsMS = 375 [M + 1] |
| 33 | 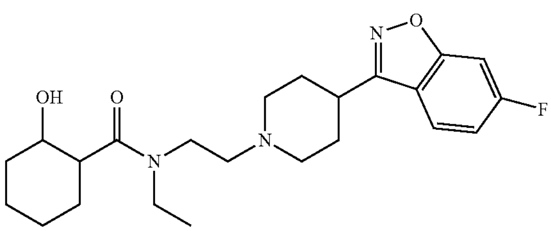 [SMILES: CCN(CCN1CCC(c2noc3cc(F)ccc23)CC1)C(=O)C1CCCCC1O] | LC-MS: R.T. = 1.400 min<br>ObsMS = 418 [M + 1] |
| 34 | 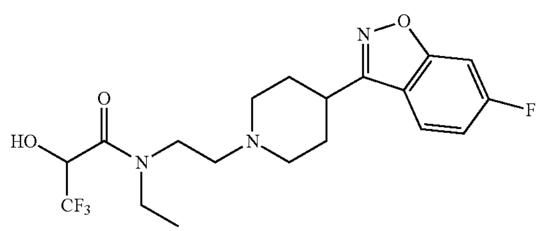 | LC-MS: R.T. = 1.333 min<br>ObsMS = 418 [M + 1] |
| 35 | 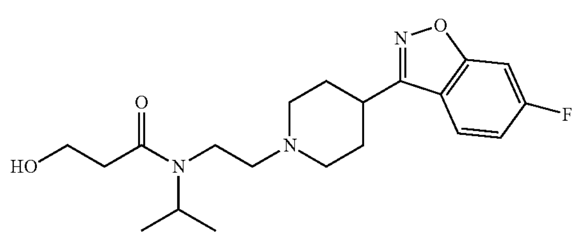 [SMILES: CC(C)N(CCN1CCC(c2noc3cc(F)ccc23)CC1)C(=O)CCO] | $^1$H-NMR (400 MHz, CDCl$_3$) δ: 7.70-7.63 (1H, m), 7.23-7.19 (1H, m), 7.07-7.00 (1H, m), 4.06-3.82 (3H, m), 3.42-3.30 (2H, m), 3.15-2.99 (3H, m), 2.62-2.48 (4H, m), 2.30-2.21 (2H, m), 2.09-2.01 (5H, m), 1.24-1.12 (6H, m). |
| 36 | 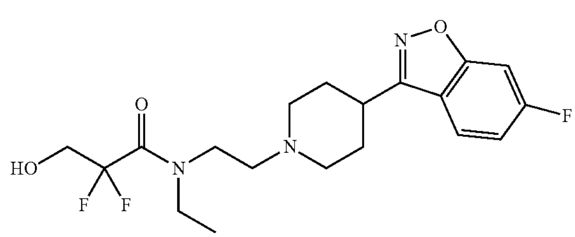 [SMILES: CCN(CCN1CCC(c2noc3cc(F)ccc23)CC1)C(=O)C(F)(F)CO] | $^1$H-NMR (400 MHz, CDCl$_3$) δ: 7.69-7.63 (1H, m), 7.24-7.20 (1H, m), 7.07-7.00 (1H, m), 4.03-3.92 (2H, m), 3.68-3.57 (2H, m), 3.55-3.22 (3H, m), 3.12-3.00 (3H, m), 2.66-2.55 (2H, m), 2.31-2.20 (2H, m), 2.10-1.98 (4H, m), 1.26-1.15 (3H, m). |

| Example | Chemical structure | Instrumental analysis data |
|---|---|---|
| 37 | 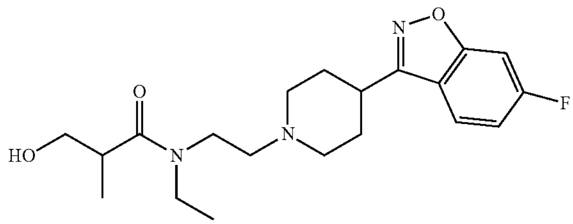 [SMILES: CCN(CCN1CCC(c2noc3cc(F)ccc23)CC1)C(=O)C(C)CO] | ¹H-NMR (400 MHz, CDCl₃) δ: 7.78-7.70 (1H, m), 7.23-7.19 (1H, m), 7.07-7.00 (1H, m), 4.11-4.00 (1H, m), 3.76-3.51 (4H, m), 3.37-2.92 (6H, m), 2.67-1.93 (8H, m), 1.24-1.07 (6H, m). |
| 38 | 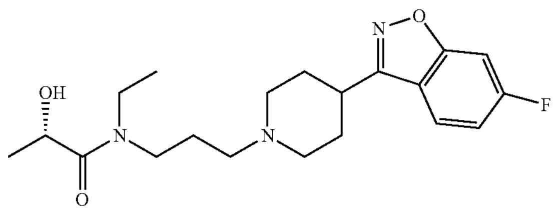 [SMILES: CCN(CCCN1CCC(c2noc3cc(F)ccc23)CC1)C(=O)[C@H](C)O] | ¹H-NMR (400 MHz, CDCl₃) δ: 7.72-7.63 (1H, m), 7.23-7.20 (1H, m), 7.07-7.00 (1H, m), 4.58-4.36 (1H, m), 3.81-2.94 (7H, m), 2.43-2.33 (2H, m), 2.20-1.98 (6H, m), 1.84-1.63 (3H, m), 1.35-1.30 (3H, m), 1.24-1.10 (3H, m). |
| 39 | 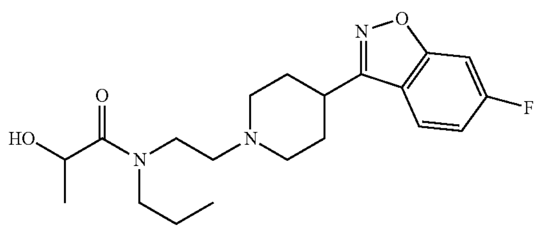 [SMILES: CCCN(CCN1CCC(c2noc3cc(F)ccc23)CC1)C(=O)C(C)O] | ¹H-NMR (400 MHz, CDCl₃) δ: 7.70-7.56 (1H, m), 7.19-7.14 (1H, m), 7.03-6.95 (1H, m), 4.49-4.33 (1H, m), 3.75-3.43 (2H, m), 3.31-2.81 (6H, m), 2.59-2.44 (2H, m), 2.32-1.88 (6H, m), 1.64-1.47 (2H, m), 1.33-1.22 (3H, m), 0.90-0.80 (3H, m). |
| 40 | 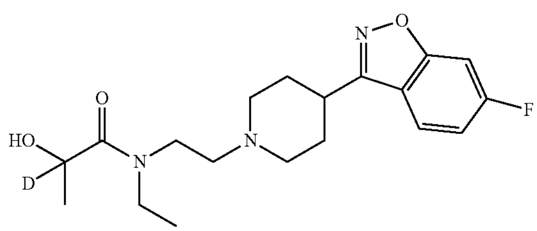 [SMILES: [2H]C(C)(O)C(=O)N(CC)CCN1CCC(c2noc3cc(F)ccc23)CC1] | ¹H-NMR (400 MHz, CDCl₃) δ: 7.75-7.62 (1H, m), 7.23-7.20 (1H, m), 7.07-7.00 (1H, m), 3.75-2.92 (8H, m), 2.62-2.51 (2H, m), 2.37-1.94 (6H, m), 1.37-1.27 (3H, m), 1.27-1.11 (3H, m). |
| 41 | 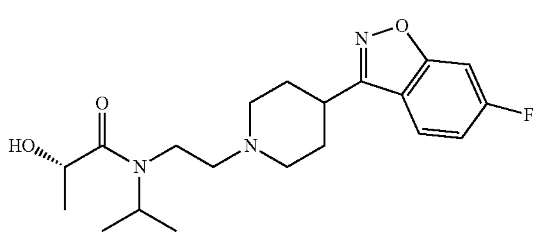 [SMILES: CC(C)N(CCN1CCC(c2noc3cc(F)ccc23)CC1)C(=O)[C@H](C)O] | ¹H-NMR (400 MHz, CDCl₃) δ: 7.74-7.63 (1H, m), 7.23-7.18 (1H, m), 7.08-6.99 (1H, m), 4.53-4.38 (1H, m), 3.97-3.82 (2H, m), 3.54-3.21 (2H, m), 3.19-2.95 (3H, m), 2.63-2.49 (2H, m), 2.34-2.18 (2H, m), 2.15-1.97 (4H, m), 1.38-1.28 (3H, m), 1.28-1.11 (6H, m). |
| 42 | 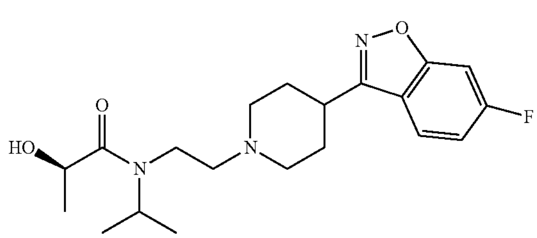 [SMILES: CC(C)N(CCN1CCC(c2noc3cc(F)ccc23)CC1)C(=O)[C@@H](C)O] | ¹H-NMR (400 MHz, CDCl₃) δ: 7.72-7.63 (1H, m), 7.23-7.18 (1H, m), 7.07-7.00 (1H, m), 4.52-4.39 (1H, m), 3.97-3.84 (1H, m), 3.53-3.21 (2H, m), 3.16-2.96 (3H, m), 2.61-2.50 (2H, m), 2.34-2.20 (2H, m), 2.12-1.96 (4H, m), 1.78-1.62 (1H, m), 1.36-1.28 (3H, m), 1.28-1.17 (6H, m). |

-continued

| Example | Chemical structure | Instrumental analysis data |
|---|---|---|
| 43 | 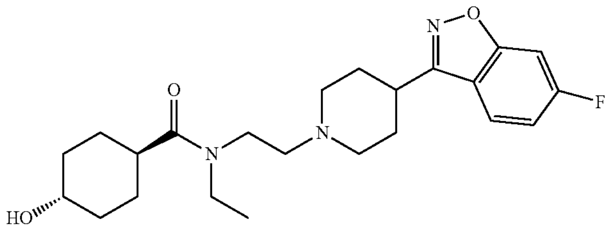 [SMILES: CCN(CCN1CCC(c2noc3cc(F)ccc23)CC1)C(=O)[C@H]1CC[C@H](O)CC1] | ¹H-NMR (400 MHz, CDCl₃) δ: 7.68-7.61 (1H, m), 7.23-7.19 (1H, m), 7.07-6.99 (1H, m), 3.73-3.58 (1H, m), 3.49-3.31 (4H, m), 3.11-2.94 (3H, m), 2.57-2.49 (2H, m), 2.44-2.16 (3H, m), 2.11-1.97 (6H, m), 1.84-1.52 (6H, m), 1.35-1.05 (4H, m). |
| 44 | 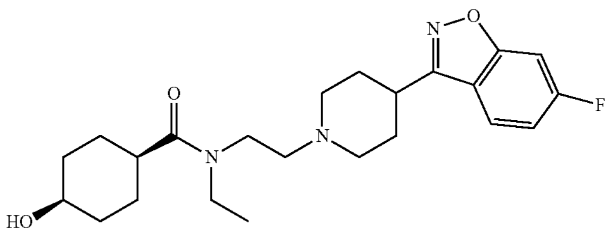 [SMILES: CCN(CCN1CCC(c2noc3cc(F)ccc23)CC1)C(=O)[C@H]1CC[C@@H](O)CC1] | ¹H-NMR (400 MHz, CDCl₃) δ: 7.69-7.61 (1H, m), 7.23-7.18 (1H, m), 7.07-7.00 (1H, m), 4.05-3.97 (1H, m), 3.50-3.31 (4H, m), 3.13-2.97 (3H, m), 2.59-2.42 (3H, m), 2.31-2.17 (2H, m), 2.10-1.81 (7H, m), 1.71-1.42 (6H, m), 1.23-1.05 (3H, m). |
| 45 | 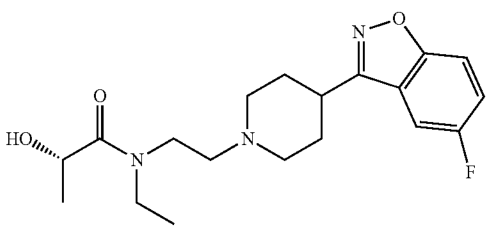 | ¹H-NMR (400 MHz, CDCl₃) δ: 7.52-7.46 (1H, m), 7.44-7.31 (1H, m), 7.30-7.25 (1H, m), 4.57-4.37 (1H, m), 3.80-2.91 (8H, m), 2.74-2.49 (2H, m), 2.39-1.98 (6H, m), 1.37-1.29 (3H, m), 1.26-1.10 (3H, m). |
| 46 | 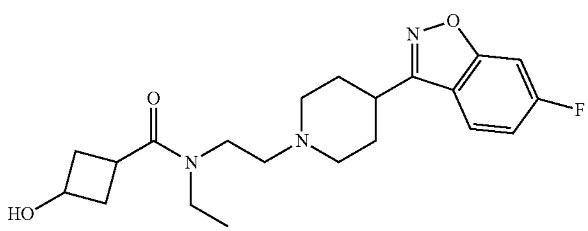 [SMILES: CCN(CCN1CCC(c2noc3cc(F)ccc23)CC1)C(=O)C1CC(O)C1] | ¹H-NMR (400 MHz, CDCl₃) δ: 7.77-7.61 (1H, m), 7.24-7.20 (1H, m), 7.09-7.01 (1H, m), 4.24-4.13 (1H, m), 3.72-1.94 (20H, m), 1.75-1.51 (1H, m), 1.20-1.07 (3H, m). |
| 47 | 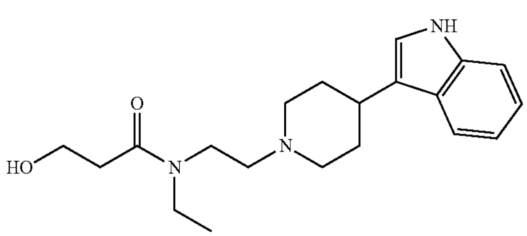 [SMILES: CCN(CCN1CCC(c2c[nH]c3ccccc23)CC1)C(=O)CCO] | ¹H-NMR (400 MHz, CDCl₃) δ: 8.05-7.94 (1H, m), 7.61 (1H, d, J = 7.9 Hz), 7.35 (1H, d, J = 7.9 Hz), 7.17 (1H, t, J = 7.0 Hz), 7.09 (1H, t, J = 7.3 Hz), 6.97 (1H, dd, J = 6.1, 2.4 Hz), 3.92-3.56 (4H, m), 3.46-1.43 (15H, m), 1.24-1.11 (3H, m). |
| 48 | 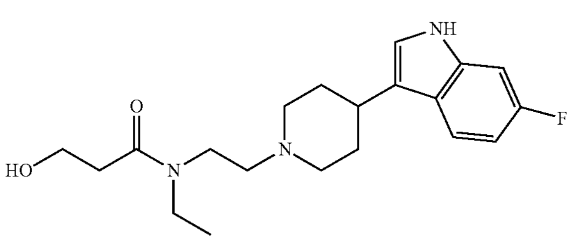 [SMILES: CCN(CCN1CCC(c2c[nH]c3cc(F)ccc23)CC1)C(=O)CCO] | ¹H-NMR (400 MHz, CDCl₃) δ: 8.12-7.97 (1H, m), 7.50 (1H, dd, J = 8.5, 5.5 Hz), 7.02 (1H, dd, J = 9.5, 2.1 Hz), 6.96-6.91 (1H, m), 6.85 (1H, td, J = 9.2, 2.0 Hz), 3.95-3.52 (4H, m), 3.50-1.45 (16H, m), 1.22-1.10 (3H, m). |

-continued

| Example | Chemical structure | Instrumental analysis data |
|---|---|---|
| 49 | 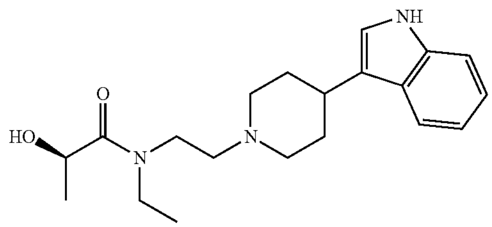 [SMILES: CCN(CCN1CCC(c2c[nH]c3ccccc23)CC1)C(=O)[C@@H](C)O] | ¹H-NMR (400 MHz, CDCl₃) δ: 8.00 (1H, br s), 7.61 (1H, d, J = 7.9 Hz), 7.35 (1H, d, J = 7.9 Hz), 7.17 (1H, t, J = 7.6 Hz), 7.08 (1H, t, J = 7.3 Hz), 6.99-6.94 (1H, m), 4.74-4.34 (2H, m), 3.87-1.71 (15H, m), 1.34 (3H, t, J = 6.4 Hz), 1.25-1.11 (3H, m). |
| 50 | 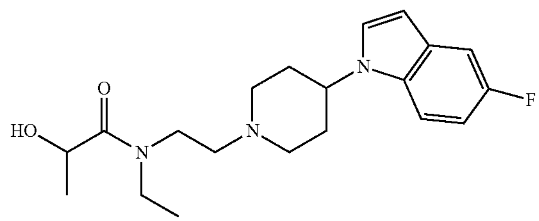 [SMILES: CCN(CCN1CCC(n2ccc3cc(F)ccc32)CC1)C(=O)C(C)O] | ¹H-NMR (400 MHz, CDCl₃) δ: 7.29-7.22 (2H, m), 6.94 (1H, td, J = 9.2, 2.4 Hz), 6.47 (1H, d, J = 3.7 Hz), 4.53-4.12 (2H, m), 3.80-3.64 (2H, m), 3.56-2.88 (5H, m), 2.69-2.54 (2H, m), 2.42-2.25 (2H, m), 2.15-1.98 (4H, m), 1.38-1.33 (3H, m), 1.29-1.13 (3H, m). |

Example 51

N-Ethyl-N-{2-[4-(6-fluoro-1,2-benzoisoxazol-3-yl)piperidin-1-yl]ethyl}-2-hydroxyethane-1-sulfonamide To a solution of the compound of Reference example 23 (636 mg) in tetrahydrofuran (20 mL) was added 10% aqueous tetrabuthylammonium hydroxide (17.3 m). The mixture was stirred at 60° C. for 2 hours, and concentrated. The residue was purified by silica gel column chromatography (chloroform/methanol), and further purified by amino silica gel column chromatography (chloroform/methanol) to obtain the titled compound (330 mg).

¹H-NMR (400 MHz, CDCl₃) δ: 7.79 (1H, dd, J=8.9, 5.2 Hz), 7.22 (1H, dd, J=8.5, 2.4 Hz), 7.04 (1H, td, J=8.9, 2.2 Hz), 5.94 (1H, br s), 4.03-3.95 (2H, m), 3.60-3.53 (2H, m), 3.33-3.24 (4H, m), 3.21-3.09 (3H, m), 2.59-2.52 (2H, m), 2.31-2.13 (4H, m), 2.11-2.00 (2H, m), 1.25 (3H, t, J=7.0 Hz).

Examples 52 to 64

According to the method of Example 51, the compounds of Examples 52 to 64 were prepared from the corresponding Reference example compounds.

| Example | Chemical structure | Instrumental analysis data |
|---|---|---|
| 52 | 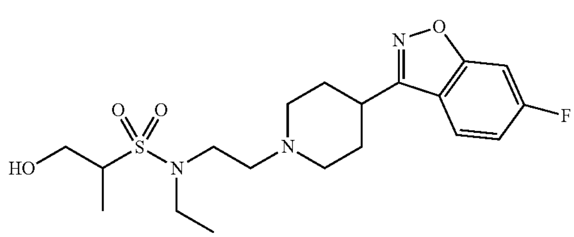 [SMILES: CCN(CCN1CCC(c2noc3cc(F)ccc23)CC1)S(=O)(=O)C(C)CO] | ¹H-NMR (400 MHz, CDCl₃) δ: 7.90-7.81 (1H, m), 7.17 (1H, dd, J = 8.2, 2.1 Hz), 7.07 (1H, td, J = 9.0, 2.2 Hz), 3.65-2.21 (17H, m), 1.67-1.56 (1H, m), 1.43-1.31 (1H, m), 1.26 (3H, d, J = 6.7 Hz), 1.09 (3H, t, J = 7.0 Hz). |
| 53 | 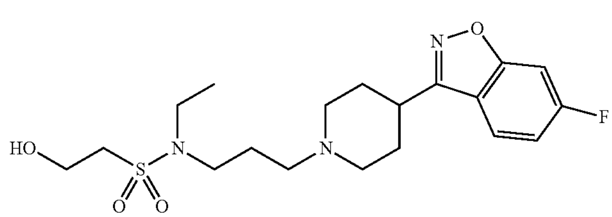 [SMILES: CCN(CCCN1CCC(c2noc3cc(F)ccc23)CC1)S(=O)(=O)CCO] | ¹H-NMR (400 MHz, CDCl₃) δ: 7.69-7.60 (1H, m), 7.19-7.15 (1H, m), 7.04-6.96 (1H, m), 4.03-3.95 (2H, m), 3.32-3.22 (4H, m), 3.16-3.09 (2H, m), 3.09-2.96 (3H, m), 2.92-2.81 (1H, m), 2.47-2.36 (2H, m), 2.27-1.93 (6H, m), 1.87-1.74 (2H, m), 1.17 (3H, t, J = 7.3 Hz). |

| Example | Chemical structure | Instrumental analysis data |
|---|---|---|
| 54 | 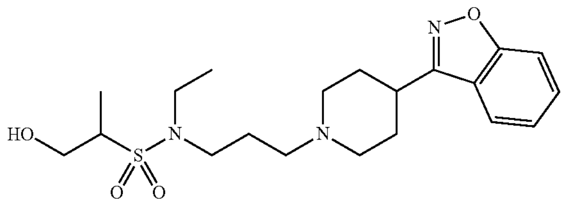 [SMILES: CCN(CCCN1CCC(c2noc3ccccc23)CC1)S(=O)(=O)C(C)CO] | ¹H-NMR (400 MHz, CD₃OD) δ: 7.91-7.88 (1H, m), 7.61-7.58 (2H, m), 7.40-7.32 (1H, m), 3.91 (1H, dd, J = 11.6, 4.9 Hz), 3.68-3.62 (1H, m), 3.39-3.08 (9H, m), 2.52-2.45 (2H, m), 2.31-2.22 (2H, m), 2.16-2.03 (4H, m), 1.92-1.82 (2H, m), 1.35 (3H, d, J = 6.7 Hz), 1.24 (3H, t, J = 7.3 Hz). |
| 55 | 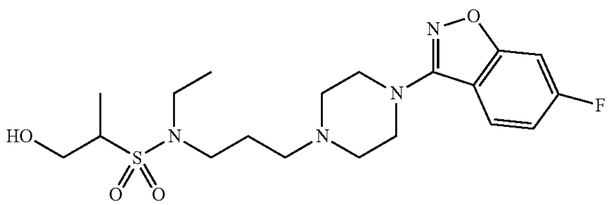 | ¹H-NMR (400 MHz, CD₃OD) δ: 7.89 (1H, dd, J = 8.9, 5.2 Hz), 7.25 (1H, dd, J = 8.9, 2.1 Hz), 7.08 (1H, td, J = 9.2, 2.4 Hz), 3.91 (1H, dd, J = 11.0, 4.9 Hz), 3.67-3.61 (1H, m), 3.58-3.51 (4H, m), 3.40-3.23 (6H, m), 2.72-2.63 (4H, m), 2.52-2.44 (2H, m), 1.92-1.80 (2H, m), 1.35 (3H, d, J = 6.7 Hz), 1.27-1.19 (3H, m). |
| 56 | 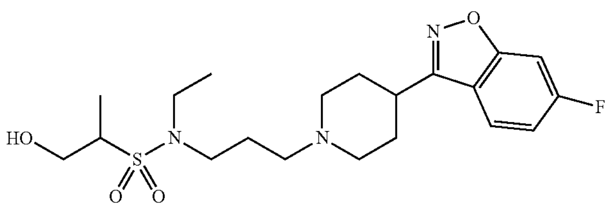 [SMILES: CCN(CCCN1CCC(c2noc3cc(F)ccc23)CC1)S(=O)(=O)C(C)CO] | ¹H-NMR (400 MHz, CD₃OD) δ: 7.91 (1H, dd, J = 8.9, 5.2 Hz), 7.38 (1H, dd, J = 8.9, 2.1 Hz), 7.17 (1H, td, J = 9.0, 2.0 Hz), 3.91 (1H, dd, J = 11.6, 4.9 Hz), 3.64 (1H, dd, J = 11.6, 6.7 Hz), 3.39-3.05 (8H, m), 2.51-2.44 (2H, m), 2.30-2.21 (2H, m), 2.15-1.99 (5H, m), 1.91-1.81 (2H, m), 1.35 (3H, d, J = 6.7 Hz), 1.23 (3H, t, J = 7.0 Hz). |
| 57 | 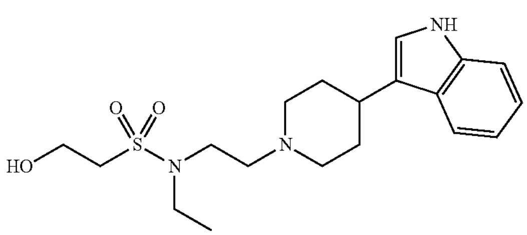 [SMILES: CCN(CCN1CCC(c2c[nH]c3ccccc23)CC1)S(=O)(=O)CCO] | ¹H-NMR (400 MHz, CDCl₃) δ: 7.96 (1H, s), 7.59 (1H, d, J = 7.9 Hz), 7.30 (1H, d, J = 7.9 Hz), 7.15-7.09 (1H, m), 7.07-7.01 (1H, m), 6.96-6.91 (1H, m), 3.96-3.87 (2H, m), 3.72-3.51 (3H, m), 3.35-3.12 (6H, m), 2.93-1.85 (9H, m), 1.25-1.13 (3H, m). |
| 58 | 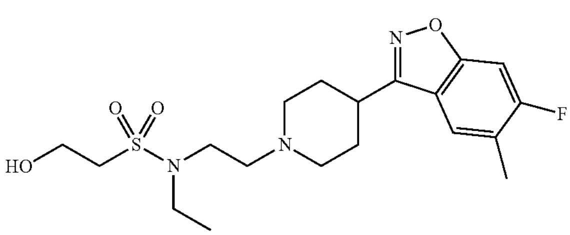 [SMILES: CCN(CCN1CCC(c2noc3cc(F)c(C)cc23)CC1)S(=O)(=O)CCO] | ¹H-NMR (400 MHz, CDCl₃) δ: 7.65 (1H, d, J = 7.3 Hz), 7.18 (1H, d, J = 9.1 Hz), 5.98 (1H, br s), 4.04-3.96 (2H, m), 3.60-3.54 (2H, m), 3.34-3.26 (4H, m), 3.21-3.06 (3H, m), 2.61-2.51 (2H, m), 2.36-2.32 (3H, m), 2.30-2.14 (4H, m), 2.10-1.98 (2H, m), 1.25 (3H, t, J = 7.0 Hz). |
| 59 | 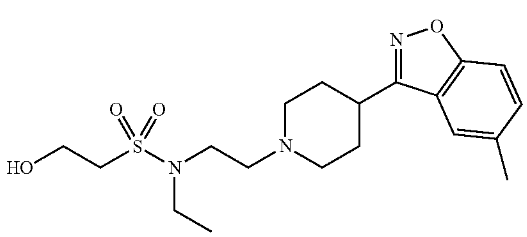 [SMILES: CCN(CCN1CCC(c2noc3ccc(C)cc23)CC1)S(=O)(=O)CCO] | ¹H-NMR (400 MHz, CDCl₃) δ: 7.61 (1H, s), 7.42 (1H, d, J = 8.5 Hz), 7.32 (1H, dd, J = 8.5, 1.8 Hz), 6.13-5.86 (1H, m), 4.04-3.98 (2H, m), 3.61-3.55 (2H, m), 3.37-3.24 (4H, m), 3.23-3.09 (3H, m), 2.62-2.53 (2H, m), 2.45 (3H, s), 2.37-2.17 (4H, m), 2.13-1.99 (2H, m), 1.25 (3H, t, J = 7.0 Hz). |

-continued

| Example | Chemical structure | Instrumental analysis data |
|---|---|---|
| 60 | 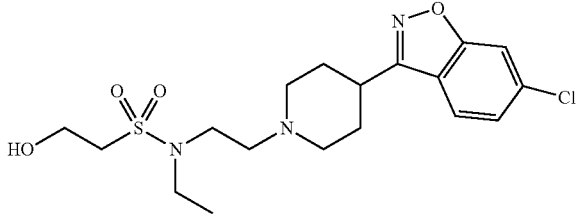 [SMILES: CCN(CCN1CCC(c2noc3cc(Cl)ccc23)CC1)S(=O)(=O)CCO] | ¹H-NMR (400 MHz, CDCl₃) δ: 7.72 (1H, d, J = 8.5 Hz), 7.53-7.49 (1H, m), 7.24-7.20 (1H, m), 5.80 (1H, br s), 4.00-3.90 (2H, m), 3.57-3.48 (2H, m), 3.31-3.18 (4H, m), 3.18-3.05 (3H, m), 2.63-2.44 (2H, m), 2.36-2.08 (4H, m), 2.08-1.96 (2H, m), 1.20 (3H, t, J = 7.0 Hz). |
| 61 | 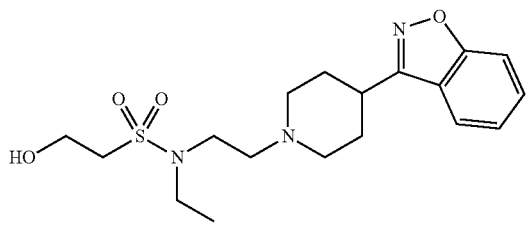 [SMILES: CCN(CCN1CCC(c2noc3ccccc23)CC1)S(=O)(=O)CCO] | ¹H-NMR (400 MHz, CDCl₃) δ: 7.78 (1H, d, J = 7.9 Hz), 7.52-7.44 (2H, m), 7.26-7.20 (1H, m), 5.88 (1H, br s), 3.98-3.92 (2H, m), 3.58-3.49 (2H, m), 3.31-3.19 (4H, m), 3.19-3.05 (3H, m), 2.57-2.49 (2H, m), 2.33-2.12 (4H, m), 2.10-1.98 (2H, m), 1.20 (3H, t, J = 7.0 Hz). |
| 62 | 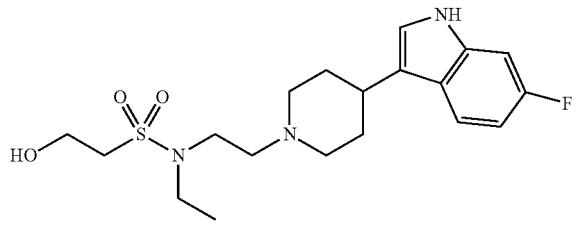 [SMILES: CCN(CCN1CCC(c2c[nH]c3cc(F)ccc23)CC1)S(=O)(=O)CCO] | ¹H-NMR (400 MHz, CDCl₃) δ: 8.06 (1H, s), 7.53 (1H, dd, J = 8.9, 5.2 Hz), 7.03 (1H, dd, J = 9.5, 2.1 Hz), 6.97-6.92 (1H, m), 6.89-6.81 (1H, m), 4.00-3.92 (2H, m), 3.65-3.55 (2H, m), 3.34-3.15 (6H, m), 2.91-1.58 (10H, m), 1.29-1.20 (3H, m). |
| 63 | 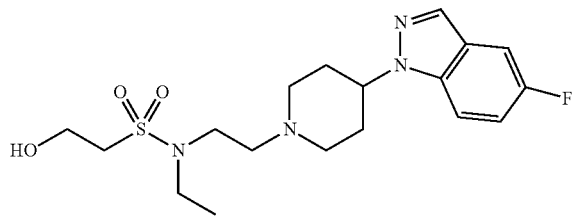 [SMILES: CCN(CCN1CCC(n2ncc3cc(F)ccc32)CC1)S(=O)(=O)CCO] | ¹H-NMR (400 MHz, CDCl₃) δ: 7.92 (1H, s), 7.43 (1H, dd, J = 9.2, 3.7 Hz), 7.33 (1H, dd, J = 8.5, 2.4 Hz), 7.13 (1H, td, J = 9.2, 2.4 Hz), 4.58-4.38 (1H, m), 4.08-4.00 (2H, m), 3.64-3.50 (2H, m), 3.40-3.13 (6H, m), 2.76-2.53 (2H, m), 2.51-2.22 (4H, m), 2.18-1.98 (1H, m), 1.79-1.47 (2H, m), 1.25 (3H, t, J = 7.3 Hz). |
| 64 | 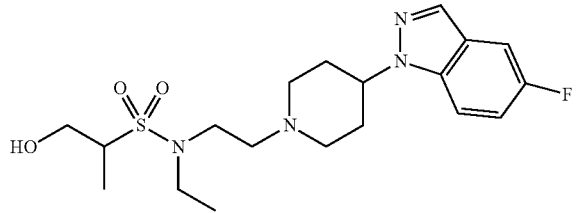 [SMILES: CCN(CCN1CCC(n2ncc3cc(F)ccc32)CC1)S(=O)(=O)C(C)CO] | ¹H-NMR (400 MHz, CDCl₃) δ: 7.92 (1H, s), 7.47-7.39 (1H, m), 7.33 (1H, dd, J = 8.5, 2.4 Hz), 7.17-7.10 (1H, m), 4.55-4.36 (1H, m), 3.98-3.68 (3H, m), 3.52-2.98 (5H, m), 2.79-2.14 (4H, m), 2.14-1.96 (1H, m), 1.69-1.46 (5H, m), 1.34 (3H, d, J = 7.3 Hz), 1.25 (3H, t, J = 7.0 Hz). |

Example 65

3-Amino-N-ethyl-N-{2-[4-(6-fluoro-1,2-benzoisoxazol-3-yl)piperidin-1-yl]ethyl}-2-hydroxypropanamide

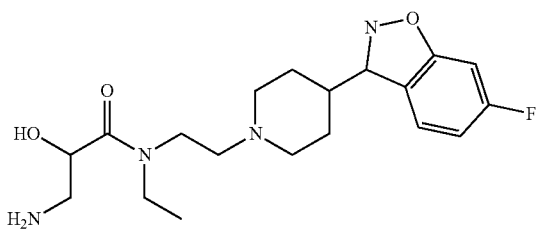

To a solution of 3-((tert-butoxycarbonyl)amino)-2-hydroxypropionic acid (40.6 mg) in N,N-dimethylformamide (2.0 mL) was added O-(7-azabenzotriazol-1-yl)-N,N,N',N'-tetramethyluronium hexafluorophosphate (75.0 mg). The mixture was stirred at room temperature for 1 hour, and triethylamine (0.053 mL) and the compound of Reference example 1 (60.0 mg) were added thereto. The mixture was stirred at room temperature for 3 hours, and water (10 mL) was added thereto. The mixture was extracted with chloroform/methanol (10 mL×6), dried over anhydrous sodium sulfate, filtered, and concentrated. The concentrated residue was purified by silica gel column chromatography (chloroform/methanol). Then, to the resulted compound (50 mg) was added 4 mol/L hydrochloric acid-ethyl acetate (2.0 mL). The mixture was stirred at room temperature for 1 hour, and concentrated. The concentrated residue was purified by amino silica gel column chromatography (chloroform/methanol) to obtain the titled compound (37.0 mg).

$^1$H-NMR (400 MHz, CDCl$_3$) δ: 7.77-7.58 (1H, m), 7.20 (1H, d, J=7.9 Hz), 7.08-6.91 (1H, m), 4.76-4.24 (1H, m), 3.86-2.69 (9H, m), 2.69-2.41 (4H, m), 2.41-1.74 (7H, m), 1.35-0.89 (3H, m).

Examples 66 to 70

According to the method of Example 65, the compounds of Examples 66 to 70 were prepared by the corresponding Reference example compounds.

| Example | Chemical structure | Instrumental analysis data |
| --- | --- | --- |
| 66 | 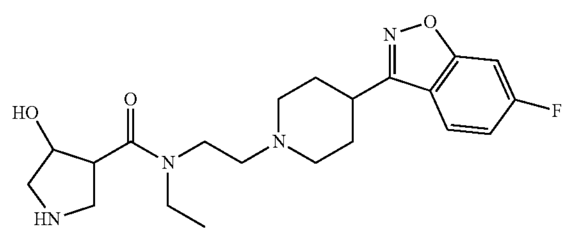 [SMILES: CCN(CCN1CCC(c2noc3cc(F)ccc23)CC1)C(=O)C1CNCC1O] | LC-MS: R.T. = 1.167 min<br>ObsMS = 405 [M + 1] |
| 67 | 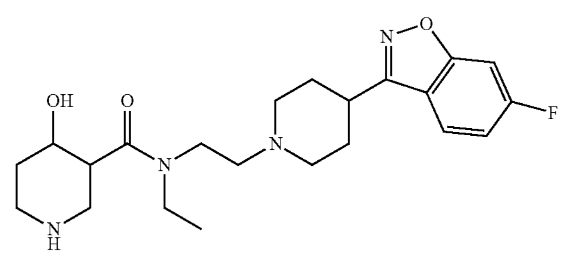 [SMILES: CCN(CCN1CCC(c2noc3cc(F)ccc23)CC1)C(=O)C1CNCCC1O] | LC-MS: R.T. = 1.200 min<br>ObsMS = 419 [M + 1] |
| 68 | 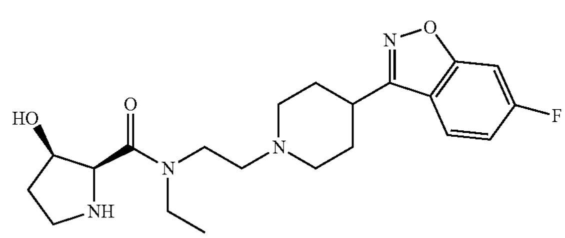 [SMILES: CCN(CCN1CCC(c2noc3cc(F)ccc23)CC1)C(=O)[C@H]1NCC[C@H]1O] | LC-MS: R.T. = 1.200 min<br>ObsMS = 405 [M + 1] |
| 69 | 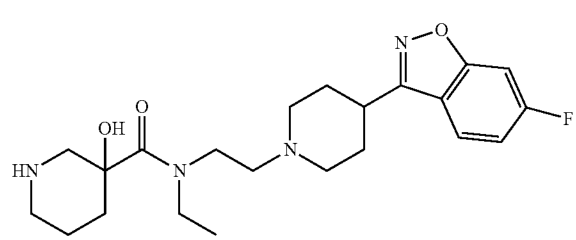 [SMILES: CCN(CCN1CCC(c2noc3cc(F)ccc23)CC1)C(=O)C1(O)CCCNC1] | LC-MS: R.T. = 1.300 min<br>ObsMS = 419 [M + 1] |

| Example | Chemical structure | Instrumental analysis data |
|---|---|---|
| 70 | 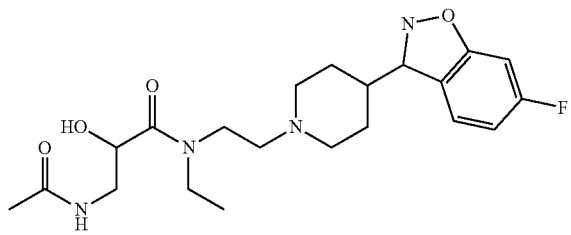 | LC-MS: R.T. = 1.100 min<br>ObsMS = 405 [M + 1] |

Example 71

3-Acetamide-N-ethyl-N-{2-[4-(6-fluoro-1,2-benzo-isoxazol-3-yl)piperidin-1-yl]ethyl}-2-hydroxypropanamide To a solution of the compound of Example 65 (20.0 mg) in tetrahydrofuran (2.0 mL) was added anhydrous acetic acid (0.00598 mL). The mixture was stirred at room temperature for 1 hour. Then, 2 mol/L aqueous sodium hydroxide (0.1 mL) was added thereto, and the mixture was stirred at room temperature for 10 minutes. The reaction mixture was concentrated, and purified by amino silica gel column chromatography (chloroform/methanol) to obtain the titled compound (10.1 mg).

$^1$H-NMR (400 MHz, CDCl$_3$) δ: 7.77-7.55 (1H, m), 7.19-7.14 (1H, m), 7.05-6.97 (1H, m), 6.19-6.01 (1H, m), 4.49-4.34 (1H, m), 4.03-3.47 (4H, m), 3.47-2.84 (6H, m), 2.72-2.48 (2H, m), 2.43-2.19 (2H, m), 2.16-1.97 (4H, m), 1.96-1.90 (3H, m), 1.24-1.06 (3H, m).

Examples 72 to 74

According to the method of Example 71, the compounds of Examples 72 to 74 were prepared from the corresponding Reference example compounds.

| Example | Chemical structure | Instrumental analysis data |
|---|---|---|
| 72 | 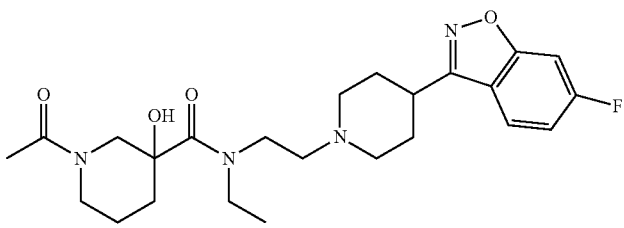 [SMILES: CCN(CCN1CCC(c2noc3cc(F)ccc23)CC1)C(=O)C1(O)CCCN(C(C)=O)C1] | LC-MS: R.T. = 1.258 min<br>ObsMS = 461 [M + 1] |
| 73 | 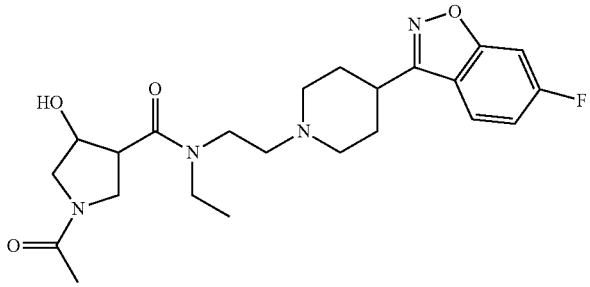 [SMILES: CCN(CCN1CCC(c2noc3cc(F)ccc23)CC1)C(=O)C1CN(C(C)=O)CC1O] | LC-MS: R.T. = 1.350 min<br>ObsMS = 447 [M + 1] |

| Example | Chemical structure | Instrumental analysis data |
|---|---|---|
| 74 | 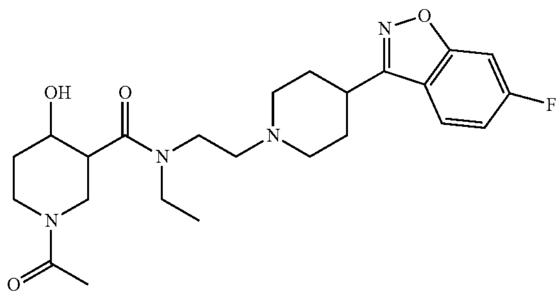 [SMILES: CCN(CCN1CCC(c2noc3cc(F)ccc23)CC1)C(=O)C1CN(C(C)=O)CCC1O] | LC-MS: R.T. = 1.270 min<br>ObsMS = 461 [M + 1] |

Example 75

N-Ethyl-N-{2-[4-(6-fluoro-1,2-benzoisoxazol-3-yl)piperidin-1-yl]ethyl}-4-hydroxy-1-methylpyrrolidine-3-carboxamide

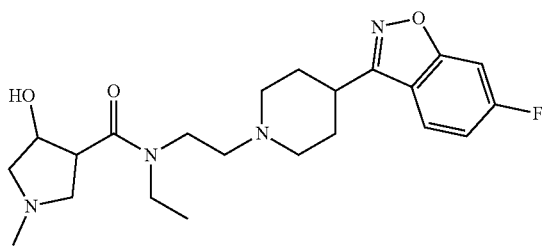 [SMILES: CCN(CCN1CCC(c2noc3cc(F)ccc23)CC1)C(=O)C1CN(C)CC1O]

To a solution of the compound of Example 66 (10.0 mg) in methanol (0.5 mL) were 37% aqueous formaldehyde (0.002 mL), sodium cyanoborohydride (1.09 mg), and acetic acid (0.003 mL). The mixture was stirred at room temperature for 16 hours. Then, water (10 mL) was added thereto, and the mixture was extracted with chloroform (10 mL×2) and concentrated. The concentrated residue was purified by high performance liquid chromatography (column; semi-preparative C-18 column, separation condition; acetonitrile/trifluoroacetic acid:water/trifluoroacetic acid), and desalted with MP-Carbonate resin to obtain the titled compound (6.88 mg).

LC-MS: R.T.=1.083 min ObsMS=419 [M+1]

Example 76

N-Ethyl-N-{2-[4-(6-fluoro-1,2-benzoisoxazol-3-yl)piperidin-1-yl]ethyl}-4-hydroxy-1-methylpiperidine-3-carboxamide

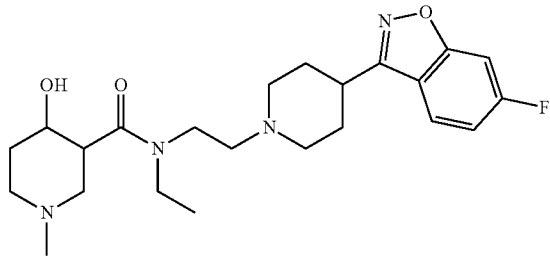 [SMILES: CCN(CCN1CCC(c2noc3cc(F)ccc23)CC1)C(=O)C1CN(C)CCC1O]

According to a similar method to Example 75, the titled compound was prepared from the compound of Example 67.

LC-MS: R.T.=1.092 min ObsMS=433 [M+1]

Example 77

N-Ethyl-N-{2-[4-(6-fluoro-1,2-benzoisoxazol-3-yl)piperidin-1-yl]ethyl}-3-hydroxypropanamide Orotate To a solution of the compound of Example 17 (30 mg) in methanol (0.4 mL) were added orotic acid (14.4 mg). The mixture was stirred at 60° C. for 1 hour, and then ethyl acetate (2.0 mL) was added thereto. The mixture was stirred at room temperature for 1 hour, and the precipitated solid was collected by filtration to obtain the titled compound (27.3 mg).

$^1$H-NMR (400 MHz, DMSO-D$_6$) δ: 11.02 (1H, s), 9.94 (1H, brs), 8.03 (1H, dd, J=8.8, 5.2 Hz), 7.74-7.68 (1H, m), 7.35-7.27 (1H, m), 5.79 (1H, d, J=1.8 Hz), 4.53 (1H, brs), 3.65 (2H, t, J=6.7 Hz), 3.62-3.49 (3H, m), 3.48-3.19 (6H, m), 3.18-2.62 (4H, m), 2.28-2.13 (2H, m), 2.13-1.91 (2H, m), 1.12 (2H, t, J=7.0 Hz), 1.02 (1H, t, J=7.0 Hz).

Powder XRD (°, 2θ±0.2)

4.87, 7.24, 15.27, 15.75, 16.02, 16.39, 16.73, 17.62, 19.51, 20.04, 21.24, 22.05, 22.34, 24.23, 24.80 (Among them, the characteristic 10 peaks were 4.87, 7.24, 15.27, 15.75, 16.02, 17.62, 19.51, 20.04, 21.24, 22.05, and the more characteristic 4 peaks were 4.87, 19.51, 20.04, 21.24.)

DSC

Enthalpy (normalized): 62.81 J/g

Onset x: 157.09° C.

Example 78

N-Ethyl-N-{2-[4-(6-fluoro-1,2-benzoisoxazol-3-yl)piperidin-1-yl]ethyl}-3-hydroxypropanamide Hydrobromide in Form A To a solution of the compound of Example 17 (6.03 g) in acetonitrile (77 mL) were added dropwise 10 to 20% HBr-EtOH (14.1 g). The mixture was stirred at room temperature for 1 hour, and precipitation of a solid was confirmed. The mixture was stirred at 80° C. After confirming that the precipitated solid was completely dissolved, the mixture was stirred for 1 hour. Then, the mixture was gradually cooled, and stirred at room temperature for 12 hours. The precipitated solid was collected by filtration, washed with acetonitrile (10 mL), and dried to obtain a white solid (7.0 g). The resulted white solid (7.0 g) was mixed with tetrahydrofuran (15 mL), and the mixture was stirred at 80° C. for 3.5 hours. Then, the mixture was gradually cooled, and stirred at room temperature for 12 hours. The solid was collected by filtration, washed with tetrahydrofuran (10 mL), and dried to obtain the titled compound (6.20 g).

$^1$H-NMR (400 MHz, DMSO-D$_6$) δ: 9.48 (0.2H, brs), 9.19 (0.8H, brs), 8.11-7.99 (1H, m), 7.78-7.70 (1H, m), 7.40-7.30 (1H, m), 4.53 (1H, brs), 3.78-3.56 (6H, m), 3.55-3.09 (8H, m), 2.40-2.18 (3H, m), 2.15-1.97 (2H, m), 1.19-0.97 (3H, m).

Powder XRD(°, 2θ±0.2)

4.48, 8.98, 12.40, 13.63, 15.23, 16.35, 17.07, 17.88, 18.06, 21.19, 23.13, 23.83, 24.48, 25.22, 25.98 (Among them, the characteristic 10 peaks were 4.48, 12.40, 15.23, 17.07, 17.88, 21.19, 23.13, 24.48, 25.22, 25.98, and the more characteristic 4 peaks were 12.40, 15.23, 17.07, 21.19.)

DSC

Enthalpy (normalized): 82.83 J/g

Onset x: 163.64° C.

Example 79

N-Ethyl-N-{2-[4-(6-fluoro-1,2-benzoisoxazol-3-yl)piperidin-1-yl]ethyl}-3-hydroxypropanamide Hydrobromide in Form B To a solution of the compound of Example 17 (100 mg) in acetonitrile (2.0 mL) was added dropwise 10-20% HBr-EtOH (0.2 mL). The mixture was stirred at room temperature for 1 hour, and the precipitated solid was collected by filtration to obtain the titled compound (67.0 mg).

Powder XRD(°, 2θ±0.2)

7.25, 7.65, 9.90, 11.17, 12.48, 15.34, 15.71, 22.36, 23.36, 23.74, 24.62, 25.05, 25.18, 25.26, 29.36 (Among them, the characteristic 10 peaks were 7.25, 7.65, 9.90, 15.34, 15.71, 23.36, 24.62, 25.05, 25.18, 25.26, and the more characteristic 4 peaks were 7.25, 7.65, 9.90, 15.34.)

DSC

Enthalpy (normalized): 86.51 J/g

Onset x: 164.04° C.

Example 80

N-Ethyl-N-{2-[4-(6-fluoro-1,2-benzoisoxazol-3-yl)piperidin-1-yl]ethyl}-3-hydroxypropanamide Tosilate To a solution of the compound of Example 17 (66.7 g) in acetone (200 mL) was added a solution of p-toluenesulfonic acid monohydrate (41.9 g) in acetone (150 mL). The mixture was stirred at room temperature for 2 hours. The precipitated solid was collected by filtration, washed with acetone (60 mL), and dried to obtain a white solid (78.8 g). The resulted white solid (78.8 g) and a mixture of acetone (608 mL) and water (33.4 mL) were stirred at 70° C. After confirming that the white solid was completely dissolved, the mixture was cooled gradually, and stirred at room temperature for 12 hours. After stirring at 0° C. for 1 hour, the resulted solid was collected by filtration, washed with a mixture solvent of 5% water-acetone (70 mL) which was cooled to 0° C., and dried to obtain the titled compound (69.4 g).

$^1$H-NMR (400 MHz, DMSO-D$_6$) δ: 9.39-9.00 (1H, m), 8.08-7.99 (1H, m), 7.77-7.71 (1H, m), 7.46 (2H, d, J=7.9 Hz), 7.39-7.30 (1H, m), 7.10 (2H, d, J=7.9 Hz), 4.53 (1H, brs), 3.76-3.56 (6H, m), 3.54-3.11 (8H, m), 2.38-2.17 (6H, m), 2.12-1.96 (2H, m), 1.16-0.98 (3H, m).

Powder XRD(°, 2θ±0.2)

6.87, 7.03, 9.64, 13.74, 15.19, 15.37, 15.68, 16.22, 19.82, 21.60, 21.67, 22.10, 23.15, 23.88, 27.67 (Among them, the characteristic 10 peaks were 7.03, 9.64, 15.19, 15.37, 15.68, 16.22, 21.60, 21.67, 23.15, 23.88, and the more characteristic 4 peaks were 7.03, 9.64, 15.19, 15.68.)

DSC

Enthalpy (normalized): 99.47 J/g

Onset x: 162.26° C.

Reference Example 1

N-Ethyl-2-[4-(6-fluoro-1,2-benzoisoxazol-3-yl)piperidin-1-yl]ethane-1-amine Dihydrochloride

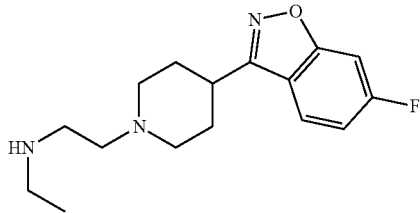

To a solution of 6-fluoro-3-(4-piperidinyl)-1,2-benzoisoxazole (5.78 g) in chloroform (131 mL) were added tert-butyl ethyl(2-oxoethyl)carbamate (4.91 g) and sodium triacetoxyborohydride (11.1 g). The mixture was stirred at room temperature for 5 hours. Saturated aqueous sodium bicarbonate (100 mL) were added thereto, and the mixture was extracted with chloroform (100 mL×2), dried over anhydrous sodium sulfate, filtered, and concentrated. The residue was purified by silica gel column chromatography (chloroform/methanol). To a solution of the resulted compound in chloroform (131 mL) was added 4 mol/L hydrochloric acid-ethyl acetate (60 mL). The mixture was stirred at room temperature for 2 hours. The precipitated solid was collected by filtration, washed with ethyl acetate (20 mL×2), and dried to obtain the titled compound (6.24 g).

$^1$H-NMR (400 MHz, DMSO-D$_6$) δ: 9.31 (2H, brs), 8.18 (1H, dd, J=8.5, 5.5 Hz), 7.74 (1H, dd, J=8.9, 2.1 Hz), 7.35 (1H, ddd, J=9.0, 9.0, 2.2 Hz), 3.81-3.72 (2H, m), 3.55-3.46 (5H, m), 3.28-3.15 (2H, m), 3.08-2.97 (2H, m), 2.43-2.23 (4H, m), 1.25 (3H, t, J=7.3 Hz).

Reference Examples 2 to 13

According to a similar method of Reference example 1, the compounds of Reference examples 2 to 13 were prepared from the corresponding Reference example compounds or reagents.

| Reference example | Chemical structure | Instrumental analysis data |
|---|---|---|
| 2 | (indazole-piperidine-ethylamine with 5-F, 2HCl) | ¹H-NMR (400 MHz, CD₃OD) δ: 8.07-7.98 (1H, m), 7.76-7.60 (1H, m), 7.48-7.39 (1H, m), 7.25 (1H, ddd, J = 9.1, 9.1, 1.8 Hz), 5.06-4.94 (1H, m), 3.94-3.84 (2H, m), 3.64-3.55 (4H, m), 3.49-3.37 (2H, m), 3.19 (2H, q, J = 7.3 Hz), 2.77-2.64 (2H, m), 2.36-(2H, m), 1.39 (3H, t, J = 7.3 Hz). |
| 3 | (benzisoxazole-piperidine-ethylamine with 6-F, 5-methyl, 2HCl) | ¹H-NMR (400 MHz, CDCl₃) δ: 7.55-7.47 (1H, m), 7.24 (1H, s), 7.18 (1H, d, J = 9.2 Hz), 3.47-2.94 (8H, m), 2.66-2.45 (2H, m), 2.34 (3H, d, J = 1.8 Hz), 2.30-2.16 (1H, m), 2.15-1.94 (4H, m), 1.10 (3H, t, J = 7.0 Hz). |
| 4 | (benzisoxazole-piperidine-ethylamine with 5-methyl, 2HCl) | ¹H-NMR (400 MHz, CD₃OD) δ: 7.81 (1H, s), 7.53-7.43 (2H, m), 3.92-3.83 (2H, m), 3.72-3.42 (5H, m), 3.40-3.32 (2H, m), 3.20 (2H, q, J = 7.1 Hz), 2.56-2.36 (7H, m), 1.39 (3H, t, J = 7.3 Hz). |
| 5 | (benzisoxazole-piperidine-ethylamine with 6-Cl, 2HCl) | ¹H-NMR (400 MHz, CD₃OD) δ: 8.00 (1H, d, J = 8.5 Hz), 7.74 (1H, s), 7.41 (1H, dd, J = 8.5, 1.8 Hz), 3.92-3.81 (2H, m), 3.71-3.44 (5H, m), 3.40-3.32 (2H, m), 3.20 (2H, q, J = 6.9 Hz), 2.64-2.36 (4H, m), 1.39 (3H, t, J = 7.3 Hz). |
| 6 | (indazole-piperidine-ethylamine with 6-F, NH, 2HCl) | ¹H-NMR (400 MHz, CD₃OD) δ: 8.06 (1H, dd, J = 8.8, 5.2 Hz), 7.26 (1H, d, J = 9.1 Hz), 7.06 (1H, dd, J = 9.1, 9.1 Hz), 3.92-3.80 (2H, m), 3.67-3.50 (5H, m), 3.42-3.33 (2H, m), 3.20 (2H, q, J = 7.1 Hz), 2.57-2.43 (2H, m), 2.41-2.27 (2H, m), 1.40 (3H, t, J = 7.3 Hz). |
| 7 | (indole-piperidine-ethylamine with 6-F, NH, 2HCl) | ¹H-NMR (400 MHz, DMSO-D₆) δ: 10.98 (1H, s), 10.72 (1H, s), 9.20 (2H, s), 7.67 (1H, dd, J = 8.5, 5.5 Hz), 7.15-7.09 (2H, m), 6.88-6.80 (1H, m), 3.74-3.65 (2H, m), 3.49-3.39 (4H, m), 3.21-3.09 (2H, m), 3.08-2.93 (3H, m), 2.18-2.07 (4H, m), 1.23 (3H, t, J = 7.0 Hz). |

-continued

| Reference example | Chemical structure | Instrumental analysis data |
|---|---|---|
| 8 | 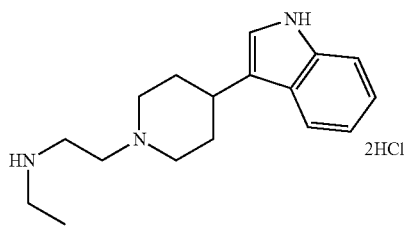 [SMILES: CCNCCN1CCC(c2c[nH]c3ccccc23)CC1] | $^1$H-NMR (400 MHz, DMSO-D$_6$) δ: 10.89 (1H, s), 10.70 (1H, s), 9.20 (2H, s), 7.67 (1H, d, J = 7.9 Hz), 7.35 (1H, d, J = 8.5 Hz), 7.12 (1H, d, J = 2.4 Hz), 7.09-7.04 (1H, m), 6.99-6.94 (1H, m), 3.75-3.65 (2H, m), 3.52-3.40 (4H, m), 3.22-3.11 (2H, m), 3.07-2.94 (3H, m), 2.22-2.07 (4H, m), 1.23 (3H, t, J = 7.3 Hz). |
| 9 | 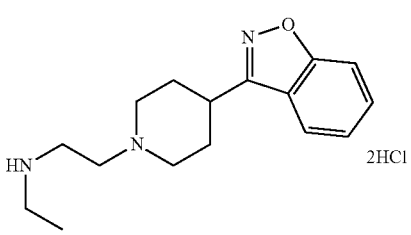 [SMILES: CCNCCN1CCC(c2noc3ccccc23)CC1] | $^1$H-NMR (400 MHz, CD$_3$OD) δ: 8.03-7.92 (1H, m), 7.67-7.61 (2H, m), 7.43-7.37 (1H, m), 3.92-3.73 (2H, m), 3.64-3.42 (5H, m), 3.38-3.31 (2H, m), 3.19 (2H, q, J = 7.3 Hz), 2.55-2.33 (4H, m), 1.38 (3H, t, J = 7.3 Hz). |
| 10 | 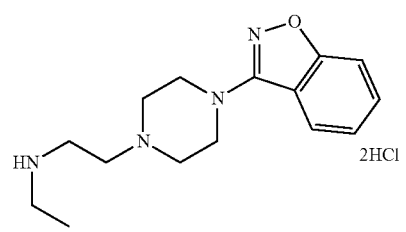 [SMILES: CCNCCN1CCN(c2noc3ccccc23)CC1] | $^1$H-NMR (400 MHz, CD$_3$OD) δ: 7.90 (1H, d, J = 7.9 Hz), 7.63-7.58 (1H, m), 7.53 (1H, d, J = 8.5 Hz), 7.34 (1H, dd, J = 7.6, 7.6 Hz), 4.16-3.72 (4H, m), 3.69-3.40 (8H, m), 3.19 (2H, q, J = 7.1 Hz), 1.38 (3H, t, J = 7.3 Hz). |
| 11 | 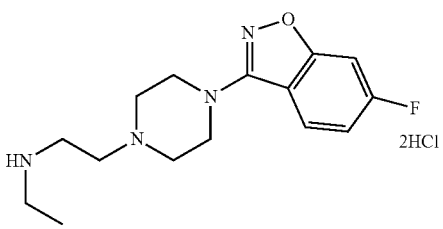 [SMILES: CCNCCN1CCN(c2noc3cc(F)ccc23)CC1] | $^1$H-NMR (400 MHz, CD$_3$OD) δ: 7.93 (1H, dd, J = 9.2, 4.9 Hz), 7.33 (1H, dd, J = 8.9, 2.1 Hz), 7.14 (1H, ddd, J = 9.0, 9.0, 2.0 Hz), 4.33-3.71 (4H, m), 3.70-3.41 (8H, m), 3.19 (2H, q, J = 7.3 Hz), 1.38 (3H, t, J = 7.3 Hz). |
| 12 | 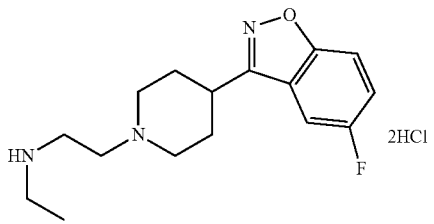 [SMILES: CCNCCN1CCC(c2noc3ccc(F)cc23)CC1] | $^1$H-NMR (400 MHz, DMSO-D$_6$) δ: 11.01 (1H, s), 9.20 (2H, s), 8.04-7.98 (1H, m), 7.81 (1H, dd, J = 9.1, 4.3 Hz), 7.57 (1H, ddd, J = 9.1, 9.1, 2.4 Hz), 3.82-3.70 (2H, m), 3.55-3.40 (4H, m), 3.26-3.12 (3H, m), 3.09-2.96 (2H, m), 2.42-2.22 (4H, m), 1.23 (3H, t, J = 7.3 Hz). |
| 13 | 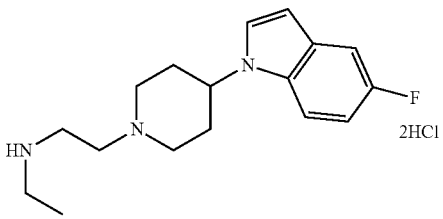 [SMILES: CCNCCN1CCC(n2ccc3cc(F)ccc32)CC1] | LC-MS: R.T. = 0.443 min ObsMS = 290 [M + 1] |

Reference Example 14

6-Fluoro-5-methyl-3-(piperidin-4-yl)-1,2-benzo-isoxazole Monohydrochloride

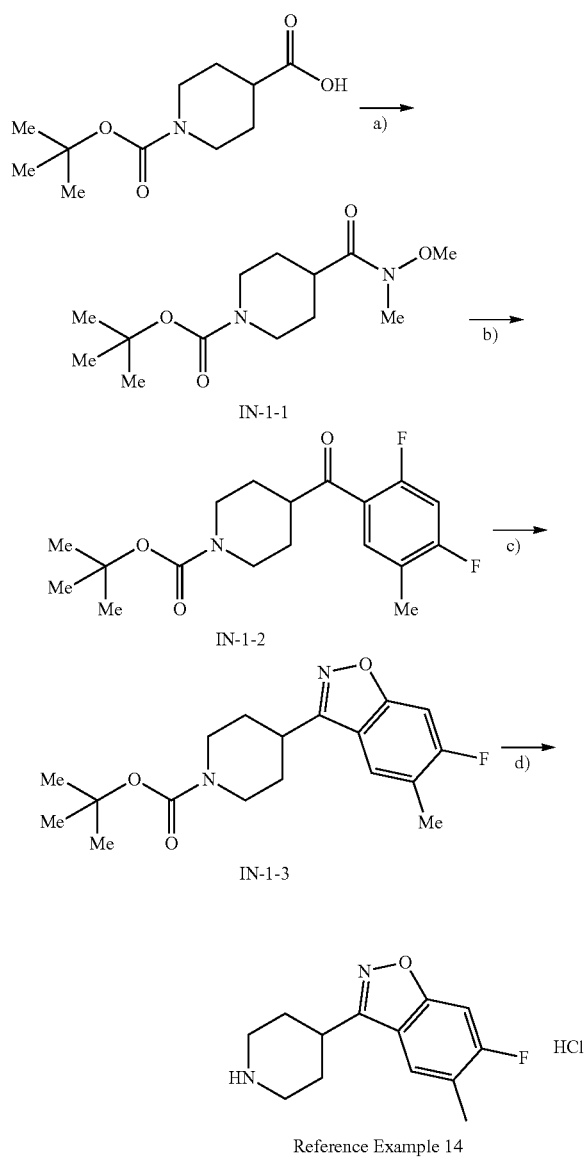

Reference Example 14 a) Preparation of tert-butyl 4-[methoxy(methyl)carbamoyl]piperidine-1-carboxylate (Compound IN-1-1)

The mixture of 1-(tert-butoxycarbonyl)piperidine-4-carboxylic acid (5.00 g), N,O-dimethylhydroxylamine hydrochloride (3.19 g), N1-((ethylimino)methylene)-N3,N3-dimethylpropane-1,3-diamine hydrochloride (5.02 g), triethylamine (4.41 g), and N,N-dimethylformamide (100 mL) was stirred at room temperature for 1.5 hours. Then, saturated aqueous ammonium chloride was added thereto, and the mixture was extracted with ethyl acetate. The combined organic layer was washed twice with saturated aqueous ammonium chloride, and with saturated aqueous sodium bicarbonate and brine, and dried over anhydrous sodium sulfate. The mixture was filtered and concentrated to obtain the titled compound (4.52 g) $^1$H-NMR (400 MHz, CDCl$_3$) δ: 4.03-4.24 (2H, m), 3.72 (3H, s), 3.19 (3H, s), 2.70-2.86 (3H, m), 1.63-1.76 (4H, m), 1.46 (9H, s).

b) Preparation of tert-butyl 4-(2,4-difluoro-5-methylbenzoyl)piperidine-1-carboxylate (Compound IN-1-2)

To a solution of 1-bromo-2,4-difluoro-5-methylbenzene (2.28 g) in tetrahydrofuran (36 mL) was added dropwise 1.63 mol/L n-butyllithium/hexane (7.43 mL) over 3 minutes at −78° C. After stirring at −78° C. for 1 hour, Compound IN-1-1 (1.50 g) was added thereto, and the mixture was stirred for 2.5 hours at −78° C. Then, saturated aqueous ammonium chloride was added thereto, and the mixture was extracted with ethyl acetate, dried over anhydrous sodium sulfate, filtered, and concentrated. The concentrated residue was purified by silica gel column chromatography (hexane/ethyl acetate) to obtain the titled compound (2.01 g).

$^1$H-NMR (400 MHz, CDCl$_3$) δ: 7.17-7.25 (1H, m), 6.80-6.87 (1H, m), 1.83-1.92 (2H, m), 1.59-1.69 (2H, m), 1.45 (9H, s).

c) Preparation of tert-butyl 4-(6-fluoro-5-methyl-1,2-benzoxazol-3-yl)piperidine-1-carboxylate (Compound IN-1-3)

A mixture of Compound IN-1-2 (731 mg), hydroxylamine hydrochloride (599 mg), and sodium acetate (707 mg) in ethanol (10 mL) waas stirred at 60° C. for 4 hours. Then, water was added thereto, and the mixture was extracted with ethyl acetate, washed with brine, dried over anhydrous sodium sulfate, filtered, and concentrated. The concentrated residue was purified by silica gel column chromatography (hexane/ethyl acetate). The resulted product (335 mg) was mixed with cesium carbonate (615 mg) and acetonitrile (9.0 mL), and the mixture was stirred in a sealed tube at 130° C. for 3.5 hours. Then, the reaction mixture was filtered, concentrated, and purified by silica gel column chromatography (hexane/ethyl acetate) to obtain the titled compound (90.8 mg).

$^1$H-NMR (400 MHz, CDCl$_3$) δ: 7.47 (1H, d, J=7.1 Hz), 7.21 (1H, d, J=9.0 Hz), 4.11-4.36 (2H, m), 3.16-3.26 (1H, m), 2.89-3.03 (2H, m), 2.38 (3H, d, J=1.7 Hz), 2.01-2.10 (2H, m), 1.87-1.99 (2H, m).

d) Preparation of 6-fluoro-5-methyl-3-(piperidin-4-yl)-1,2-benzoisoxazole Monohydrochloride (Reference Example 14)

To a solution of Compound IN-1-3 (131 mg) in dichloromethane (1.0 mL) was added 4 mol/L hydrochloric acid/ethyl acetate (1.0 mL), and the mixture was stirred at room temperature for 1.5 hours. Then, the reaction mixture was concentrated to obtain the titled compound (114 mg).

$^1$H-NMR (400 MHz, CDCl$_3$) δ: 7.30 (1H, d, J=7.3 Hz), 7.11 (1H, s), 7.06 (1H, d, J=9.1 Hz), 4.12-4.04 (2H, m), 3.09-3.01 (1H, m), 2.84-2.75 (2H, m), 2.22 (3H, d, J=1.8 Hz), 1.93-1.86 (2H, m), 1.84-1.71 (2H, m).

Reference Example 15

5-Methyl-3-(piperidin-4-yl)-1,2-benzoisoxazole Monohydrochloride

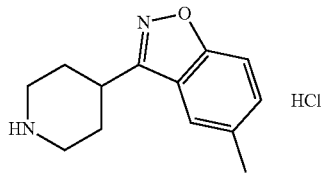 [SMILES: Cc1ccc2onc(C3CCNCC3)c2c1 ; Cl]

According to a similar method to Reference example 14, the titled compound was prepared from 1-fluoro-2-iodo-4-methylbenzene.

$^1$H-NMR (400 MHz, CDCl$_3$) δ: 7.48-7.43 (2H, m), 7.38-7.34 (1H, m), 4.29-4.20 (2H, m), 3.28-3.18 (1H, m), 3.02-2.92 (2H, m), 2.48 (3H, s), 2.11-2.03 (2H, m), 2.03-1.90 (2H, m).

Reference Example 16

N-(Cyclopropylmethyl)-2-[4-(6-fluoro-1,2-benzo-isoxazol-3-yl)piperidin-1-yl]ethane-1-amine

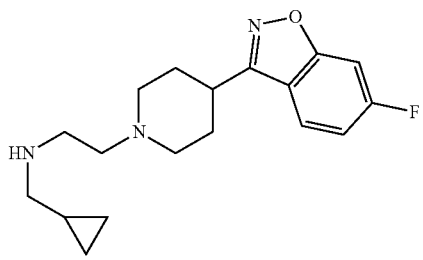 [SMILES: Fc1ccc2c(C3CCN(CCNCC4CC4)CC3)noc2c1]

To a solution of 2-(4-(6-fluorobenzo[d]isoxazol-3-yl)piperidin-1-yl)ethane-1-amine (50.0 mg) in chloroform (2.0 mL) was added cyclopropanecarbaldehyde (16.0 mg), and the mixture was stirred at room temperature for 30 minutes. Then, sodium triacetoxyborohydride (60.4 mg) was added thereto, and the mixture was stirred at room temperature for 1 hour. Saturated aqueous sodium bicarbonate (30 mL) was added thereto. The mixture was extracted with chloroform (30 mL×2), dried over anhydrous sodium sulfate, filtered, and concentrated to obtain the titled compound (26.0 mg).

LC-MS: R.T.=1.250 min ObsMS=318 [M+1]

Reference Example 17

N-{2-[4-(6-Fluoro-1,2-benzoisoxazol-3-yl)piperidin-1-yl]ethyl}propane-2-amine

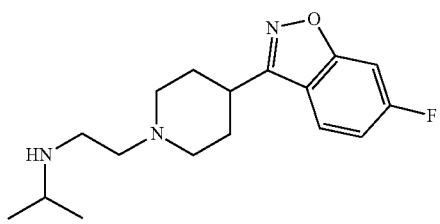 [SMILES: CC(C)NCCN1CCC(c2noc3cc(F)ccc23)CC1]

According to a similar method to Reference example 16, the titled compound was prepared from acetone.

LC-MS: R.T.=1.176 min ObsMS=306 [M+1]

Reference Example 18

({2-[4-(6-Fluoro-1,2-benzoisoxazol-3-yl)piperidin-1-yl]ethyl}amino)acetonitrile

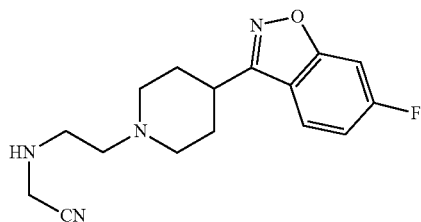 [SMILES: N#CCNCCN1CCC(c2noc3cc(F)ccc23)CC1]

To a suspension of 55% sodium hydride (7.92 mg) in N,N-dimethylformamide (2.0 mL) was added the compound of Reference example 20 (60.0 mg), and the mixture was stirred at room temperature for 30 minutes. 2-Iodoacetonitrile (41.3 mg) was added thereto. The reaction mixture was stirred at room temperature for 1 hour, and water (30 mL) was added thereto. The mixture was extracted with chloroform (30 mL×2), dried over anhydrous sodium sulfate, filtered, and concentrated. To the concentrated residue was added 4 mol/L hydrochloric acid/ethyl acetate (3.0 mL), the mixture was stirred at room temperature for 1 hour, and concentrated. The concentrated residue was purified by amino silica gel column chromatography (hexane/ethyl acetate) to obtain the titled compound (25.0 mg).

LC-MS: R.T.=0.530 min ObsMS=303 [M+1]

Reference Example 19

N-Ethyl-3-[4-(6-fluoro-1,2-benzoisoxazol-3-yl)piperidin-1-yl]propane-1-amine Dihydrochloride

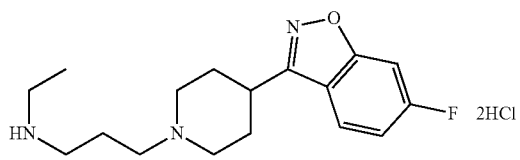 [SMILES: CCNCCCN1CCC(c2noc3cc(F)ccc23)CC1]

According to a similar method to Reference example 18, the titled compound was prepared from the compound of Reference example 21.

Reference Example 20

Tert-butyl {2-[4-(6-fluoro-1,2-benzoisoxazol-3-yl)piperidin-1-yl]ethyl}carbamate

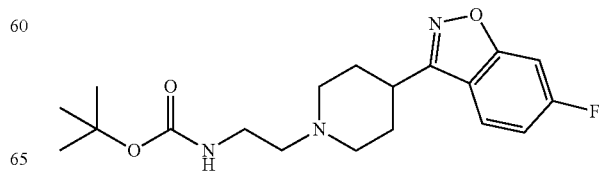

To a solution (60 mL) of 6-fluoro-3-(piperidin-4-yl)benzo[d]isoxazole (2.89 g) in chloroform was added tert-butyl (2-oxoethyl)carbamate (2.30 g), and the mixture was stirred at room temperature for 30 minutes. Sodium triacetoxyborohydride (3.34 g) was added thereto, and the mixture was stirred at room temperature for 3 hours. Saturated aqueous sodium bicarbonate (100 mL) was added thereto, and the mixture was extracted with chloroform (100 mL×2), dried over anhydrous sodium sulfate, filtered, and concentrated. The concentrated residue was purified by silica gel column chromatography (chloroform/methanol) to obtain the titled compound (3.98 g).

$^1$H-NMR (400 MHz, CDCl$_3$) δ: 7.67 (1H, dd, J=8.8, 5.2 Hz), 7.24-7.20 (1H, m), 7.04 (1H, ddd, J=8.8, 8.8, 2.0 Hz), 5.02 (1H, s), 3.29-3.20 (2H, m), 3.10-2.98 (3H, m), 2.53-2.46 (2H, m), 2.22-2.13 (2H, m), 2.09-2.00 (4H, m), 1.45 (9H, s).

Reference Example 21

Tert-butyl {3-[4-(6-fluoro-1,2-benzoisoxazol-3-yl)piperidin-1-yl]propyl}carbamate

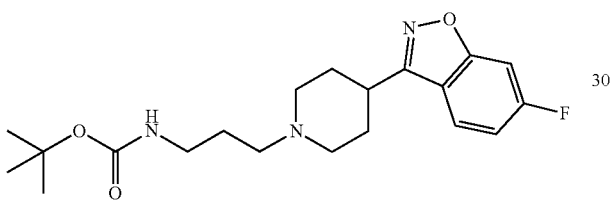

To a solution of 6-fluoro-3-(piperidin-4-yl)benzo[d]isoxazole (2.00 g) in acetonitrile (50 mL) were added water (12.5 mL), tert-butyl(3-bromopropyl)carbamate (2.59 g), and potassium carbonate (3.76 g). The mixture was stirred at 60° C. for 3.5 hours, and water (200 mL) was added thereto. The mixture was extracted with ethyl acetate (200 mL×2), dried over anhydrous sodium sulfate, filtered, and concentrated. The concentrated residue was purified by silica gel column chromatography (chloroform/methanol) to obtain the titled compound (3.46 g).

$^1$H-NMR (400 MHz, CDCl$_3$) δ: 7.67 (1H, dd, J=8.8, 5.2 Hz), 7.22 (1H, dd, J=8.5, 2.4 Hz), 7.02 (1H, ddd, J=8.8, 8.8, 2.2 Hz), 5.50 (1H, s), 3.23-3.17 (2H, m), 3.12-3.00 (3H, m), 2.46 (2H, t, J=6.7 Hz), 2.16-1.99 (6H, m), 1.72-1.64 (2H, m), 1.43 (9H, s).

Reference Example 22

N-{2-[4-(6-Fluoro-1,2-benzoisoxazol-3-yl)piperidin-1-yl]ethyl}propane-1-amine

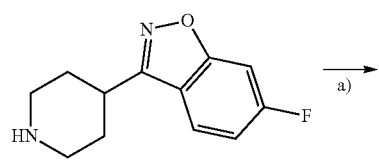

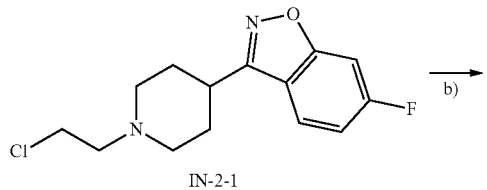
IN-2-1

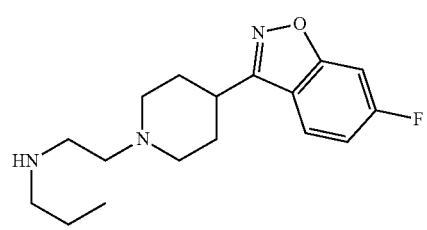
Referemce Example 22 a) Preparation of 3-[1-(2-chloroethyl)piperidin-4-yl]-6-fluoro-1,2-benzoisoxazole (Compound IN-2-1)

To a solution (25 mL) of 6-fluoro-3-(piperidin-4-yl)benzo[d]isoxazole (3.00 g) in tetrahydrofuran were added water (6.3 mL), potassium hydroxide (1.68 g), and 1-bromo-2-chloroethane (5.65 mL), and the mixture was stirred at room temperature for 24 hours. Water (15 mL) was added thereto. The mixture was extracted with chloroform (10 mL×3), dried over anhydrous sodium sulfate, filtered, and concentrated. The concentrated residue was purified by silica gel column chromatography (ethyl acetate/methanol) to obtain the titled compound (1.94 g).

$^1$H-NMR (400 MHz, CDCl$_3$) δ: 7.70 (1H, dd, J=8.5, 5.3 Hz), 7.25 (1H, dd, J=8.9, 2.5 Hz), 7.06 (1H, ddd, J=8.8, 8.8, 2.1 Hz), 3.64 (2H, t, J=6.9 Hz), 3.01-3.15 (3H, m), 2.81 (2H, t, J=6.9 Hz), 2.24-2.39 (2H, m), 2.02-2.18 (4H, m).

b) Preparation of N-{2-[4-(6-fluoro-1,2-benzoisoxazol-3-yl)piperidin-1-yl]ethyl}propane-1-amine (Reference Example 22)

To a solution of Compound IN-2-1 (80.0 mg) in acetonitrile (1.4 mL) were added n-propylamine (0.0349 mL), potassium carbonate (117 mg), potassium iodide (9.39 mg), and the mixture was stirred at 90° C. for 4 hours. The reaction mixture was filtered and concentrated. The concentrated residue was purified by amino silica gel column chromatography (chloroform/methanol) to obtain the titled compound (50.9 mg).

$^1$H-NMR (400 MHz, CDCl$_3$) δ: 7.66 (1H, dd, J=8.8, 5.2 Hz), 7.22 (1H, dd, J=8.5, 2.4 Hz), 7.03 (1H, ddd, J=8.8, 8.8, 2.2 Hz), 3.10-2.99 (3H, m), 2.72 (2H, t, J=6.1 Hz), 2.58 (2H, t, J=7.0 Hz), 2.53 (2H, t, J=6.4 Hz), 2.21-1.99 (6H, m), 1.56-1.46 (2H, m), 0.91 (3H, t, J=7.3 Hz).

Reference Example 23

N-Ethyl-N-{2-[4-(6-fluoro-1,2-benzoisoxazol-3-yl)piperidin-1-yl]ethyl}ethenesulfonamide

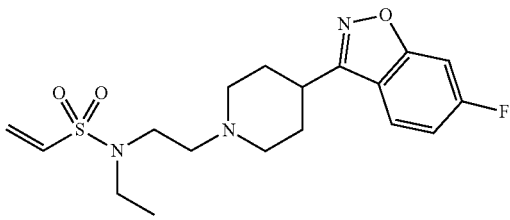 [SMILES: C=CS(=O)(=O)N(CC)CCN1CCC(c2noc3cc(F)ccc23)CC1]

To a solution of the compound of Reference example 1 (1.00 g) in dichloromethane (40 mL) were added triethylamine (2.39 mL) and 2-chloroethanesulfonyl chloride (0.433 mL), and the mixture was stirred at room temperature for 4 hours. The reaction mixture was concentrated, and the concentrated residue was purified by silica gel column chromatography (chloroform/methanol) to obtain the titled compound (0.670 g).

$^1$H-NMR (400 MHz, CDCl$_3$) δ: 7.65 (1H, dd, J=8.5, 4.9 Hz), 7.22 (1H, dd, J=8.5, 2.4 Hz), 7.04 (1H, ddd, J=8.9, 8.9, 2.2 Hz), 6.54 (1H, dd, J=16.5, 9.8 Hz), 6.20 (1H, d, J=16.5 Hz), 5.89 (1H, d, J=9.8 Hz), 3.31 (2H, t, J=7.0 Hz), 3.25 (2H, q, J=7.1 Hz), 3.11-3.00 (3H, m), 2.61 (2H, t, J=6.7 Hz), 2.32-2.17 (2H, m), 2.10-1.97 (4H, m), 1.20 (3H, t, J=7.3 Hz).

Reference Examples 24 to 36

According to the method of Reference example 23, the compounds of Reference examples 24 to 36 were prepared from the corresponding Reference example compounds.

| Reference example | Chemical structure | Instrumental analysis data |
|---|---|---|
| 24 | 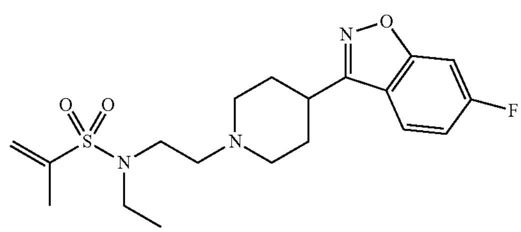 [SMILES: C=C(C)S(=O)(=O)N(CC)CCN1CCC(c2noc3cc(F)ccc23)CC1] | LC-MS: R.T. = 1.566 min<br>ObsMS = 396 [M + 1] |
| 25 | 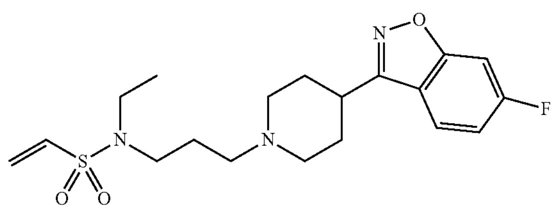 [SMILES: C=CS(=O)(=O)N(CC)CCCN1CCC(c2noc3cc(F)ccc23)CC1] | $^1$H-NMR (400 MHz, CDCl$_3$) δ: 7.67 (1H, dd, J = 8.5, 5.5 Hz), 7.22 (1H, dd, J = 8.5, 1.8 Hz), 7.04 (1H, ddd, J = 8.9, 8.9, 2.0 Hz), 6.42 (1H, dd, J = 16.5, 9.8 Hz), 6.19 (1H, d, J = 16.5 Hz), 5.89 (1H, d, J = 9.8 Hz), 3.28-3.14 (4H, m), 3.12-2.96 (3H, m), 2.50-2.38 (2H, m), 2.24-1.99 (6H, m), 1.88-1.78 (2H, m), 1.19 (3H, t, J = 7.3 Hz). |
| 26 | 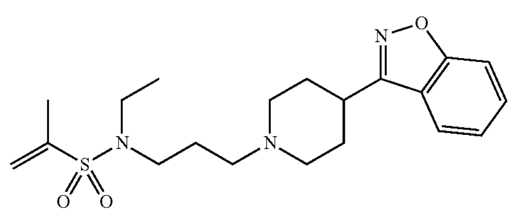 [SMILES: C=C(C)S(=O)(=O)N(CC)CCCN1CCC(c2noc3ccccc23)CC1] | $^1$H-NMR (400 MHz, CDCl$_3$) δ: 7.73 (1H, d, J = 7.9 Hz), 7.57-7.47 (2H, m), 7.30-7.24 (1H, m), 5.95 (1H, s), 5.57-5.54 (1H, m), 3.32-3.22 (4H, m), 3.17-2.99 (3H, m), 2.51-2.36 (2H, m), 2.28-2.05 (6H, m), 2.02 (3H, s), 1.90-1.77 (2H, m), 1.19 (3H, t, J = 7.0 Hz). |
| 27 | 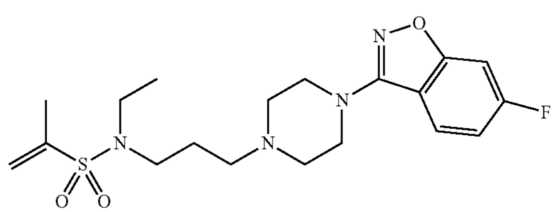 [SMILES: C=C(C)S(=O)(=O)N(CC)CCCN1CCC(c2noc3cc(F)ccc23)CC1] | $^1$H-NMR (400 MHz, CDCl$_3$) δ: 7.60 (1H, dd, J = 8.8, 5.2 Hz), 7.11 (1H, dd, J = 8.5, 2.4 Hz), 6.96 (1H, ddd, J = 8.8, 8.8, 2.0 Hz), 5.96-5.93? (1H, m), 5.57-5.54 (1H, m), 3.59-3.48 (4H, m), 3.31-3.23 (4H, m), 2.68-2.57 (4H, m), 2.50-2.39 (2H, m), 2.02 (3H, s), 1.89-1.77 (2H, m), 1.19 (3H, t, J = 7.3 Hz). |

| Reference example | Chemical structure | Instrumental analysis data |
|---|---|---|
| 28 | 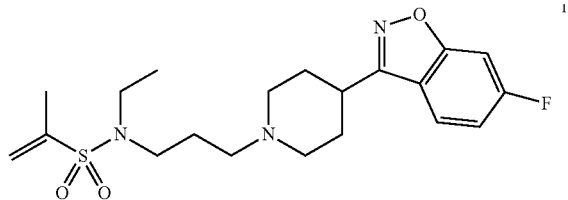 | $^1$H-NMR (400 MHz, CDCl$_3$) δ: 7.62 (1H, dd, J = 8.5, 4.9 Hz), 7.17 (1H, dd, J = 8.2, 1.5 Hz), 6.99 (1H, ddd, J = 8.8, 8.8, 2.0 Hz), 5.92-5.88 (1H, m), 5.53-5.48 (1H, m), 3.27-3.16 (4H, m), 3.09-2.93 (3H, m), 2.43-2.32 (2H, m), 2.16-1.92 (9H, m), 1.86-1.69 (2H, m), 1.14 (3H, t, J = 7.3 Hz). |
| 29 | 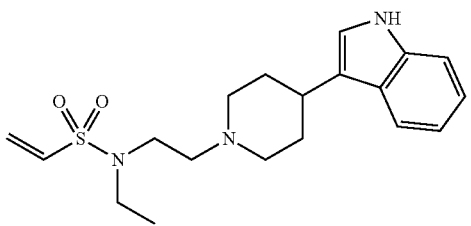 [SMILES: C=CS(=O)(=O)N(CC)CCN1CCC(c2c[nH]c3ccccc23)CC1] | $^1$H-NMR (400 MHz, CDCl$_3$) δ: 7.99 (1H, s), 7.61 (1H, d, J = 7.9 Hz), 7.35 (1H, d, J = 8.5 Hz), 7.17 (1H, ddd, J = 7.6, 7.6, 1.2 Hz), 7.12-7.06 (1H, m), 6.97 (1H, d, J = 2.4 Hz), 6.54 (1H, dd, J = 16.5, 9.8 Hz), 6.21 (1H, d, J = 17.1 Hz), 5.89 (1H, d, J = 10.4 Hz), 3.46-3.34 (2H, m), 3.26 (2H, q, J = 7.1 Hz), 3.20-3.05 (2H, m), 2.93-2.81 (1H, m), 2.76-2.61 (2H, m), 2.43-2.22 (2H, m), 2.14-2.02 (2H, m), 1.99-1.79 (2H, m), 1.22 (3H, t, J = 7.0 Hz). |
| 30 | 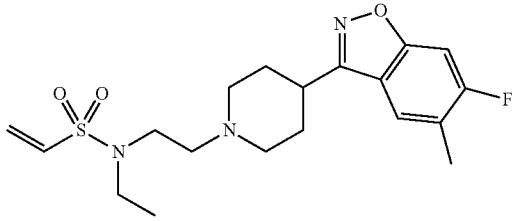 [SMILES: C=CS(=O)(=O)N(CC)CCN1CCC(c2noc3cc(F)c(C)cc23)CC1] | $^1$H-NMR (400 MHz, CDCl$_3$) δ: 7.57-7.46 (1H, m), 7.19 (1H, d, J = 9.1 Hz), 6.52 (1H, dd, J = 15.2, 9.1 Hz), 6.21 (1H, d, J = 16.5 Hz), 5.91 (1H, d, J = 8.5 Hz), 3.47-3.00 (8H, m), 2.79-2.60 (1H, m), 2.42-1.94 (9H, m), 1.22 (3H, t, J = 7.0 Hz). |
| 31 | 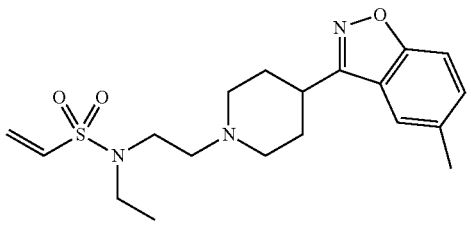 [SMILES: C=CS(=O)(=O)N(CC)CCN1CCC(c2noc3ccc(C)cc23)CC1] | $^1$H-NMR (400 MHz, CDCl$_3$) δ: 7.46 (1H, s), 7.42 (1H, d, J = 8.5 Hz), 7.34-7.29 (1H, m), 6.55 (1H, dd, J = 16.8, 10.1 Hz), 6.20 (1H, d, J = 16.5 Hz), 5.89 (1H, d, J = 9.8 Hz), 3.37-3.29 (2H, m), 3.25? (2H, q, J = 7.1 Hz), 3.12-3.00 (3H, m), 2.68-2.57 (2H, m), 2.44 (3H, s), 2.34-2.19 (2H, m), 2.14-2.01 (4H, m), 1.21 (3H, t, J = 7.3 Hz). |
| 32 | 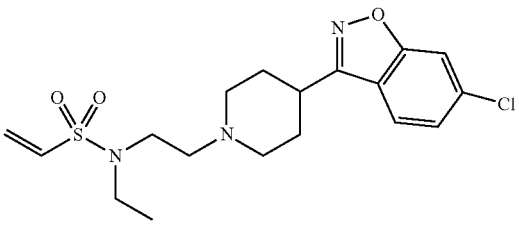 [SMILES: C=CS(=O)(=O)N(CC)CCN1CCC(c2noc3cc(Cl)ccc23)CC1] | $^1$H-NMR (400 MHz, CDCl$_3$) δ: 7.62 (1H, d, J = 8.5 Hz), 7.56 (1H, d, J = 1.8 Hz), 7.26 (1H, dd, J = 8.2, 1.5 Hz), 6.53 (1H, dd, J = 16.8, 10.1 Hz), 6.20 (1H, d, J = 17.1 Hz), 5.89 (1H, d, J = 9.8 Hz), 3.31 (2H, t, J = 7.0 Hz), 3.25 (2H, q, J = 7.1 Hz), 3.12-2.98 (3H, m), 2.66-2.56 (2H, m), 2.33-2.18 (2H, m), 2.12-1.98 (4H, m), 1.20 (3H, t, J = 7.0 Hz). |

-continued

| Reference example | Chemical structure | Instrumental analysis data |
|---|---|---|
| 33 | 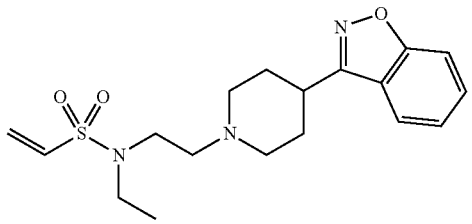 [SMILES: C=CS(=O)(=O)N(CC)CCN1CCC(c2noc3ccccc23)CC1] | $^1$H-NMR (400 MHz, CDCl$_3$) δ: 7.73-7.69 (1H, m), 7.57-7.49 (2H, m), 7.30-7.25 (1H, m), 6.55 (1H, dd, J = 16.5, 9.8 Hz), 6.20 (1H, d, J = 16.5 Hz), 5.89 (1H, d, J = 9.8 Hz), 3.32 (2H, t, J = 7.0 Hz), 3.25 (2H, q, J = 7.1 Hz), 3.16-3.00 (3H, m), 2.61 (2H, t, J = 6.7 Hz), 2.34-2.19 (2H, m), 2.14-2.01 (4H, m), 1.21 (3H, t, J = 7.0 Hz). |
| 34 | 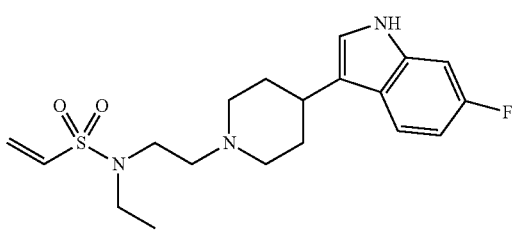 [SMILES: C=CS(=O)(=O)N(CC)CCN1CCC(c2c[nH]c3cc(F)ccc23)CC1] | $^1$H-NMR (400 MHz, CDCl$_3$) δ: 7.99 (1H, s), 7.50 (1H, dd, J = 8.8, 5.2 Hz), 7.02 (1H, dd, J = 9.8, 1.8 Hz), 6.93 (1H, d, J = 1.8 Hz), 6.85 (1H, ddd, J = 9.1, 9.1, 2.4 Hz), 6.53 (1H, dd, J = 16.8, 10.1 Hz), 6.20 (1H, d, J = 16.5 Hz), 5.90 (1H, d, J = 10.4 Hz), 3.45-3.32 (2H, m), 3.26 (2H, q, J = 7.1 Hz), 3.21-3.00 (2H, m), 2.91-2.55 (3H, m), 2.39-1.99 (4H, m), 1.98-1.75 (2H, m), 1.22 (3H, t, J = 7.0 Hz). |
| 35 | 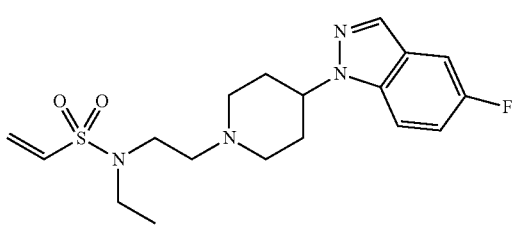 [SMILES: C=CS(=O)(=O)N(CC)CCN1CCC(n2ncc3cc(F)ccc32)CC1] | $^1$H-NMR (400 MHz, CDCl$_3$) δ: 7.93 (1H, s), 7.37 (1H, dd, J = 9.2, 4.3 Hz), 7.32 (1H, dd, J = 8.5, 2.4 Hz), 7.12 (1H, ddd, J = 8.9, 8.9, 2.4 Hz), 6.54 (1H, dd, J = 16.8, 10.1 Hz), 6.20 (1H, d, J = 16.5 Hz), 5.90 (1H, d, J = 10.4 Hz), 4.43-4.31 (1H, m), 3.36-3.22 (4H, m), 3.17-3.04 (2H, m), 2.67-2.57 (2H, m), 2.38-2.22 (4H, m), 2.08-1.95 (2H, m), 1.21 (3H, t, J = 7.0 Hz). |
| 36 | 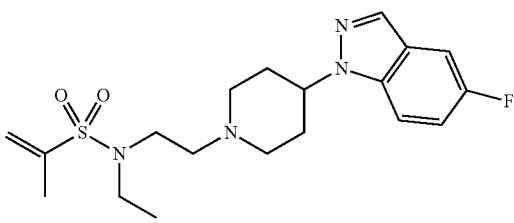 [SMILES: C=C(C)S(=O)(=O)N(CC)CCN1CCC(n2ncc3cc(F)ccc32)CC1] | $^1$H-NMR (400 MHz, CDCl$_3$) δ: 7.93 (1H, s), 7.40-7.35 (1H, m), 7.34-7.29 (1H, m), 7.16-7.09 (1H, m), 5.98 (1H, br s), 5.56 (1H, br s), 4.44-4.29 (1H, m), 3.42-3.26 (4H, m), 3.17-2.99 (2H, m), 2.72-2.55 (2H, m), 2.38-2.18 (4H, m), 2.08-1.93 (5H, m), 1.22 (3H, t, J = 7.3 Hz). |

Reference Example 37

3-[4-(1,2-Benzoisoxazol-3-yl)piperidin-1-yl]-N-ethylpropane-1-amine Dihydrochloride

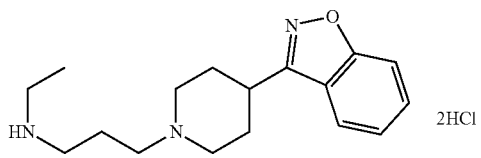 [SMILES: CCNCCCN1CCC(c2noc3ccccc23)CC1]

According to a similar method of Reference examples 18 and 21, the titled compound was prepared from 3-(piperidin-4-yl)benzo[d]isoxazole.

Reference Example 38

N-Ethyl-3-[4-(6-fluoro-1,2-benzoisoxazol-3-yl)piperazin-1-yl]propane-1-amine Dihydrochloride

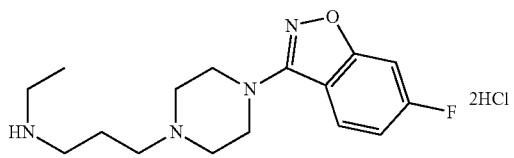 [SMILES: CCNCCCN1CCN(c2noc3cc(F)ccc23)CC1]

According to a similar method to Reference examples 18 and 21, the titled compound was prepared from 6-fluoro-3-(piperazin-1-yl)benzo[d]isoxazole monohydrochloride.

Test 1: Evaluation of Binding Activity for Human 5-$HT_{2A}$ Receptor, Human 5-$HT_7$ Receptor, and Human $D_2$ Receptor Binding affinity of the present compound for human 5-$HT_{2A}$ receptor, human 5-$HT_7$ receptor, and human $D_2$ receptor was measured by the following procedures.

CHO cell membrane fraction in which human 5-$HT_{2A}$ receptor, human 5-$HT_7$ receptor, or human $D_2$ receptor was expressed was purchased from PerkinElmer, Inc. In a test for evaluating binding affinity, a test compound dissolved in dimethylsulfoxide (DMSO) and each receptor membrane sample diluted in buffer were mixed with [3H]Ketanserin, [3H]SB-269970, or [3H]Spiperone (all purchased from PerkinElmer, Inc.) for 5-$HT_{2A}$ receptor, 5-$HT_7$ receptor, or $D_2$ receptor, respectively. Each mixture was incubated at room temperature for 60 minutes. Non specific binding to receptors was obtained from a competitive binding test in the presence of 10 μmol/L 8-OH-DPAT, 10 μmol/L Mianserin, or 10 μmol/L Spiperone, respectively. Radioactivity caused by binding to receptors was measured with a liquid scintillation counter (PerkinElmer, Inc.), and 50% inhibition concentration was calculated. Ki value was evaluated from dissociation constant which was calculated from saturated binding tests, and a substrate concentration, and it was used as an index for binding affinity. The results are shown in the following table.

| Example | 5-$HT_{2A}$ Ki (nmol/L) | 5-$HT_7$ Ki (nmol/L) | $D_2$ Ki (nmol/L) | $D_2$ Ki/ 5-$HT_{2A}$ Ki | $D_2$ Ki/ 5-$HT_7$ Ki |
|---|---|---|---|---|---|
| 1 | 2.0 | 2.5 | 226 | 113 | 89 |
| 2 | 2.1 | 9.3 | >1000 | >483 | >108 |
| 3 | 4.7 | 5.2 | >1000 | >212 | >192 |
| 4 | 0.4 | 0.7 | 267 | 738 | 390 |
| 5 | 0.6 | 2.4 | 116 | 191 | 48 |
| 6 | 0.8 | 5.7 | 278 | 364 | 49 |
| 7 | 0.2 | 1.0 | 79 | 519 | 80 |
| 8 | 1.4 | 6.2 | 294 | 216 | 47 |
| 9 | 0.4 | 1.6 | <100 | <231 | <64 |
| 10 | 1.7 | 2.7 | <100 | <59 | <38 |
| 11 | 1.5 | 5.2 | <100 | <68 | <19 |
| 12 | 1.7 | 6.9 | 711 | 425 | 103 |
| 13 | 4.6 | 20.3 | >1000 | >217 | >49 |
| 14 | 5.5 | 14.6 | >1000 | >183 | >68 |
| 15 | 4.8 | 26.4 | >1000 | >208 | >38 |
| 16 | 2.5 | 5.9 | 389 | 157 | 66 |
| 17 | 0.8 | 4.9 | 155 | 187 | 31 |
| 18 | 2.5 | 3.7 | 198 | 79 | 53 |
| 19 | 1.3 | 2.3 | 105 | 81 | 46 |
| 20 | 0.5 | 1.5 | 46 | 96 | 31 |
| 21 | 3.4 | 3.4 | >1000 | >296 | >295 |
| 22 | 2.1 | 5.8 | 528 | 252 | 91 |
| 23 | 1.8 | 7.9 | >1000 | >552 | >127 |
| 24 | 1.1 | 1.1 | <100 | <95 | <91 |
| 25 | 6.4 | 7.7 | 1389 | 217 | 182 |
| 26 | 58.0 | 22.1 | >10000 | >172 | >453 |
| 27 | 10.3 | 11.1 | 2164 | 210 | 195 |
| 28 | 2.2 | 10.0 | <100 | <45 | <10 |
| 29 | 1.1 | 2.6 | 146 | 135 | 55 |
| 30 | 0.8 | 6.6 | 153 | 184 | 23 |
| 31 | 1.0 | 1.2 | 89 | 91 | 77 |
| 32 | 97.0 | 109.7 | >10000 | >103 | >91 |
| 33 | 0.3 | 1.6 | 55 | 200 | 34 |
| 34 | 0.6 | 4.6 | 247 | 386 | 53 |
| 35 | 1.5 | 3.8 | <100 | <67 | <27 |
| 36 | 0.9 | 1.0 | 80 | 93 | 84 |
| 37 | 0.9 | 1.1 | <100 | <110 | <94 |
| 38 | 8.3 | 9.6 | 352 | 42 | 36 |
| 39 | 0.8 | 0.7 | <100 | <126 | <137 |
| 40 | 1.1 | 1.2 | 214 | 202 | 185 |
| 41 | 4.6 | 1.8 | <100 | <22 | <57 |
| 42 | 2.1 | 2.5 | 74 | 35 | 30 |
| 43 | 1.1 | 4.3 | <100 | <87 | <23 |
| 44 | 0.5 | 3.2 | <100 | <194 | <31 |
| 45 | 15.0 | 22.6 | >300 | >20 | >13 |
| 46 | 0.9 | 4.2 | 75 | 80 | 18 |
| 47 | 2.8 | 8.9 | 457 | 166 | 51 |
| 48 | 0.6 | 2.7 | 80 | 134 | 30 |
| 49 | 9.8 | 22.6 | >1000 | >102 | >44 |
| 50 | 4.0 | 13.5 | >1000 | >252 | >74 |
| 51 | 2.7 | 1.9 | 309 | 113 | 164 |
| 52 | 298.2 | 332.6 | >10000 | >34 | >30 |
| 53 | 1.1 | 1.4 | <100 | <92 | <71 |
| 54 | 2.0 | 2.6 | 116 | 58 | 45 |
| 55 | 1.1 | 0.1 | 78 | 69 | 890 |
| 56 | 1.2 | 0.4 | <100 | <86 | <254 |
| 57 | 1.6 | 8.7 | 210 | 128 | 24 |
| 58 | 53.2 | 19.4 | >1000 | >19 | >52 |
| 59 | 44.7 | 13.6 | >1000 | >22 | >74 |
| 60 | 19.9 | 24.3 | >1000 | >50 | >41 |
| 61 | 10.9 | 12.7 | 514 | 47 | 41 |
| 62 | 0.5 | 2.8 | 104 | 192 | 37 |
| 63 | 3.1 | 6.9 | 532 | 172 | 77 |
| 64 | 1.5 | 2.4 | 348 | 228 | 147 |
| 65 | 4.0 | 7.6 | 195 | 48 | 26 |
| 66 | 0.8 | 5.4 | 212 | 273 | 40 |
| 67 | 6.1 | 0.9 | <100 | <16 | <110 |
| 68 | 9.9 | 48.5 | 910 | 92 | 19 |
| 69 | 0.6 | 1.5 | <100 | <165 | <65 |
| 70 | 2.0 | 3.7 | 52 | 26 | 14 |
| 71 | 2.2 | 6.2 | 223 | 99 | 36 |
| 72 | 1.6 | 10.6 | <100 | <61 | <9 |
| 73 | 5.7 | 14.4 | 205 | 36 | 14 |
| 74 | 2.4 | 6.8 | 138 | 57 | 20 |
| 75 | 1.0 | 3.6 | 124 | 127 | 34 |
| 76 | 7.2 | 14.4 | 193 | 27 | 13 |

Test 2: Evaluation of Antagonist Activity for Human 5-HT$_{2A}$ Receptor and Human 5-HT$_7$ Receptor Aequorin, Gα 16 protein, and each receptor were transiently expressed in CHO-K1 cells (Chinese hamster ovary). The cells were cultivated in a $CO_2$ incubator at 37° C. overnight, seeded into a 384-well plate, and stood at room temperature for 2 hours. Each compound dissolved in DMSO was added thereto, and changes in luminescence were measured by FDSS/μCELL drug discovery screening support system (Hamamatsu Photonics K.K.). As for antagonist activity, inhibitory activity of each compound was calculated by setting the luminescence level of wells to which 10 μmol/L endogenous ligand was added as 100%. The results are shown in the following table.

| Example | 5-HT$_{2A}$ antagonist activity IC$_{50}$ (nmol/L) | 5-HT$_7$ antagonist activity IC$_{50}$ (nmol/L) |
|---|---|---|
| 1 | 8 | 37 |
| 2 | 12 | 94 |
| 3 | 62 | 95 |
| 4 | 44 | 31 |
| 5 | 9 | 66 |
| 6 | 48 | 66 |
| 7 | 8 | 11 |
| 8 | 26 | 8 |
| 9 | 15 | 8 |
| 10 | 40 | 9 |
| 11 | 9 | 67 |
| 12 | 78 | 82 |
| 13 | 76 | 81 |
| 14 | 79 | 82 |
| 15 | 60 | 86 |
| 16 | 59 | 90 |
| 17 | 49 | 66 |
| 18 | 58 | 72 |
| 19 | 76 | 61 |
| 20 | 19 | 48 |
| 21 | 73 | 68 |
| 22 | 738 | 40 |
| 23 | 277 | 68 |
| 24 | 7 | 41 |
| 25 | 90 | 26 |
| 26 | 843 | 71 |
| 27 | 64 | 73 |
| 28 | 95 | 80 |
| 29 | 39 | 99 |
| 30 | 45 | 39 |
| 31 | 55 | 64 |
| 32 | 890 | 73 |
| 33 | 8 | 59 |
| 34 | 6 | 78 |
| 35 | 33 | 81 |
| 36 | 13 | 82 |
| 37 | 21 | 66 |
| 38 | 756 | 59 |
| 39 | 8 | 9 |
| 40 | 9 | 2 |
| 41 | 7 | 7 |
| 42 | 8 | 9 |
| 43 | 9 | 82 |
| 44 | 10 | 77 |
| 45 | 640 | 49 |
| 46 | 9 | 83 |
| 47 | 94 | 43 |
| 48 | 10 | 18 |
| 49 | 633 | 16 |
| 50 | 49 | 81 |
| 51 | 57 | 62 |
| 52 | 946 | 177 |
| 53 | 72 | 44 |
| 54 | 31 | 1 |
| 55 | 7 | 3 |
| 56 | 7 | 6 |
| 57 | 56 | 100 |
| 58 | 3643 | 103 |
| 59 | 5888 | 62 |
| 60 | 819 | 72 |
| 61 | 94 | 15 |
| 62 | 53 | 28 |
| 63 | 65 | 46 |
| 64 | 44 | 101 |
| 65 | 103 | 81 |
| 66 | 37 | 70 |
| 67 | 94 | 72 |
| 68 | 949 | 91 |
| 69 | 745 | 85 |
| 70 | 67 | 9 |
| 71 | 25 | 78 |
| 72 | 42 | 8 |
| 73 | 68 | 81 |
| 74 | 68 | 77 |
| 75 | 306 | 80 |
| 76 | 551 | 65 |

Test 3-1: Metabolic Stability Test in Human Hepatic Microsome

The metabolic stability of the present compound in human hepatic microsome was evaluated as mentioned below. Human hepatic microsome was obtained from Xenontech. Human hepatic microsome, NADPH, and each test compound were mixed in 25 mmol/L phosphate buffer solution (pH 7.4) to reach the following concentrations as shown below, and the mixture was incubated at 37° C. for 30 minutes.

Human hepatic microsome: 0.1 mg/mL

NADPH: 3.2 mmol/L

Test compound: 0.1 μmol/L

The residual ratio of test compound in each sample after 30 minutes was measured by LC-MS, and the metabolic stability in human hepatic microsome was calculated from the following formula.

Metabolic stability in human hepatic microsome (mL/min/mg protein)=−LN (residual ratio)/30/0.1

The results are shown in the following table.

| Example | Metabolic stability in human hepatic microsome (mL/min/mg protein) |
|---|---|
| 1 | <0.05 |
| 2 | <0.05 |
| 3 | <0.05 |
| 4 | <0.05 |
| 5 | 0.186 |
| 6 | 0.053 |
| 7 | 0.08 |
| 8 | 0.108 |
| 9 | <0.05 |
| 10 | <0.05 |
| 11 | <0.05 |
| 12 | 0.089 |
| 13 | 0.054 |
| 16 | <0.05 |
| 17 | <0.05 |
| 18 | <0.05 |
| 19 | <0.05 |

-continued

| Example | Metabolic stability in human hepatic microsome (mL/min/mg protein) |
|---|---|
| 20 | <0.05 |
| 21 | <0.05 |
| 22 | <0.05 |
| 23 | <0.05 |
| 24 | <0.05 |
| 25 | <0.05 |
| 26 | <0.05 |
| 27 | <0.05 |
| 29 | <0.05 |
| 30 | <0.05 |
| 31 | <0.05 |
| 33 | 0.268 |
| 34 | <0.05 |
| 35 | <0.05 |
| 36 | <0.05 |
| 37 | <0.05 |
| 38 | <0.05 |
| 39 | <0.05 |
| 40 | <0.05 |
| 41 | <0.05 |
| 42 | <0.05 |
| 43 | <0.05 |
| 44 | <0.05 |
| 45 | <0.05 |
| 46 | <0.05 |
| 47 | <0.05 |
| 48 | <0.05 |
| 49 | <0.05 |
| 50 | <0.05 |
| 51 | <0.05 |
| 53 | <0.05 |
| 54 | <0.05 |
| 55 | 0.059 |
| 56 | <0.05 |
| 57 | 0.06 |
| 58 | <0.05 |
| 59 | 0.079 |
| 61 | <0.05 |
| 62 | <0.05 |
| 63 | <0.05 |
| 64 | 0.097 |
| 65 | <0.05 |
| 66 | <0.05 |
| 67 | <0.05 |
| 68 | <0.05 |
| 69 | <0.05 |
| 70 | <0.05 |
| 71 | <0.05 |
| 72 | 0.057 |
| 74 | <0.05 |
| 75 | <0.05 |
| 76 | <0.05 |

Test 3-2: Metabolic Stability Test in Human Hepatic Microsome

For more accurate evaluation of the metabolic stability in human hepatic microsome, the metabolic stability of the present compound in human hepatic microsome was evaluated at an appropriate concentration of human hepatic microsome as mentioned below. Human hepatic microsome was obtained from Xenontech. Human hepatic microsome, NADPH, and each test compound were mixed in 25 mmol/L phosphate buffer solution (pH 7.4) to reach the following concentrations as shown below, and the mixture was incubated at 37° C. for 60 minutes.

Human hepatic microsome: 0.5 or 1.0 mg/mL
NAPDH: 3.2 mmol/L
Test compound: 0.1 µmol/L The residual ratio of a test compound in each sample after 30 or 60 minutes was measured by LC-MS, and the metabolic stability in human hepatic microsome was calculated from the following formula.

Metabolic stability in human hepatic microsome (mL/min/mg protein)=−LN (residual ratio)/reaction time/concentration of human hepatic microsome The results are shown in the following table.

| Example | Metabolic stability in human hepatic microsome (mL/min/mg protein) |
|---|---|
| 16 | 0.018 |
| 17 | 0.0025 |
| 51 | 0.016 |

Test 4: Predictive Test of Human Half Life

The disappearance half life of the present compound in human was predicted as mentioned below.

The present compound was intravenously administered to a rat as an aqueous solution of 0.01 mol/L hydrochloric acid. Blood was collected on 5 minutes, 15 minutes, 30 minutes, 1 hour, 2 hours, 4 hours, 6 hours, and 24 hours after the administration. Plasma was obtained from the collected blood, the drug concentration in plasma was measured by LC-MS, and the distribution volume of rat was calculated from the transition of the concentration.

The unbound fraction rate of the present compound in human or rat serum was measured by equilibrium dialysis method.

The half-life in human was calculated according to the following formula using the results of the distribution volume of rat, the unbound fraction rate in human or rat serum, and the metabolic stability in human hepatic microsome obtained in Test 3-2.

Distribution volume of human=Distribution volume of rat×Unbound fraction rate in human serum/Unbound fraction rate in rat serum Human hepatic clearance=(Hepatic blood flow of human×Unbound fraction rate in human serum× 56.7×Metabolic stability in human hepatic microsome)/(Hepatic blood flow of human+ Unbound fraction rate in human serum×56.7× Metabolic stability in human hepatic microsome)

Half-life in human=0.693×Distribution volume of human/Human hepatic clearance

The results are shown in the following table.

| Example | Predicted half-life (h) |
|---|---|
| 16 | 3 |
| 17 | 27 |
| 51 | 6 |

Test 5: Evaluation of Inhibitory Activity for hERG Channel

Inhibitory activity of the present compound for hERG channel was measured by whole cell patch clamp method with an auto patch clamp system using CHO cells in which hERG channel involved in human rapidly activating delayed rectifier potassium current ($I_{Kr}$) was forcibly expressed.

(Preparation of Cell Suspension)

hERG-CHO cells purchased from ChanTest Cop. were cultured in a $CO_2$ incubator at 37° C., and dissociated from a flask with trypsin shortly before the measurement of hERG current to prepare a cell suspension.

(Preparation of Solution)

Extracellular and intracellular fluids used in the measurement were prepared as follows.

Extracellular fluid: 2 mmol/L $CaCl_2$, 1 mmol/L $MgCl_2$, 10 mmol/L HEPES, 4 mmol/L KCl, 145 mmol/L NaCl, 10 mmol/L Glucose Intracellular fluid: 10 mmol/L HEPES, 10 mmol/L EGTA, 20 mmol/L KCl, 130 mmol/L KF Test compound solution: A test compound was dissolved in DMSO to reach the concentration of 2 mmol/L or 20 mmol/L in order to prepare a test compound solution. The test compound solution was further diluted 200 times with the extracellular fluid, and serial-diluted with the extracellular fluid to prepare a test compound solution in each concentration which is necessary to calculate $IC_{50}$ value of hERG inhibition.

(Measurement of Current Value and Data Analysis)

The cell suspension, the extracellular fluid, the intracellular fluid, and the measurement plate were set in an auto patch clamp system, and hERG current was measured by whole cell patch clamp method. A voltage-protocol was as follows: the holding potential was adjusted to −80 mV, the depolarizing pulse was provided at −50 mV to +20 mV for 5 seconds, the repolarizing pulse was provided at −50 mV for 5 seconds, then the potential was returned to the holding potential. Each pulse interval was 15 seconds. The data analysis was carried out with Qube Assay Software (Sophion Sophion). The test was carried out by applying incrementally 4 concentrations of each test compound, and the average of the maximum peak tail currents which were obtained from the last 3 stimulations in each concentration was determined as the evaluated data. Based on the current inhibition rate for a pre-applied current at each concentration of each test compound, $IC_{50}$ value was calculated by Hill equation with the software.

The results are shown in the following table.

| Example | hERG inhibitory $IC_{50}$ (μmol/L) | hERG inhibitory $IC_{50}$ (nmol/L)/ 5-$HT_{2A}$ Ki (nmol/L) | hERG inhibitory $IC_{50}$ (nmol/L)/ 5-$HT_7$ Ki (nmol/L) |
|---|---|---|---|
| 1 | 4.8 | 2401 | 1896 |
| 2 | 7.4 | 3575 | 796 |
| 3 | >10 | >2122 | >1922 |
| 4 | 7.1 | 19617 | 10367 |
| 5 | 1.1 | 1810 | 455 |
| 6 | 1.5 | 1958 | 265 |
| 7 | 3.5 | 22975 | 3526 |
| 8 | 4.2 | 3088 | 677 |
| 9 | 5.4 | 12480 | 3453 |
| 10 | 3.6 | 2135 | 1351 |
| 11 | 10.5 | 7172 | 2034 |
| 12 | 2.2 | 1313 | 319 |
| 13 | 2.9 | 629 | 143 |
| 14 | 9.6 | 1754 | 656 |
| 16 | 4.8 | 1939 | 814 |
| 17 | 2.8 | 3381 | 567 |
| 18 | 4.1 | 1637 | 1097 |
| 19 | >10 | >7705 | >4405 |
| 20 | 4.2 | 8787 | 2849 |
| 21 | 15.3 | 4529 | 4520 |
| 22 | >10 | >4475 | >1726 |
| 23 | >10 | >5520 | >1266 |
| 24 | 5.5 | 5203 | 4988 |
| 25 | >10 | >1563 | >1307 |
| 26 | >10 | >172 | >453 |
| 27 | >10 | >968 | >899 |
| 29 | 0.9 | 830 | 341 |
| 30 | 1.2 | 1441 | 182 |
| 31 | 3.1 | 3169 | 2694 |
| 33 | 2.2 | 8013 | 1374 |
| 34 | 7.3 | 11440 | 1578 |
| 35 | 4.3 | 2888 | 1143 |
| 36 | 1.3 | 1504 | 1361 |
| 37 | >10 | >10968 | >9375 |
| 38 | >10 | >1200 | >1036 |
| 39 | 4.7 | 5934 | 6462 |
| 40 | 9.9 | 9377 | 8589 |
| 41 | 6.7 | 1461 | 3821 |
| 42 | 6.4 | 3022 | 2583 |
| 43 | 7.0 | 6091 | 1613 |
| 44 | 6.4 | 12428 | 1977 |
| 45 | >10 | >665 | >442 |
| 46 | 5.7 | 6053 | 1373 |
| 47 | 5.4 | 1954 | 607 |
| 48 | 2.9 | 4870 | 1090 |
| 49 | >10 | >1017 | >442 |
| 50 | 6.2 | 1563 | 458 |
| 51 | 6.9 | 2536 | 3665 |
| 53 | 7.2 | 6616 | 5125 |
| 54 | 7.4 | 3685 | 2855 |
| 55 | 7.4 | 6575 | 84634 |
| 56 | 2.1 | 1805 | 5341 |
| 57 | 6.2 | 3785 | 717 |
| 58 | >10 | >188 | >516 |
| 59 | >10 | >224 | >738 |
| 61 | >10 | >916 | >790 |
| 62 | 5.4 | 9970 | 1944 |
| 63 | 14.5 | 4677 | 2101 |
| 64 | >10 | >6551 | >4214 |
| 65 | >10 | >2477 | >1314 |
| 66 | >10 | >12871 | >1865 |
| 67 | >10 | >1632 | >11030 |
| 69 | >10 | >16548 | >6545 |
| 70 | >10 | >4913 | >2739 |
| 71 | >10 | >4452 | >1624 |
| 72 | 9.9 | 6029 | 933 |
| 74 | 6.7 | 2795 | 991 |
| 75 | 3.8 | 3881 | 1051 |
| 76 | >10 | >1394 | >697 |

Test 6: Fear Conditioning Test

Male SD rats were used. For preparation of an administration solution, a test compound was dissolved in 0.01 mol/L hydrochloric acid, and the aqueous solution was used.

Fear conditioning test was conducted as mentioned below using Image J FZ2 for Contextual and cued fear conditioning test from O'HARA & CO., LTD.

An animal was placed into a chamber quipped in the Image J FZ2 for Contextual and cued fear conditioning test, and electric stimulations were applied 7 times at 0.5 mA for 10 seconds. Then, a rat was gently removed from a chamber, and on the next day, the administration solution (a solvent or test compound solution) was subcutaneously administered, the animal was placed in a chamber on 30 minutes later. The percentage of freezing reaction time from when an animal was placed in a chamber to 300 seconds later was used as a test result.

Analysis of the test results were carried out as follows.

Parametric Dunnett's multiple comparison was conducted on both of the test compound administration group and the solvent administration group (significance level: 5% on both sides). When the test compound administration group showed a significant suppression of the freezing reaction time, compared with the solvent administration group, it was regarded as showing an anxiolytic effect.

The results of this test using the compound of Example 17 are shown in FIG. 1.

Test 7: Measurement of the Amount of Released Glutamic Acid in Rat Brain

A cannula was indwelled in a prefrontal cortex position in a male Wistar rat, and the rat was subjected to the test after a recovery period of at least 1 week.

For calibration of a biosensor, 5 mM solution of glutamic acid and 100 mM solution of ascorbic acid were used. Released glutamic acid was measured with the biosensor which had calibrated. The measurement was started 12 hours or more after the biosensor was inserted into a guide cannula. After administration of a test compound, the measurement was performed for 2 hours or more.

The average amount of released glutamic acid on 30 minutes before administration was used as a standard, and the area under the curve was calculated on 2 hours after administration. The data of the compound administration group was compared with that of the solvent administration group.

The average values of each group were compared by parametric Dunnett's multiple comparison test, and when the test compound administration group showed a significant high value compared with the solvent administration group, it was regarded as showing a promoting effect of releasing glutamic acid (significance level: 5% on both sides).

The results of this test using the compound of Example 17 are shown in FIG. 2.

Test 8: Evaluation of Binding Activity for Side-Effect-Related Receptor

Binding affinity of the present compound for side-effect-related receptor, such as adrenergic α1A receptor, can be measured by the following method.

Evaluation test for binding is carried out as follows with the CHO cell membrane fraction in which human target receptor is expressed. A test compound dissolved in dimethylsulfoxide (DMSO), each receptor membrane sample diluted with buffer, and [3H]-labelled ligand which has strong binding affinity to each target receptor are mixed. Each mixture is incubated at room temperature, added quickly on a glassfiber filter plate (Multiscreen FB, Millipore, Inc.), and vacuum-filtered. Radioactivity remaining on the filter is measured with a liquid scintillation counter (PerkinElmer, Inc.). Binding inhibition rate is calculated from the following formula. A control compound which has strong binding affinity to a target receptor is used to calculate the non-specific binding amount to the receptor membrane sample, instead of a test compound.

Binding inhibition rate to target receptor (%)=100-
100×{(Binding amount of [3H]-labelled ligand
in the presence of test compound)}−(Binding
amount of [3H]-labelled ligand in the presence
of 10 μmol/L control compound)}/{(Binding
amount of [3H]-labelled ligand in the absence
of test compound)}−(Binding amount of [3H]-
labelled ligand in the presence of 10 μmol/L
control compound)}

Test 9: Evaluation of Intracerebral Transferability (Test for Intracerebral Transferability in Rats)

In this test, intracerebral transferability of the present compound was evaluated by the following method. The present compounds were subcutaneously administered as a solution in saline, or orally administered as a suspension in methyl cellulose to a 7-week-old SD or WKY rat. Plasma and brain were collected on 0.5 hour, 1 hour, or 2 hours after the administration in order to measure the drug concentrations in plasma and brain by LC-MS.

Binding rates of the present compound to plasma and brain protein were measured by equilibrium dialysis method.

Kp,uu,brain (unbound drug concentration ratio between brain/plasma) can be calculated by applying the compound concentrations in plasma and brain and the binding rates to plasma and brain protein obtained from the above test into the following formula.

Kp,uu,brain=(Compound concentration in brain×
(100−Binding rate to brain protein (%))/100)/
(Compound concentration in plasma×(100−
Binding rate to plasma protein (%))/100)

The results of Test 9 are shown in the following table.

| Example | Kp, uu, brain |
| --- | --- |
| 2 | 0.35 |
| 16 | 1.32 |
| 17 | 0.58 |
| 18 | 0.56 |
| 19 | 0.33 |
| 21 | 0.54 |
| 23 | 1.47 |
| 41 | 0.63 |
| 51 | 1.26 |
| 63 | 0.35 |

Test 10: Evaluation of Hepatotoxic Risk (Dansyl Glutathione (dGSH) Trapping Assay)

The present compound was metabolized in hepatic microsome, and from the resulted metabolite, reactive metabolite which reacts with dancyl glutathione (dGSH) was detected and quantified as the following method. Measurement was carried out with a screening robot (Tecan) for metabolic reaction, and with a fluorescence detection UPLC system (Waters) for metabolite-dGSH binding concentration.

(Preparation of Solution)

The present compound was dissolved in DMSO to prepare 10 mmol/L test compound solution. 7.6 mL of potassium phosphate buffer (500 mmol/L, pH 7.4), 1.9 mL of human hepatic microsome (Xenotech, 20 mg protein/mL), and 1.27 mL of pure water were mixed to prepare a microsome solution. To 3.78 mL of the microsome solution was added 0.67 mL of pure water to prepare a microsome (dGSH(−)) solution. To 6.48 mL of the microsome solution was added 1.14 mL of the dGSH solution (20 mmol/L) to prepare a microsome (dGSH(+)) solution. 80.9 mg of NADPH was dissolved in 30 mL of pure water to prepare a cofactor solution. 33 mg of tris(2-carboxyethyl)phosphine (TECP) was dissolved in 115 mL of methanol to prepare a reaction stop solution.

(Reaction)

12 μL of the test compound solution was mixed with 388 μL of pure water, and the mixture was dispensed in 50 μL each into 6 wells of a 96-well plate. The 6 wells were divided into 3 groups of 2 wells, and each was named as "reaction group", "unreacted group", and "dGSH-free group". To the "reaction group" and "unreacted group" was added the microsome (dGSH(+)) solution, and to the "dGSH-free group" was added the microsome (dGSH(−)) solution in 50 μL each. To the "reaction group" and "dGSH-free group" was added to the cofactor solution, and to the "unreacted group" was added pure water in 50 μL each. After incubated at 37° C. for 60 minutes, the reaction stop solution was added in 450 μL each to stop the reaction. To the "reaction group" and "dGSH-free group" was added pure water, and to the "unreacted group" was added the cofactor solution in 50 μL each. The plate was cooled at −20° C. for 1 hour, and the solutions were centrifuged (4000 rpm, 10 minutes). Supernatants were collected into another plate and subjected to analysis.

(Analysis)

Metabolite-dGSH binding concentration was measured by the following conditions, using a fluorescence detection UPLC system.

Column: Waters ACQUITY UPLC BEHC18 1.7 μm 2.1×10 mm

Eluent: A, 0.2% aqueous formic acid; B, 0.2% formic acid/acetonitrile

Gradient: B, 20% (0 min)→70% (9.33 min)→90% (10.63 min)→20% (11 min)→20% (14 min)

Fluorescence intensity was corrected with the composition of organic solvent at the time of elution because fluorescence intensity changes depending on the composition of organic solvent.

The results of Test 10 are shown in the following table.

| Example | Metabolite-dGSH binding concentration (μM) |
|---|---|
| 1 | N.D. |
| 2 | 0.127 |
| 3 | N.D. |
| 4 | 0.165 |
| 5 | N.D. |
| 6 | N.D. |
| 7 | N.D. |
| 8 | 0.223 |
| 9 | N.D. |
| 10 | N.D. |
| 11 | N.D. |
| 12 | N.D. |
| 13 | 0.214 |
| 14 | 0.089 |
| 16 | N.D. |
| 17 | N.D. |
| 18 | N.D. |
| 19 | 0.175 |
| 20 | 1.661 |
| 21 | 0.133 |
| 22 | 0.509 |
| 23 | 0.173 |
| 24 | 7.645 |
| 25 | N.D. |
| 26 | N.D. |
| 27 | N.D. |
| 29 | 0.091 |
| 30 | 0.101 |
| 31 | N.D. |
| 33 | N.D. |
| 34 | 0.268 |
| 35 | 0.153 |
| 36 | 0.161 |
| 37 | 0.108 |
| 38 | N.D. |
| 39 | N.D. |
| 40 | 0.125 |
| 41 | N.D. |
| 42 | N.D. |
| 43 | 0.177 |
| 44 | 0.096 |
| 45 | N.D. |
| 46 | 0.156 |
| 47 | N.D. |
| 48 | N.D. |
| 49 | 0.45 |
| 50 | N.D. |
| 51 | N.D. |
| 53 | 0.063 |
| 54 | N.D. |
| 55 | 0.057 |
| 56 | 0.514 |
| 57 | N.D. |
| 58 | N.D. |
| 59 | N.D. |
| 61 | N.D. |
| 62 | 0.857 |
| 63 | 0.268 |
| 64 | 0.432 |
| 65 | 0.112 |
| 66 | 0.222 |
| 67 | 0.113 |
| 69 | N.D. |
| 70 | 0.257 |
| 71 | 0.132 |
| 72 | 0.147 |
| 74 | N.D. |
| 75 | N.D. |
| 76 | N.D. |

(N.D. means below detection limit.)

INDUSTRIAL APPLICABILITY

The present compound shows antagonist activity for the serotonin 5-$HT_{2A}$ receptor and the serotonin 5-$HT_7$ receptor, and therefore, the present compound is useful as a medicament for treating neuropsychiatric diseases.

The invention claimed is:

1. A compound which is represented by any one of the following formulae:

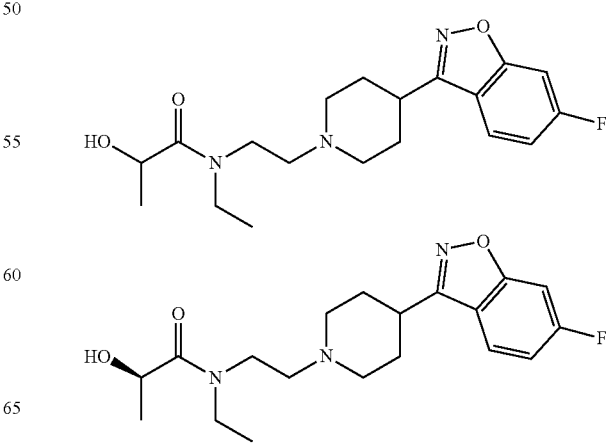

93
-continued

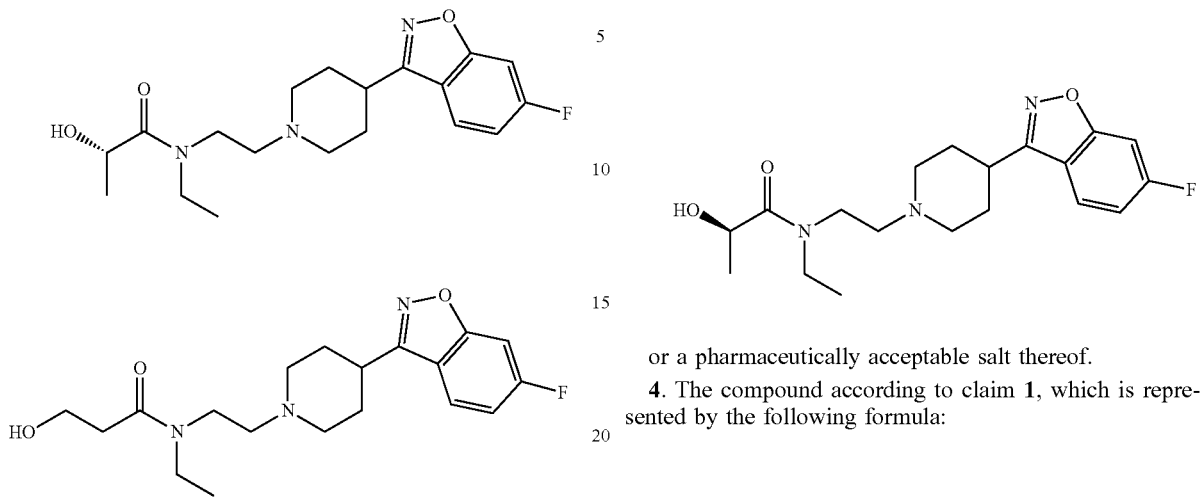

or a pharmaceutically acceptable salt thereof.

2. The compound according to claim 1, which is represented by the following formula:

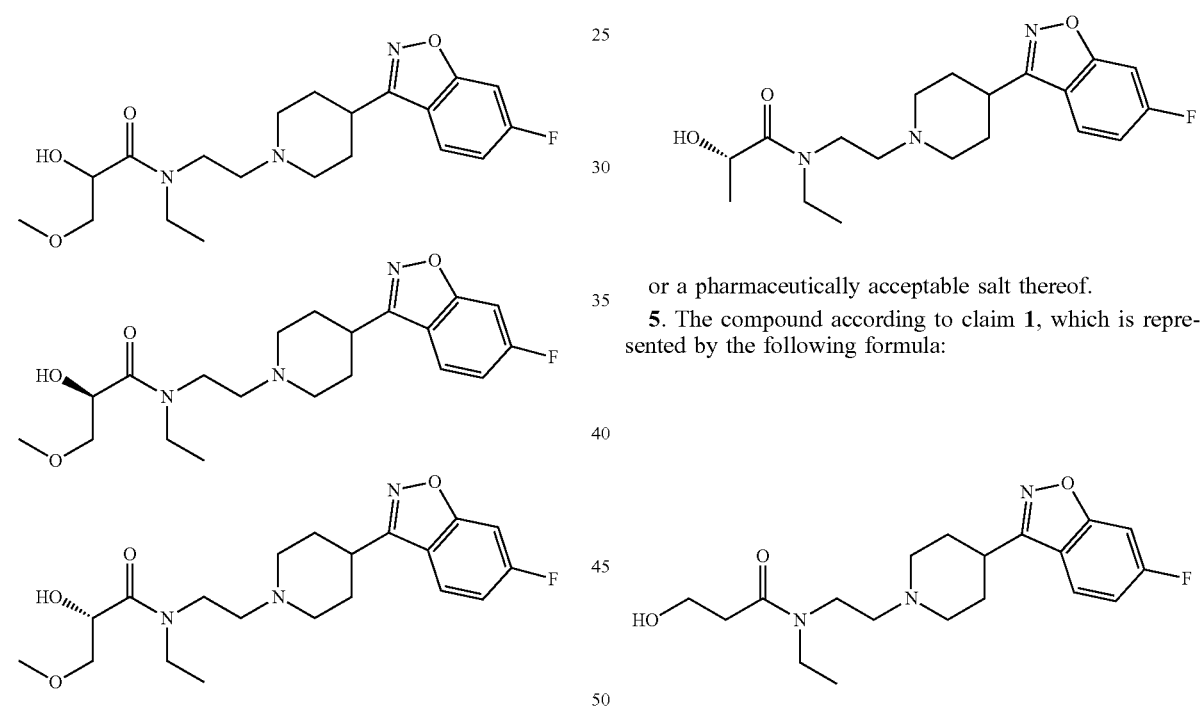

or a pharmaceutically acceptable salt thereof.

3. The compound according to claim 1, which is represented by the following formula:

or a pharmaceutically acceptable salt thereof.

4. The compound according to claim 1, which is represented by the following formula:

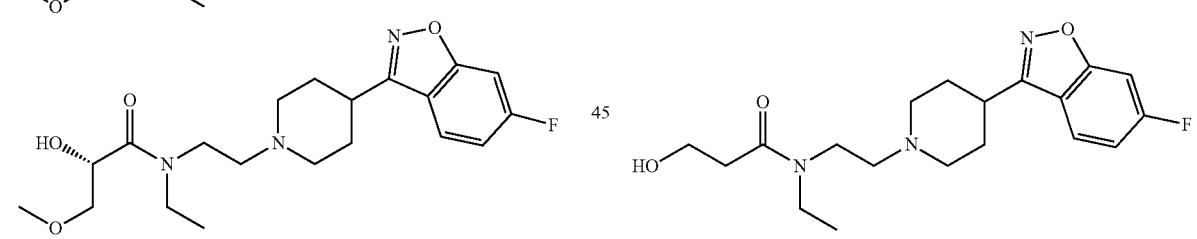

or a pharmaceutically acceptable salt thereof.

5. The compound according to claim 1, which is represented by the following formula:

or a pharmaceutically acceptable salt thereof.

6. The compound according to claim 1, which is represented by the following formula:

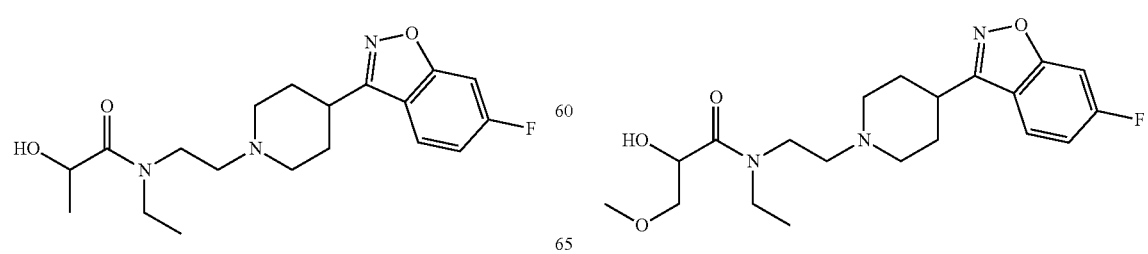

or a pharmaceutically acceptable salt thereof.

7. The compound according to claim 1, which is represented by the following formula:
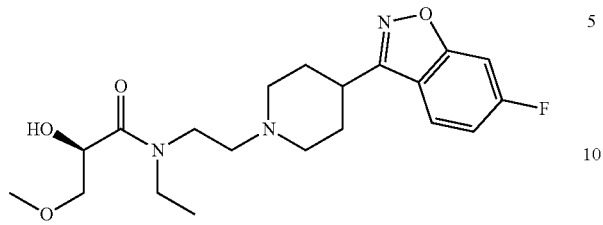
or a pharmaceutically acceptable salt thereof.
8. The compound according to claim 1, which is represented by the following formula:
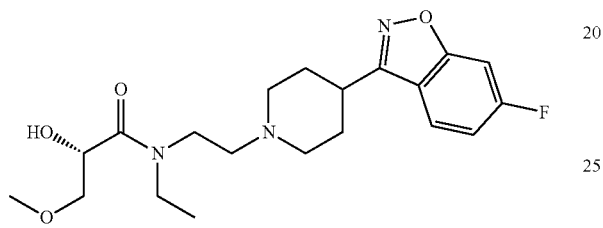
or a pharmaceutically acceptable salt thereof.
* * * * *